(12) United States Patent
Sharma et al.

(10) Patent No.: US 10,779,980 B2
(45) Date of Patent: Sep. 22, 2020

(54) INTRAGASTRIC DEVICE FOR TREATING OBESITY

(71) Applicant: SynerZ Medical, Inc., Newark, DE (US)

(72) Inventors: Virender K. Sharma, Paradise Valley, AZ (US); Raghuveer Basude, Freemont, CA (US)

(73) Assignee: SynerZ Medical, Inc., Newark, DE (US)

( * ) Notice: Subject to any disclaimer, the term of this patent is extended or adjusted under 35 U.S.C. 154(b) by 392 days.

(21) Appl. No.: 15/496,625

(22) Filed: Apr. 25, 2017

(65) Prior Publication Data
US 2017/0312111 A1 Nov. 2, 2017

Related U.S. Application Data

(60) Provisional application No. 62/328,326, filed on Apr. 27, 2016.

(51) Int. Cl.
*A61F 5/00* (2006.01)
(52) U.S. Cl.
CPC ............ *A61F 5/0036* (2013.01); *A61F 5/003* (2013.01); *A61F 5/0076* (2013.01); *A61F 5/0083* (2013.01)
(58) Field of Classification Search
CPC ...... A61F 5/003; A61F 5/0036; A61F 5/0076; A61F 5/0083
See application file for complete search history.

(56) References Cited

U.S. PATENT DOCUMENTS

| | | | |
|---|---|---|---|
| 1,899,781 | A | 2/1933 | Twiss |
| 2,464,933 | A | 3/1949 | Kaslow |
| 3,780,740 | A | 12/1973 | Rhea |
| 4,133,315 | A | 1/1979 | Berman |

(Continued)

FOREIGN PATENT DOCUMENTS

| | | |
|---|---|---|
| AU | 2010271294 A1 | 2/2012 |
| AU | 2011203951 A1 | 7/2012 |

(Continued)

OTHER PUBLICATIONS

US 8,668,662 B2, 03/2014, Levine (withdrawn)

(Continued)

*Primary Examiner* — Leslie R Deak

(57) ABSTRACT

A intragastric device that contains a compressible free-floating structure and a sleeve attached thereto is provided. The device is considered to be anchorless as the sleeve is not physically attached to any portion of the GI tract. The device is configurable between a compressed pre-deployment configuration and an expanded post-deployment configuration. The free-floating device may be composed of a shape memory material such a nitinol. In some embodiments, the free-floating structure is space occupying and non-porous. The sleeve may be attached to the free-floating structure, such as with sutures and/or glue. In some embodiments, a stent may be inserted at the proximal end of the sleeve. A second free-floating structure may be connected to the free-floating structure such that there is an upper structure and a lower structure. In some embodiments, the gastrointestinal device is used to deliver prebiotic and/or probiotic therapy to a patient.

10 Claims, 51 Drawing Sheets

(56) References Cited

U.S. PATENT DOCUMENTS

| | | |
|---|---|---|
| 4,134,405 A | 1/1979 | Smit |
| 4,246,893 A | 1/1981 | Berson |
| 4,270,542 A | 6/1981 | Plumley |
| 4,279,251 A | 7/1981 | Rusch |
| 4,315,509 A | 2/1982 | Smit |
| 4,403,604 A | 9/1983 | Wilkinson |
| 4,416,267 A | 11/1983 | Garren |
| 4,441,215 A | 4/1984 | Kaster |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner |
| 4,723,547 A | 2/1988 | Kullas |
| 4,738,667 A | 4/1988 | Galloway |
| 4,763,653 A | 8/1988 | Rockey |
| 4,767,627 A | 8/1988 | Caldwell |
| 4,823,808 A | 4/1989 | Clegg |
| 4,846,836 A | 7/1989 | Reich |
| 4,878,905 A | 11/1989 | Blass |
| 4,899,747 A | 2/1990 | Garren |
| 4,913,141 A | 4/1990 | Hillstead |
| 5,035,706 A | 7/1991 | Giantureo |
| 5,037,387 A | 8/1991 | Quinn |
| 5,041,126 A | 8/1991 | Gianturco |
| 5,057,091 A | 10/1991 | Andersen |
| 5,104,399 A | 4/1992 | Lazarus |
| 5,152,756 A | 10/1992 | Quinn |
| 5,163,952 A | 11/1992 | Froix |
| 5,188,104 A | 2/1993 | Wernike |
| 5,211,668 A | 5/1993 | Clouse |
| 5,234,454 A | 8/1993 | Bangs |
| 5,236,423 A | 8/1993 | Mix |
| 5,246,456 A | 9/1993 | Wilkinson |
| 5,259,399 A | 11/1993 | Brown |
| 5,279,553 A | 1/1994 | Winkler |
| 5,282,824 A | 2/1994 | Gianturco |
| 5,290,217 A | 3/1994 | Campos |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,327,914 A | 7/1994 | Shlain |
| 5,345,949 A | 9/1994 | Shlain |
| 5,364,353 A | 11/1994 | Corfitsen |
| 5,387,235 A | 2/1995 | Chuter |
| 5,401,241 A | 3/1995 | Delany |
| 5,405,377 A | 4/1995 | Cragg |
| 5,405,378 A | 4/1995 | Strecker |
| 5,423,872 A | 6/1995 | Cigaina |
| 5,432,872 A | 7/1995 | Stewart et al. |
| 5,443,498 A | 8/1995 | Fontaine |
| 5,456,713 A | 10/1995 | Chuter |
| 5,480,423 A | 1/1996 | Ravenscroft |
| 5,507,767 A | 4/1996 | Maeda |
| 5,507,771 A | 4/1996 | Gianturco |
| 5,514,176 A | 5/1996 | Bosley, Jr. |
| 5,536,274 A | 7/1996 | Neuss |
| 5,562,697 A | 10/1996 | Christiansen |
| 5,569,219 A | 10/1996 | Hakki |
| 5,593,434 A | 1/1997 | Williams |
| 5,611,787 A | 3/1997 | Demeter |
| 5,624,430 A | 4/1997 | Eton |
| 5,630,797 A | 5/1997 | Diedrich |
| 5,637,699 A | 6/1997 | Dorn et al. |
| 5,653,743 A | 8/1997 | Martin |
| 5,658,322 A | 8/1997 | Fleming |
| 5,662,713 A | 9/1997 | Andersen |
| 5,665,064 A | 9/1997 | Bodicky |
| 5,668,263 A | 9/1997 | Hoyer et al. |
| 5,674,241 A | 10/1997 | Bley |
| 5,690,692 A | 11/1997 | Fleming |
| 5,693,084 A | 12/1997 | Chuter |
| 5,700,272 A | 12/1997 | Gordon |
| 5,709,657 A | 1/1998 | Zimmon |
| 5,713,910 A | 2/1998 | Gordon |
| 5,715,832 A | 2/1998 | Koblish |
| 5,720,776 A | 2/1998 | Chuter |
| 5,733,325 A | 3/1998 | Robinson |
| 5,741,277 A | 4/1998 | Gordon |
| 5,741,279 A | 4/1998 | Gordon |
| 5,749,918 A | 5/1998 | Hogendijk |
| 5,755,777 A | 5/1998 | Chuter |
| 5,771,903 A | 6/1998 | Jakobsson |
| 5,800,456 A | 9/1998 | Maeda |
| 5,800,526 A | 9/1998 | Anderson |
| 5,817,466 A | 10/1998 | Hoyer et al. |
| 5,820,584 A | 10/1998 | Crabb |
| 5,830,229 A | 11/1998 | Konya |
| 5,835,897 A | 11/1998 | Dang |
| 5,843,164 A | 12/1998 | Frantzen |
| 5,861,036 A | 1/1999 | Godin |
| 5,868,141 A | 2/1999 | Ellias |
| 5,876,445 A | 3/1999 | Andersen |
| 5,887,594 A | 3/1999 | LoCicerolll |
| 5,891,845 A | 4/1999 | Myers |
| 5,922,019 A | 7/1999 | Hankh |
| 5,955,579 A | 9/1999 | Leonard et al. |
| 5,965,396 A | 10/1999 | Pan et al. |
| 5,993,483 A | 11/1999 | Gianotti |
| 6,027,508 A | 2/2000 | Ren |
| 6,048,351 A | 4/2000 | Gordon |
| 6,087,129 A | 7/2000 | Newgard et al. |
| 6,099,552 A | 8/2000 | Adams |
| 6,102,922 A | 8/2000 | Jakobsson |
| 6,113,609 A | 9/2000 | Adams |
| 6,117,911 A | 9/2000 | Grainger et al. |
| 6,132,471 A | 10/2000 | Johlin, Jr. |
| 6,146,416 A | 11/2000 | Andersen |
| 6,159,238 A | 12/2000 | Killion |
| 6,180,082 B1 | 1/2001 | Woltering et al. |
| 6,183,461 B1 | 2/2001 | Matsuura |
| 6,184,254 B1 | 2/2001 | Bukoski et al. |
| 6,200,336 B1 | 3/2001 | Pavcnik |
| 6,200,600 B1 | 3/2001 | Rashid |
| 6,241,738 B1 | 6/2001 | Dereume |
| 6,245,761 B1 | 6/2001 | Britton et al. |
| 6,251,132 B1 | 6/2001 | Ravenscroft |
| 6,254,642 B1 | 7/2001 | Taylor |
| 6,258,120 B1 | 7/2001 | McKenzie |
| 6,264,700 B1 | 7/2001 | Kilcoyne |
| 6,302,891 B1 | 10/2001 | Nadal |
| 6,302,917 B1 | 10/2001 | Dua |
| 6,303,637 B1 | 10/2001 | Bao et al. |
| 6,322,538 B1 | 11/2001 | Elbert |
| 6,331,190 B1 | 12/2001 | Shokoohi |
| 6,332,877 B1 | 12/2001 | Michels |
| 6,364,868 B1 | 4/2002 | Ikeguchi |
| 6,370,511 B1 | 4/2002 | Dang |
| 6,387,114 B2 | 5/2002 | Adams |
| 6,406,840 B1 | 6/2002 | Li et al. |
| 6,410,587 B1 | 6/2002 | Grainger et al. |
| 6,424,864 B1 | 7/2002 | Matsuura |
| 6,450,989 B2 | 9/2002 | Dubrul |
| 6,454,785 B2 | 9/2002 | DeHoyosGarza |
| 6,485,409 B1 | 11/2002 | Voloshin |
| 6,494,888 B1 | 12/2002 | Laufer et al. |
| 6,503,264 B1 | 1/2003 | Birk |
| 6,508,833 B2 | 1/2003 | Pavcnik |
| 6,524,335 B1 | 2/2003 | Hartley |
| 6,524,336 B1 | 2/2003 | Papazolgou |
| 6,530,951 B1 | 3/2003 | Bates |
| 6,531,491 B1 | 3/2003 | Kania et al. |
| 6,534,524 B1 | 3/2003 | Kania et al. |
| 6,537,247 B2 | 3/2003 | Shannon |
| 6,540,789 B1 | 4/2003 | Silverman |
| 6,544,291 B2 | 4/2003 | Taylor |
| 6,547,801 B1 | 4/2003 | Dargent |
| 6,558,400 B2 | 5/2003 | Deem |
| 6,558,429 B2 | 5/2003 | Taylor |
| 6,565,597 B1 | 5/2003 | Fearnot |

(56) References Cited

U.S. PATENT DOCUMENTS

| | | |
|---|---|---|
| 6,571,127 B1 | 5/2003 | Ben-Haim et al. |
| 6,572,627 B2 | 6/2003 | Gabbay |
| 6,572,629 B2 | 6/2003 | Kalloo |
| 6,575,896 B2 | 6/2003 | Silverman |
| 6,589,213 B2 | 7/2003 | Reydel |
| 6,589,275 B1 | 7/2003 | Ivancev |
| 6,596,023 B1 | 7/2003 | Nunez |
| 6,623,518 B2 | 9/2003 | Thompson |
| 6,630,123 B1 | 10/2003 | Woltering et al. |
| 6,635,079 B2 | 10/2003 | Unsworth |
| 6,656,194 B1 | 12/2003 | Gannoe |
| 6,663,639 B1 | 12/2003 | Laufer |
| 6,666,848 B2 | 12/2003 | Stone |
| 6,675,809 B2 | 1/2004 | Stack |
| 6,676,692 B2 | 1/2004 | Rabkin |
| 6,685,962 B2 | 2/2004 | Friedman |
| 6,695,875 B2 | 2/2004 | Stelter |
| 6,696,575 B2 | 2/2004 | Schmidt |
| 6,699,263 B2 | 3/2004 | Cope |
| 6,733,512 B2 | 5/2004 | McGhan |
| 6,734,208 B2 | 5/2004 | Grainger |
| 6,740,121 B2 | 5/2004 | Geitz |
| 6,743,198 B1 | 6/2004 | Tihon |
| 6,755,869 B2 | 6/2004 | Geitz |
| 6,761,733 B2 | 7/2004 | Chobotov |
| 6,764,518 B2 | 7/2004 | Godin |
| 6,773,440 B2 | 8/2004 | Gannoe |
| 6,773,441 B1 | 8/2004 | Laufer |
| 6,776,791 B1 | 8/2004 | Stallings |
| 6,776,999 B1 | 8/2004 | Krumme |
| 6,802,846 B2 | 10/2004 | Hauschild |
| 6,802,868 B2 | 10/2004 | Silverman |
| 6,844,349 B2 | 1/2005 | Kath |
| 6,845,776 B2 | 1/2005 | Stack |
| 6,855,153 B2 | 2/2005 | Saadat |
| 6,884,890 B2 | 4/2005 | Kania |
| 6,890,924 B2 | 5/2005 | Kath |
| 6,891,044 B2 | 5/2005 | Kania |
| 6,911,198 B2 | 6/2005 | Shachar |
| 6,932,838 B2 | 8/2005 | Schwartz |
| 6,939,370 B2 | 9/2005 | Hartley |
| 6,947,792 B2 | 9/2005 | Ben-Haim |
| 6,950,707 B2 | 9/2005 | Whitehurst |
| 6,994,095 B2 | 2/2006 | Burnett |
| 7,019,147 B1 | 3/2006 | Barth |
| 7,025,791 B2 | 4/2006 | Levine |
| 7,033,373 B2 | 4/2006 | delaTorre |
| 7,033,384 B2 | 4/2006 | Gannoe |
| 7,037,344 B2 | 5/2006 | Kagan |
| 7,041,120 B2 | 5/2006 | Li |
| 7,044,979 B2 | 5/2006 | Silverman |
| 7,056,305 B2 | 6/2006 | GarzaAlvarez |
| 7,060,080 B2 | 6/2006 | Bachmann |
| 7,063,860 B2 | 6/2006 | Chancellor |
| 7,066,945 B2 | 6/2006 | Hashiba |
| 7,071,337 B2 | 7/2006 | Kath |
| 7,083,629 B2 | 8/2006 | Weller |
| 7,084,171 B2 | 8/2006 | Grainger |
| 7,090,699 B2 | 8/2006 | Geitz |
| 7,097,665 B2 | 8/2006 | Stack |
| 7,111,627 B2 | 9/2006 | Stack |
| 7,120,497 B2 | 10/2006 | Ben-Halm |
| 7,121,283 B2 | 10/2006 | Stack |
| 7,122,058 B2 | 10/2006 | Levine |
| 7,128,750 B1 | 10/2006 | Stergiopulos |
| 7,141,581 B2 | 11/2006 | Bender |
| 7,141,587 B2 | 11/2006 | Kania |
| 7,145,008 B2 | 12/2006 | Kath |
| 7,146,984 B2 | 12/2006 | Stack |
| 7,148,380 B2 | 12/2006 | Wang |
| 7,152,607 B2 | 12/2006 | Stack |
| 7,153,314 B2 | 12/2006 | Laufer |
| 7,172,613 B2 | 2/2007 | Wazne |
| 7,159,750 B2 | 3/2007 | Assaf |
| 7,196,093 B2 | 3/2007 | Yuan |
| 7,208,499 B2 | 4/2007 | Kath |
| 7,211,114 B2 | 5/2007 | Bessler |
| 7,220,284 B2 | 5/2007 | Kagan |
| 7,221,978 B2 | 5/2007 | Ben-Haim |
| 7,230,098 B2 | 6/2007 | Cui |
| 7,235,562 B2 | 6/2007 | Kath |
| 7,238,191 B2 | 7/2007 | Bachmann |
| 7,267,694 B2 | 9/2007 | Levine |
| 7,271,262 B2 | 9/2007 | LaGreca |
| 7,273,451 B2 | 9/2007 | Sekine |
| 7,288,099 B2 | 10/2007 | Deem |
| 7,288,101 B2 | 10/2007 | Deem |
| 7,306,614 B2 | 12/2007 | Weller |
| 7,309,858 B2 | 12/2007 | Peppin |
| 7,314,443 B2 | 1/2008 | Jordan |
| 7,316,716 B2 | 1/2008 | Egan |
| 7,320,696 B2 | 1/2008 | Gazi |
| 7,329,285 B2 | 2/2008 | Levine |
| 7,330,747 B2 | 2/2008 | Maier |
| 7,330,753 B2 | 2/2008 | Policker |
| 7,332,493 B2 | 2/2008 | Kath |
| 7,332,513 B2 | 2/2008 | Assaf |
| 7,335,210 B2 | 2/2008 | Smit |
| 7,335,646 B2 | 2/2008 | Kieffer |
| 7,338,433 B2 | 3/2008 | Coe |
| 7,347,868 B2 | 3/2008 | Burnett |
| 7,347,875 B2 | 3/2008 | Levine |
| 7,354,454 B2 | 4/2008 | Stack |
| 7,364,591 B2 | 4/2008 | Silverman |
| 7,368,577 B2 | 5/2008 | Assaf |
| 7,371,862 B2 | 5/2008 | Vanotti |
| 7,410,988 B2 | 8/2008 | Dickson, Jr. |
| 7,416,885 B2 | 8/2008 | Freeman |
| 7,427,415 B2 | 9/2008 | Scharp |
| 7,435,739 B2 | 10/2008 | Chen |
| 7,462,487 B2 | 12/2008 | Tsao |
| 7,468,355 B2 | 12/2008 | Hamdi |
| 7,476,256 B2 | 1/2009 | Meade |
| 7,483,746 B2 | 1/2009 | Lee |
| 7,498,445 B2 | 3/2009 | Assaf |
| 7,503,922 B2 | 3/2009 | Deem |
| 7,510,559 B2 | 3/2009 | Deem |
| 7,511,070 B2 | 3/2009 | Grainger |
| 7,513,914 B2 | 4/2009 | Schurr |
| 7,530,985 B2 | 5/2009 | Takemoto |
| 7,547,312 B2 | 6/2009 | Bauman |
| 7,579,477 B2 | 8/2009 | Assaf |
| 7,582,313 B2 | 9/2009 | Faustman |
| 7,585,869 B2 | 9/2009 | Bhattacharya |
| 7,594,926 B2 | 9/2009 | Linder |
| 7,508,114 B2 | 10/2009 | Levine |
| 7,601,525 B2 | 10/2009 | Batich |
| 7,604,649 B2 | 10/2009 | McGuckin, Jr. |
| 7,520,454 B2 | 11/2009 | Dinsmoor |
| 7,620,560 B2 | 11/2009 | Dang |
| 7,625,939 B2 | 12/2009 | Heiser |
| 7,628,821 B2 | 12/2009 | Stack |
| 7,628,988 B2 | 12/2009 | Faustman |
| 7,637,905 B2 | 12/2009 | Saadat |
| 7,637,919 B2 | 12/2009 | Ishikawa |
| 7,654,951 B2 | 2/2010 | Ichikawa |
| 7,662,929 B2 | 2/2010 | Brown |
| 7,674,396 B2 | 3/2010 | Sterling |
| 7,674,457 B2 | 3/2010 | Borlongan |
| 7,678,068 B2 | 3/2010 | Levine |
| 7,682,330 B2 | 3/2010 | Meade |
| 7,691,152 B2 | 4/2010 | Silverman |
| 7,695,446 B2 | 4/2010 | Levine |
| 7,696,213 B2 | 4/2010 | Cheng |
| 7,699,863 B2 | 4/2010 | Marco |
| 7,725,333 B2 | 5/2010 | Dang |
| 7,727,143 B2 | 6/2010 | Birk |
| 7,731,757 B2 | 6/2010 | Taylor |
| 7,736,373 B2 | 6/2010 | Laufer |
| 7,741,336 B2 | 6/2010 | Kath |
| 7,742,818 B2 | 6/2010 | Dinsmoor |
| 7,749,254 B2 | 7/2010 | Sobelman |
| 7,758,535 B2 | 7/2010 | Levine |
| 7,765,008 B2 | 7/2010 | Ben-Haim |

(56) References Cited

U.S. PATENT DOCUMENTS

| | | |
|---|---|---|
| 7,766,861 B2 | 8/2010 | Levine |
| 7,766,973 B2 | 8/2010 | Levine |
| 7,771,382 B2 | 8/2010 | Levine |
| 7,774,216 B2 | 8/2010 | Dang |
| 7,780,590 B2 | 8/2010 | Birk |
| 7,794,447 B2 | 9/2010 | Dann |
| 7,795,290 B2 | 9/2010 | Dickson, Jr. |
| 7,798,954 B2 | 9/2010 | Birk |
| 7,799,088 B2 | 9/2010 | Geitz |
| 7,803,177 B2 | 9/2010 | Hartley |
| 7,803,195 B2 | 9/2010 | Levy |
| 7,811,298 B2 | 10/2010 | Birk |
| 7,811,299 B2 | 10/2010 | Bachmann |
| 7,815,589 B2 | 10/2010 | Meade |
| 7,815,591 B2 | 10/2010 | Levine |
| 7,819,836 B2 | 10/2010 | Levine |
| 7,833,280 B2 | 11/2010 | Stack |
| 7,837,643 B2 | 11/2010 | Levine |
| 7,837,669 B2 | 11/2010 | Dann |
| 7,838,524 B2 | 11/2010 | Lee |
| 7,840,269 B2 | 11/2010 | Policker |
| 7,846,138 B2 | 12/2010 | Dann |
| 7,850,704 B2 | 12/2010 | Burnett |
| 7,862,574 B2 | 1/2011 | Deem |
| 7,867,283 B2 | 1/2011 | Krueger |
| 7,881,797 B2 | 2/2011 | Griffin |
| 7,883,524 B2 | 2/2011 | Chen |
| 7,892,214 B2 | 2/2011 | Kagan |
| 7,892,827 B2 | 2/2011 | Matschiner |
| 7,901,419 B2 | 3/2011 | Bachmann |
| 7,909,838 B2 | 3/2011 | Deem |
| 7,922,684 B2 | 4/2011 | Weitzner |
| 7,928,109 B2 | 4/2011 | Luzzio |
| 7,935,073 B2 | 5/2011 | Levine |
| 7,945,323 B2 | 5/2011 | Jaax |
| 7,959,552 B2 | 6/2011 | Jordan |
| 7,959,640 B2 | 6/2011 | Kantsevoy |
| 7,960,345 B2 | 6/2011 | Kim |
| 7,966,071 B2 | 6/2011 | Ben-Haim |
| 7,968,575 B2 | 6/2011 | Assaf |
| 7,972,346 B2 | 7/2011 | Bachmann |
| 7,976,488 B2 | 7/2011 | Levine |
| 7,979,290 B2 | 7/2011 | Dang |
| 7,981,162 B2 | 7/2011 | Stack |
| 7,981,163 B2 | 7/2011 | Meade |
| 7,985,844 B2 | 7/2011 | Brown |
| 7,998,220 B2 | 8/2011 | Murphy |
| 7,998,966 B2 | 8/2011 | Bearss |
| 8,002,731 B2 | 8/2011 | Weitzner |
| 8,003,806 B2 | 8/2011 | Bloxham |
| 8,006,701 B2 | 8/2011 | Bilotti |
| 8,007,507 B2 | 8/2011 | Waller |
| 8,008,449 B2 | 8/2011 | Korman |
| 8,012,136 B2 | 9/2011 | Dann |
| 8,012,140 B1 | 9/2011 | Kagan |
| 8,012,162 B2 | 9/2011 | Bachmann |
| 8,012,966 B2 | 9/2011 | Tang |
| 8,021,693 B2 | 9/2011 | Faustman |
| 8,043,206 B2 | 10/2011 | Birk |
| 8,043,248 B2 | 10/2011 | Pasricha |
| 8,048,169 B2 | 11/2011 | Burnett |
| 8,048,170 B2 | 11/2011 | Silverman |
| 8,057,420 B2 | 11/2011 | Meade |
| 8,057,494 B2 | 11/2011 | Laufer |
| 8,062,656 B2 | 11/2011 | Oh-Lee |
| 8,066,689 B2 | 11/2011 | Mitelberg |
| 8,070,743 B2 | 12/2011 | Kagan |
| 8,070,824 B2 | 12/2011 | Burnett |
| 8,075,577 B2 | 12/2011 | Deem |
| 8,079,974 B2 | 12/2011 | Stergiopulos |
| 8,080,022 B2 | 12/2011 | Deem |
| 8,080,025 B2 | 12/2011 | Deem |
| 8,084,457 B2 | 12/2011 | Choidas |
| 8,084,484 B2 | 12/2011 | Frank |
| 8,092,482 B2 | 1/2012 | Gannoe |
| 8,095,219 B2 | 1/2012 | Lee |
| 8,096,966 B2 | 1/2012 | Levine |
| 8,105,392 B2 | 1/2012 | Durgin |
| 8,106,197 B2 | 1/2012 | Cui |
| 8,109,895 B2 | 2/2012 | Williams |
| 8,114,045 B2 | 2/2012 | Surti |
| 8,114,893 B2 | 2/2012 | Baell |
| 8,116,883 B2 | 2/2012 | Williams |
| 8,118,774 B2 | 2/2012 | Dann |
| 8,121,869 B2 | 2/2012 | Dang |
| 8,123,765 B2 | 2/2012 | Deem |
| 8,123,766 B2 | 2/2012 | Bauman |
| 8,123,767 B2 | 2/2012 | Bauman |
| 8,134,010 B2 | 3/2012 | Assaf |
| 8,137,301 B2 | 3/2012 | Levine |
| 8,137,662 B2 | 3/2012 | Freeman |
| 8,142,469 B2 | 3/2012 | Sosnowski |
| 8,142,514 B2 | 3/2012 | Geitz |
| 8,147,561 B2 | 4/2012 | Binrnoeller |
| 8,162,871 B2 | 4/2012 | Levine |
| 8,173,129 B2 | 5/2012 | Faustman |
| 8,177,853 B2 | 5/2012 | Stack |
| 8,182,441 B2 | 5/2012 | Swain |
| 8,182,459 B2 | 5/2012 | Dann |
| 8,182,543 B2 | 5/2012 | Schurr |
| 8,187,289 B2 | 5/2012 | Tacchino |
| 8,207,166 B2 | 6/2012 | Lee |
| 8,211,186 B2 | 7/2012 | Belhe |
| 8,216,266 B2 | 7/2012 | Hively |
| 8,216,268 B2 | 7/2012 | Hailer |
| 8,219,201 B2 | 7/2012 | Ben-Haim |
| 8,226,593 B2 | 7/2012 | Graham |
| 8,226,602 B2 | 7/2012 | Quijana |
| 8,232,273 B2 | 7/2012 | Baell |
| 8,236,023 B2 | 8/2012 | Birk |
| 8,247,411 B2 | 8/2012 | Luzzio |
| 8,252,816 B2 | 8/2012 | Frank |
| 8,268,821 B2 | 9/2012 | Nadeson |
| 8,273,755 B2 | 9/2012 | Cheng |
| 8,277,468 B2 | 10/2012 | Laufer |
| 8,282,598 B2 | 10/2012 | Belhe |
| 8,282,666 B2 | 10/2012 | Birk |
| 8,290,582 B2 | 10/2012 | Lin |
| 8,292,800 B2 | 10/2012 | Stone |
| 8,296,165 B2 | 10/2012 | Dang |
| 8,299,022 B2 | 10/2012 | Dong |
| 8,303,669 B2 | 11/2012 | Meade |
| 8,308,630 B2 | 11/2012 | Birk |
| 8,308,813 B2 | 11/2012 | Krueger |
| 8,317,677 B2 | 11/2012 | Bertolote |
| 8,323,180 B2 | 12/2012 | Birk |
| 8,323,229 B2 | 12/2012 | Shin |
| 8,334,263 B2 | 12/2012 | Nadeson |
| 8,337,567 B2 | 12/2012 | Stack |
| 8,337,829 B2 | 12/2012 | Freeman |
| 8,357,501 B2 | 1/2013 | Jackson |
| 8,362,251 B2 | 1/2013 | Tang |
| 8,366,602 B2 | 2/2013 | Birk |
| 8,376,929 B2 | 2/2013 | Birk |
| 8,377,081 B2 | 2/2013 | Bachmann |
| 8,382,780 B2 | 2/2013 | Birk |
| 8,398,654 B2 | 3/2013 | Franklin |
| 8,399,223 B2 | 3/2013 | Park |
| 8,403,877 B2 | 3/2013 | Priplata |
| 8,409,221 B2 | 4/2013 | Franklin |
| 8,409,226 B2 | 4/2013 | Kantsevoy |
| 8,414,559 B2 | 4/2013 | Gross |
| 8,425,451 B2 | 4/2013 | Levine |
| 8,430,894 B2 | 4/2013 | Brooks |
| 8,430,895 B2 | 4/2013 | Brooks |
| 8,431,597 B2 | 4/2013 | Munchhof |
| 8,436,011 B2 | 5/2013 | Bellevergue |
| 8,440,822 B2 | 5/2013 | Luzzio |
| 8,465,447 B2 | 6/2013 | Krueger |
| 8,470,815 B2 | 6/2013 | SaulnierSholler |
| 8,475,401 B2 | 7/2013 | Priplata |
| 8,486,153 B2 | 7/2013 | Levine |
| 8,491,472 B2 | 7/2013 | Mitelberg |
| 8,491,519 B2 | 7/2013 | Chin |

(56) References Cited

U.S. PATENT DOCUMENTS

| | | |
|---|---|---|
| 8,496,931 B2 | 7/2013 | Pogue |
| 8,506,517 B2 | 8/2013 | Stergiopulos |
| 8,506,532 B2 | 8/2013 | Olroyd |
| 8,507,274 B2 | 8/2013 | Melton |
| 8,515,542 B2 | 8/2013 | Jaax |
| 8,517,915 B2 | 8/2013 | Perron |
| 8,518,970 B2 | 8/2013 | Baell |
| 8,529,943 B2 | 9/2013 | Kliger |
| 8,556,918 B2 | 10/2013 | Bauman |
| 8,556,925 B2 | 10/2013 | Makower |
| 8,556,934 B2 | 10/2013 | Godin |
| 8,568,488 B2 | 10/2013 | Stack |
| 8,579,988 B2 | 11/2013 | Burnett |
| 8,585,628 B2 | 11/2013 | Harris |
| 8,585,753 B2 | 11/2013 | Scanlon |
| 8,585,771 B2 | 11/2013 | Binmoeller |
| 8,591,452 B2 | 11/2013 | Priplata |
| 8,591,533 B2 | 11/2013 | Needleman |
| 8,591,598 B2 | 11/2013 | Silverman |
| 8,597,224 B2 | 12/2013 | Vargas |
| 8,603,186 B2 | 12/2013 | Binmoelier |
| 8,613,749 B2 | 12/2013 | Deem |
| 8,623,893 B2 | 1/2014 | Lassalle |
| 8,628,554 B2 * | 1/2014 | Sharma ............ A61F 5/0036 606/191 |
| 8,628,583 B2 | 1/2014 | Meade |
| 8,633,204 B2 | 1/2014 | Cheng |
| 8,636,683 B2 | 1/2014 | Chin |
| 8,636,751 B2 | 1/2014 | Albrecht |
| 8,642,623 B2 | 2/2014 | Frank |
| 8,652,083 B2 | 2/2014 | Weitzner |
| 8,657,885 B2 | 2/2014 | Burnett |
| 8,663,301 B2 | 3/2014 | Riina |
| 8,663,338 B2 | 3/2014 | Burnett |
| 8,678,993 B2 | 3/2014 | Stroumpoulis |
| 8,679,137 B2 | 3/2014 | Bauman |
| 8,683,881 B2 | 4/2014 | Bouasaysy |
| 8,691,271 B2 | 4/2014 | Burnett |
| 8,698,373 B2 | 4/2014 | Augarten |
| 8,702,641 B2 | 4/2014 | Belhe |
| 8,702,642 B2 | 4/2014 | Belhe |
| 8,708,979 B2 | 4/2014 | Honaryar |
| 8,715,158 B2 | 5/2014 | Honaryar |
| 8,725,435 B2 | 5/2014 | Snow |
| 8,753,369 B2 | 6/2014 | Murature |
| 8,758,221 B2 | 6/2014 | Snow |
| 8,764,624 B2 | 7/2014 | Snow |
| 8,771,219 B2 | 7/2014 | Meade |
| 8,795,301 B2 | 8/2014 | Burnett |
| 8,801,597 B2 | 8/2014 | Franklin |
| 8,801,647 B2 | 8/2014 | Melanson |
| 8,808,270 B2 | 8/2014 | Dann |
| 8,821,373 B2 | 9/2014 | Schwab |
| 8,821,429 B2 | 9/2014 | Vargas |
| 8,821,430 B2 | 9/2014 | Stergiopulos |
| 8,821,521 B2 | 9/2014 | Burnett |
| 8,821,684 B2 | 9/2014 | Burnett |
| 8,834,405 B2 | 9/2014 | Meade |
| 8,834,553 B2 | 9/2014 | Melanson |
| 8,840,541 B2 | 9/2014 | Snow |
| 8,840,679 B2 | 9/2014 | Durgin |
| 8,840,952 B2 | 9/2014 | Ashby |
| 8,845,513 B2 | 9/2014 | Coe |
| 8,845,672 B2 | 9/2014 | Alverdy |
| 8,858,421 B2 | 10/2014 | Honaryar |
| 8,864,840 B2 | 10/2014 | Dominguez |
| 8,870,806 B2 | 10/2014 | Levine |
| 8,870,966 B2 | 10/2014 | Schwab |
| 8,876,694 B2 | 11/2014 | Honaryar |
| 8,882,655 B2 | 11/2014 | Nitka |
| 8,882,698 B2 | 11/2014 | Levine |
| 8,882,728 B2 | 11/2014 | Harders |
| 8,882,798 B2 | 11/2014 | Schwab |
| 8,888,732 B2 | 11/2014 | Raven |
| 8,888,797 B2 | 11/2014 | Burnett |
| 8,894,568 B2 | 11/2014 | Kwok |
| 8,900,117 B2 | 11/2014 | Birk |
| 8,900,118 B2 | 12/2014 | Birk |
| 8,905,915 B2 | 12/2014 | Birk |
| 8,905,916 B2 | 12/2014 | Jacobs |
| 8,920,358 B2 | 12/2014 | Levine |
| 8,920,447 B2 | 12/2014 | Dominguez |
| 8,932,247 B2 | 1/2015 | Stergiopulos |
| 8,939,888 B2 | 1/2015 | Augar ten |
| 8,956,318 B2 | 2/2015 | Miller |
| 8,956,380 B2 | 2/2015 | Dominguez |
| 8,961,393 B2 | 2/2015 | Rion |
| 8,961,394 B2 | 2/2015 | Honaryar |
| 8,968,177 B2 | 3/2015 | Silverman |
| 8,968,270 B2 | 3/2015 | Kagan |
| 8,979,735 B2 | 3/2015 | Augarten |
| 8,992,415 B2 | 3/2015 | Deuel |
| 8,992,559 B2 | 3/2015 | Weitzner |
| 9,017,358 B2 | 4/2015 | Schwab |
| 9,023,062 B2 | 5/2015 | Franklin |
| 9,023,063 B2 | 5/2015 | Franklin |
| 9,028,394 B2 | 5/2015 | Honaryar |
| 9,039,649 B2 | 5/2015 | Neisz |
| 9,044,298 B2 | 6/2015 | Franklin |
| 9,044,300 B2 | 6/2015 | Belhe |
| 9,050,165 B2 | 6/2015 | Perron |
| 9,050,168 B2 | 6/2015 | Neisz |
| 9,050,174 B2 | 6/2015 | Pecor |
| 9,060,844 B2 | 6/2015 | Kagan |
| 9,066,780 B2 | 6/2015 | Weber |
| 9,072,579 B2 | 7/2015 | Birk |
| 9,084,669 B2 | 7/2015 | Meade |
| 9,089,395 B2 | 7/2015 | Honaryar |
| 9,095,405 B2 | 8/2015 | Babkes |
| 9,095,416 B2 | 8/2015 | Meade |
| 9,526,648 B2 | 12/2016 | Sharma |
| 10,010,439 B2 | 7/2018 | Sharma et al. |
| 10,413,436 B2 | 9/2019 | Sharma |
| 10,420,665 B2 | 9/2019 | Sharma et al. |
| 10,512,557 B2 | 12/2019 | Sharma |
| 2001/0011543 A1 | 8/2001 | Forsell |
| 2002/0006962 A1 | 1/2002 | Wang |
| 2002/0071857 A1 | 6/2002 | Kararli |
| 2002/0091439 A1 | 7/2002 | Baker |
| 2002/0137086 A1 | 9/2002 | Olek |
| 2002/0143387 A1 | 10/2002 | Soetikno |
| 2002/0155100 A1 | 10/2002 | Kieffer |
| 2002/0165572 A1 | 11/2002 | Saadat |
| 2002/0165738 A1 | 11/2002 | Dang |
| 2002/0169165 A1 | 11/2002 | Kath |
| 2002/0173987 A1 | 11/2002 | Dang |
| 2002/0173988 A1 | 11/2002 | Dang |
| 2002/0173989 A1 | 11/2002 | Dang |
| 2002/0173992 A1 | 11/2002 | Dang |
| 2002/0183768 A1 | 12/2002 | Deem |
| 2002/0193816 A1 | 12/2002 | Laufer |
| 2002/0193828 A1 | 12/2002 | Griffin |
| 2002/0197656 A1 | 12/2002 | Li |
| 2003/0018299 A1 | 1/2003 | Stone |
| 2003/0040804 A1 | 2/2003 | Stack |
| 2003/0040808 A1 | 2/2003 | Stack |
| 2003/0050684 A1 | 3/2003 | Abrams |
| 2003/0053985 A1 | 3/2003 | Shachar |
| 2003/0055465 A1 | 3/2003 | Ben-Haim |
| 2003/0055466 A1 | 3/2003 | Ben-Haim |
| 2003/0055467 A1 | 3/2003 | Ben-Haim |
| 2003/0064970 A1 | 4/2003 | Grainger |
| 2003/0065359 A1 | 4/2003 | Weller |
| 2003/0066987 A1 | 4/2003 | Schmidt |
| 2003/0086975 A1 | 5/2003 | Ringeisen |
| 2003/0108597 A1 | 6/2003 | Chancellor |
| 2003/0109892 A1 | 6/2003 | Deem |
| 2003/0109935 A1 | 6/2003 | Geitz |
| 2003/0120265 A1 | 6/2003 | Deem |
| 2003/0153905 A1 | 8/2003 | Edwards |
| 2003/0158217 A1 | 8/2003 | Kath |
| 2003/0171261 A1 | 9/2003 | Livingston |
| 2003/0171386 A1 | 9/2003 | Connell |
| 2003/0190368 A1 | 10/2003 | Stoughton |

(56) References Cited

U.S. PATENT DOCUMENTS

| | | |
|---|---|---|
| 2003/0191476 A1 | 10/2003 | Smit |
| 2003/0191492 A1 | 10/2003 | Gellman |
| 2003/0199989 A1 | 10/2003 | Stack |
| 2003/0199990 A1 | 10/2003 | Stack |
| 2003/0199991 A1 | 10/2003 | Stack |
| 2003/0208260 A1 | 11/2003 | Lau |
| 2003/0232752 A1 | 12/2003 | Freeman |
| 2004/0024386 A1 | 2/2004 | Deem |
| 2004/0028658 A1 | 2/2004 | Faustman |
| 2004/0039350 A1 | 2/2004 | McKittrick |
| 2004/0039452 A1 | 2/2004 | Bessler |
| 2004/0045045 A1 | 3/2004 | Mather |
| 2004/0062778 A1 | 4/2004 | Shefer |
| 2004/0073278 A1 | 4/2004 | Pachys |
| 2004/0087876 A1 | 5/2004 | Eskuri |
| 2004/0092892 A1 | 5/2004 | Kagan |
| 2004/0097428 A1 | 5/2004 | Hamdi |
| 2004/0106892 A1 | 6/2004 | Stone |
| 2004/0107004 A1 | 6/2004 | Levine |
| 2004/0117031 A1 | 6/2004 | Stack |
| 2004/0122452 A1 | 6/2004 | Deem |
| 2004/0122453 A1 | 6/2004 | Deem |
| 2004/0122456 A1 | 6/2004 | Saadat |
| 2004/0127800 A1 | 7/2004 | Kimball |
| 2004/0133147 A1 | 7/2004 | Woo |
| 2004/0138529 A1 | 7/2004 | Wiltshire |
| 2004/0138760 A1 | 7/2004 | Schurr |
| 2004/0143342 A1 | 7/2004 | Stack |
| 2004/0147816 A1 | 7/2004 | Policker |
| 2004/0147871 A1 | 7/2004 | Burnett |
| 2004/0148034 A1 | 7/2004 | Kagan |
| 2004/0158331 A1 | 8/2004 | Stack |
| 2004/0170631 A1 | 9/2004 | Yacoby-Zeevi |
| 2004/0171634 A1 | 9/2004 | Kania |
| 2004/0172143 A1 | 9/2004 | Geitz |
| 2004/0180086 A1 | 9/2004 | Ramtoola |
| 2004/0181242 A1 | 9/2004 | Stack |
| 2004/0192598 A1 | 9/2004 | Kragie |
| 2004/0193184 A1 | 9/2004 | Laufer |
| 2004/0204429 A1 | 10/2004 | Yuan |
| 2004/0220177 A1 | 11/2004 | Kath |
| 2004/0220248 A1 | 11/2004 | Kania |
| 2004/0220682 A1 | 11/2004 | Levine |
| 2004/0225191 A1 | 11/2004 | Sekine |
| 2004/0236381 A1 | 11/2004 | Dinsrnoor |
| 2004/0236382 A1 | 11/2004 | Dinsmoor |
| 2004/0242604 A1 | 12/2004 | Bhattacharya |
| 2004/0243152 A1 | 12/2004 | Taylor |
| 2004/0254204 A1 | 12/2004 | Kath |
| 2005/0004430 A1 | 1/2005 | Lee |
| 2005/0004681 A1 | 1/2005 | Stack |
| 2005/0009840 A1 | 1/2005 | Cui |
| 2005/0020667 A1 | 1/2005 | Grainger |
| 2005/0037999 A1 | 2/2005 | LaGreca |
| 2005/0038097 A1 | 2/2005 | Bender |
| 2005/0055039 A1 | 3/2005 | Burnett |
| 2005/0075354 A1 | 4/2005 | Li |
| 2005/0085923 A1 | 4/2005 | Levine |
| 2005/0089577 A1 | 4/2005 | Yokoyama |
| 2005/0101011 A1 | 5/2005 | Tsao |
| 2005/0101618 A1 | 5/2005 | Connell |
| 2005/0124599 A1 | 6/2005 | Kath |
| 2005/0124662 A1 | 6/2005 | Kania |
| 2005/0125020 A1 | 6/2005 | Meade |
| 2005/0125075 A1 | 6/2005 | Meade |
| 2005/0130994 A1 | 6/2005 | Chen |
| 2005/0143765 A1 | 6/2005 | Bachmann |
| 2005/0143766 A1 | 6/2005 | Bachmann |
| 2005/0158288 A1 | 7/2005 | Faustman |
| 2005/0159435 A1 | 7/2005 | Kath |
| 2005/0159769 A1 | 7/2005 | Alverdy |
| 2005/0164388 A1 | 7/2005 | Son |
| 2005/0169902 A1 | 8/2005 | Borlongan |
| 2005/0171556 A1 | 8/2005 | Murphy |
| 2005/0192614 A1 | 9/2005 | Binmoeller |
| 2005/0196423 A1 | 9/2005 | Batich |
| 2005/0197714 A1 | 9/2005 | Sayet |
| 2005/0251182 A1 | 11/2005 | Bachmann |
| 2005/0256111 A1 | 11/2005 | Kath |
| 2005/0256125 A1 | 11/2005 | Kath |
| 2005/0256144 A1 | 11/2005 | Kath |
| 2005/0256587 A1 | 11/2005 | Egan |
| 2005/0267595 A1 | 12/2005 | Chen |
| 2005/0273060 A1 | 12/2005 | Levy |
| 2006/0002899 A1 | 1/2006 | Rice |
| 2006/0009858 A1 | 1/2006 | Levine |
| 2006/0015125 A1 | 1/2006 | Swain |
| 2006/0015151 A1 | 1/2006 | Aldrich |
| 2006/0020278 A1 | 1/2006 | Burnett |
| 2006/0025799 A1 | 2/2006 | Basu |
| 2006/0052416 A1 | 3/2006 | Dickson |
| 2006/0064120 A1 | 3/2006 | Levine |
| 2006/0069138 A1 | 3/2006 | Assaf |
| 2006/0069139 A1 | 3/2006 | Assaf |
| 2006/0069400 A1 | 3/2006 | Burnett |
| 2006/0074073 A1 | 4/2006 | Steinfeldt |
| 2006/0078993 A1 | 4/2006 | Phan |
| 2006/0084696 A1 | 4/2006 | Grainger |
| 2006/0089571 A1 | 4/2006 | Gertner |
| 2006/0089627 A1 | 4/2006 | Burnett |
| 2006/0105454 A1 | 5/2006 | Son |
| 2006/0116383 A1 | 6/2006 | Bloxham |
| 2006/0127437 A1 | 6/2006 | Kennedy |
| 2006/0134109 A1 | 6/2006 | Gaitanaris |
| 2006/0134186 A1 | 6/2006 | Carlton |
| 2006/0142731 A1 | 6/2006 | Brooks |
| 2006/0142787 A1 | 6/2006 | Weller |
| 2006/0161187 A1 | 7/2006 | Levine |
| 2006/0161265 A1 | 7/2006 | Levine |
| 2006/0183718 A1 | 8/2006 | Assaf |
| 2006/0183912 A1 | 8/2006 | Assaf |
| 2006/0183913 A1 | 8/2006 | Assaf |
| 2006/0228775 A1 | 10/2006 | Collier |
| 2006/0241130 A1 | 10/2006 | Keinan |
| 2006/0241748 A1 | 10/2006 | Lee |
| 2006/0271088 A1 | 11/2006 | Alfrhan |
| 2006/0276713 A1 | 12/2006 | Maier |
| 2007/0003610 A1 | 1/2007 | Chancellor |
| 2007/0021382 A1 | 1/2007 | Assaf |
| 2007/0021988 A1 | 1/2007 | Dang |
| 2007/0027548 A1 | 2/2007 | Levine |
| 2007/0032879 A1 | 2/2007 | Levine |
| 2007/0037883 A1 | 2/2007 | Dusting |
| 2007/0060940 A1 | 3/2007 | Brazzini |
| 2007/0072874 A1 | 3/2007 | Cui |
| 2007/0072885 A1 | 3/2007 | Bhattacharya |
| 2007/0078435 A1 | 4/2007 | Stone |
| 2007/0083224 A1 | 4/2007 | Hively |
| 2007/0083271 A1 | 4/2007 | Levine |
| 2007/0088389 A1 | 4/2007 | Dunkin |
| 2007/0100367 A1 | 5/2007 | Quijano |
| 2007/0100368 A1 | 5/2007 | Quijano |
| 2007/0104754 A1 | 5/2007 | Sterling |
| 2007/0105861 A1 | 5/2007 | Lee |
| 2007/0112020 A1 | 5/2007 | Vanotti |
| 2007/0118158 A1 | 5/2007 | Deem |
| 2007/0118159 A1 | 5/2007 | Deem |
| 2007/0118168 A1 | 5/2007 | Lointier |
| 2007/0135335 A1 | 6/2007 | Collier |
| 2007/0135825 A1 | 6/2007 | Binmoeller |
| 2007/0135829 A1 | 6/2007 | Paganon |
| 2007/0135831 A1 | 6/2007 | Burnett |
| 2007/0148129 A1 | 6/2007 | Shortman |
| 2007/0149994 A1 | 6/2007 | Sosnowski |
| 2007/0156248 A1 | 7/2007 | Marco |
| 2007/0167963 A1 | 7/2007 | Deem |
| 2007/0173881 A1 | 7/2007 | Birk |
| 2007/0178160 A1 | 8/2007 | Burnett |
| 2007/0185176 A1 | 8/2007 | VanGelder |
| 2007/0185540 A1 | 8/2007 | Ben-Haim |
| 2007/0191344 A1 | 8/2007 | Choidas |
| 2007/0198039 A1 | 8/2007 | Jones |
| 2007/0198074 A1 | 8/2007 | Dann |
| 2007/0207186 A1 | 9/2007 | Scanlon |

(56) References Cited

U.S. PATENT DOCUMENTS

| | | |
|---|---|---|
| 2007/0210018 A1 | 9/2007 | Wallwiener |
| 2007/0213740 A1 | 9/2007 | Deem |
| 2007/0213748 A1 | 9/2007 | Deem |
| 2007/0219570 A1 | 9/2007 | Deem |
| 2007/0250083 A1 | 10/2007 | Deem |
| 2007/0250132 A1 | 10/2007 | Burnett |
| 2007/0255379 A1 | 11/2007 | Williams |
| 2007/0265598 A1 | 11/2007 | Karasik |
| 2007/0265709 A1 | 11/2007 | Rajan |
| 2007/0275902 A1 | 11/2007 | Gonda |
| 2007/0275962 A1 | 11/2007 | Koul |
| 2007/0276428 A1 | 11/2007 | Haller |
| 2007/0282349 A1 | 12/2007 | Deem |
| 2007/0282452 A1 | 12/2007 | Weitzner |
| 2007/0282453 A1 | 12/2007 | Weitzner |
| 2007/0286856 A1 | 12/2007 | Brown |
| 2007/0293885 A1 | 12/2007 | Binmoeller |
| 2007/0299320 A1 | 12/2007 | Policker |
| 2008/0021742 A1 | 1/2008 | Dang |
| 2008/0026072 A1 | 1/2008 | Nakayama |
| 2008/0027469 A1 | 1/2008 | Bachmann |
| 2008/0039463 A1 | 2/2008 | Nadeson |
| 2008/0051849 A1 | 2/2008 | Ben-Haim |
| 2008/0058887 A1 | 3/2008 | Griffin |
| 2008/0058889 A1 | 3/2008 | Ben-Haim |
| 2008/0058891 A1 | 3/2008 | Ben-Haim |
| 2008/0059231 A1 | 3/2008 | Dang |
| 2008/0065136 A1 | 3/2008 | Young |
| 2008/0065421 A1 | 3/2008 | Dang |
| 2008/0071383 A1 | 3/2008 | Levine |
| 2008/0090801 A1 | 4/2008 | Cheng |
| 2008/0097466 A1 | 4/2008 | Levine |
| 2008/0097513 A1 | 4/2008 | Kaji |
| 2008/0097788 A1 | 4/2008 | Dang |
| 2008/0120734 A1 | 5/2008 | Kieffer |
| 2008/0154129 A1 | 6/2008 | Mizunuma |
| 2008/0161838 A1 | 7/2008 | DArcangelo |
| 2008/0175828 A1 | 7/2008 | Freeman |
| 2008/0187575 A1 | 8/2008 | Klebl |
| 2008/0194574 A1 | 8/2008 | Eikhoff |
| 2008/0194596 A1 | 8/2008 | Letrent |
| 2008/0195226 A1 | 8/2008 | Williams |
| 2008/0207677 A1 | 8/2008 | Muller |
| 2008/0208241 A1 | 8/2008 | Weiner |
| 2008/0208355 A1 | 8/2008 | Stack |
| 2008/0208356 A1 | 8/2008 | Stack |
| 2008/0208357 A1 | 8/2008 | Melanson |
| 2008/0214545 A1 | 9/2008 | Lee |
| 2008/0221595 A1 | 9/2008 | Surti |
| 2008/0228030 A1 | 9/2008 | Godin |
| 2008/0228066 A1 | 9/2008 | Waitzman |
| 2008/0233163 A1 | 9/2008 | Assaf |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0243167 A1 | 10/2008 | Paganon |
| 2008/0249533 A1 | 10/2008 | Godin |
| 2008/0249635 A1 | 10/2008 | Weitzner |
| 2008/0255587 A1* | 10/2008 | Cully ................ A61F 2/04 606/139 |
| 2008/0255594 A1 | 10/2008 | Cully |
| 2008/0255678 A1 | 10/2008 | Cully |
| 2008/0260797 A1 | 10/2008 | Oh-Lee |
| 2008/0261258 A1 | 10/2008 | Smith |
| 2008/0262529 A1 | 10/2008 | Jacques |
| 2008/0269289 A1 | 10/2008 | Frank |
| 2008/0269555 A1 | 10/2008 | Paganon |
| 2008/0281257 A1 | 11/2008 | Waller |
| 2008/0281375 A1 | 11/2008 | Chen |
| 2008/0293618 A1 | 11/2008 | Heiser |
| 2008/0293733 A1 | 11/2008 | Bearss |
| 2008/0300234 A1 | 12/2008 | Kath |
| 2008/0302855 A1 | 12/2008 | Bilotti |
| 2008/0319471 A1 | 12/2008 | Sosnowski et al. |
| 2009/0005867 A1 | 1/2009 | Lefranc |
| 2009/0012544 A1 | 1/2009 | Thompson |
| 2009/0042785 A1 | 2/2009 | Matschiner |
| 2009/0048313 A1 | 2/2009 | Dickson |
| 2009/0053182 A1 | 2/2009 | Ichim |
| 2009/0054395 A1 | 2/2009 | Luzzio |
| 2009/0062401 A1 | 3/2009 | Odermatt |
| 2009/0088676 A1 | 4/2009 | Murata |
| 2009/0093839 A1 | 4/2009 | Kelleher |
| 2009/0105562 A1 | 4/2009 | Chiou |
| 2009/0111805 A1 | 4/2009 | Morris |
| 2009/0138094 A1 | 5/2009 | Schurr |
| 2009/0142413 A1 | 6/2009 | Allen |
| 2009/0149849 A1 | 6/2009 | Lin |
| 2009/0156590 A1 | 6/2009 | Frank |
| 2009/0164028 A1 | 6/2009 | Chen |
| 2009/0171383 A1 | 7/2009 | Cole |
| 2009/0178153 A1 | 7/2009 | Gaitanaris |
| 2009/0182303 A1 | 7/2009 | Walak |
| 2009/0182424 A1 | 7/2009 | Marco |
| 2009/0187197 A1 | 7/2009 | Roeber et al. |
| 2009/0187200 A1 | 7/2009 | Burnett |
| 2009/0187201 A1 | 7/2009 | Burnett |
| 2009/0196912 A1 | 8/2009 | Eickhoff |
| 2009/0198254 A1 | 8/2009 | Laufer |
| 2009/0214474 A1 | 8/2009 | Jennings |
| 2009/0216262 A1 | 8/2009 | Burnett |
| 2009/0217401 A1 | 8/2009 | Korman |
| 2009/0226907 A1 | 9/2009 | Nice |
| 2009/0227641 A1 | 9/2009 | Bhattacharya |
| 2009/0259240 A1 | 10/2009 | Graham |
| 2009/0264345 A1 | 10/2009 | McAlpine |
| 2009/0275511 A1 | 11/2009 | Dong |
| 2009/0276055 A1 | 11/2009 | Harris |
| 2009/0287231 A1 | 11/2009 | Brooks |
| 2009/0299486 A1 | 12/2009 | Shohat |
| 2009/0299487 A1 | 12/2009 | Stack |
| 2009/0306186 A1 | 12/2009 | Jackson |
| 2009/0317374 A1 | 12/2009 | Park |
| 2010/0004239 A1 | 1/2010 | Tang |
| 2010/0016353 A1 | 1/2010 | Henne |
| 2010/0029615 A1 | 2/2010 | Munchhof |
| 2010/0036481 A1 | 2/2010 | Dubrul |
| 2010/0048471 A1 | 2/2010 | Kim |
| 2010/0049224 A1 | 2/2010 | Vargas |
| 2010/0068177 A1 | 3/2010 | Faustman |
| 2010/0114150 A1 | 5/2010 | Magal |
| 2010/0121371 A1 | 5/2010 | Brooks |
| 2010/0136114 A1 | 6/2010 | Mao |
| 2010/0137279 A1 | 6/2010 | Cheng |
| 2010/0145301 A1 | 6/2010 | Magal |
| 2010/0150893 A1 | 6/2010 | Faustman |
| 2010/0152765 A1 | 6/2010 | Haley |
| 2010/0158896 A1 | 6/2010 | Brown |
| 2010/0158902 A1 | 6/2010 | Pogue |
| 2010/0168563 A1 | 7/2010 | Braver |
| 2010/0179584 A1 | 7/2010 | Carpenter |
| 2010/0190782 A1 | 7/2010 | Baell |
| 2010/0204093 A1 | 8/2010 | Kaushal |
| 2010/0204221 A1 | 8/2010 | Vankayalapati |
| 2010/0204688 A1 | 8/2010 | Hoey |
| 2010/0209488 A1 | 8/2010 | Wrasidlo |
| 2010/0210622 A1 | 8/2010 | Baell |
| 2010/0221233 A1 | 9/2010 | Borlongan |
| 2010/0222381 A1 | 9/2010 | Vankayalapati |
| 2010/0234435 A1 | 9/2010 | Bhattacharya |
| 2010/0234886 A1 | 9/2010 | Godin |
| 2010/0235197 A1 | 9/2010 | Dang |
| 2010/0247691 A1 | 9/2010 | Kim |
| 2010/0249822 A1 | 9/2010 | Nihalani |
| 2010/0249825 A1 | 9/2010 | Nihalani |
| 2010/0255087 A1 | 10/2010 | Coulter |
| 2010/0256654 A1 | 10/2010 | Pasricha |
| 2010/0256775 A1 | 10/2010 | Belhe |
| 2010/0261162 A1 | 10/2010 | Nice |
| 2010/0266675 A1 | 10/2010 | Gerwick |
| 2010/0268260 A1 | 10/2010 | Riina |
| 2010/0286628 A1 | 11/2010 | Gross |
| 2010/0286660 A1 | 11/2010 | Gross |

(56) References Cited

U.S. PATENT DOCUMENTS

| | | |
|---|---|---|
| 2010/0298631 A1 | 11/2010 | Stack |
| 2010/0298741 A1 | 11/2010 | Gross |
| 2010/0305590 A1 | 12/2010 | Holmes |
| 2010/0324572 A1 | 12/2010 | Needleman |
| 2010/0324928 A1 | 12/2010 | Dang |
| 2011/0004146 A1 | 1/2011 | Priplata |
| 2011/0004320 A1 | 1/2011 | Priplata |
| 2011/0009801 A1 | 1/2011 | Blaeser |
| 2011/0040230 A1 | 2/2011 | Laufer |
| 2011/0040232 A1 | 2/2011 | Magal |
| 2011/0066175 A1 | 3/2011 | Gross |
| 2011/0068143 A1 | 3/2011 | Laufer |
| 2011/0082535 A1 | 4/2011 | Shin |
| 2011/0092482 A1 | 4/2011 | Nadeson |
| 2011/0097280 A1 | 4/2011 | Dees |
| 2011/0098730 A1 | 4/2011 | Kelleher |
| 2011/0118650 A1 | 5/2011 | Nihalani |
| 2011/0124643 A1 | 5/2011 | Bellevergue |
| 2011/0125211 A1 | 5/2011 | Griffin |
| 2011/0130775 A1 | 6/2011 | Tacchino |
| 2011/0136809 A1 | 6/2011 | Lee |
| 2011/0137428 A1 | 6/2011 | Terliuc |
| 2011/0142905 A1 | 6/2011 | Bar-Shalom |
| 2011/0152608 A1 | 6/2011 | Bachmann |
| 2011/0152899 A1 | 6/2011 | Deem |
| 2011/0166120 A1 | 7/2011 | Luzzio |
| 2011/0172585 A1 | 7/2011 | Weitzner |
| 2011/0185439 A1 | 7/2011 | Gaitanaris |
| 2011/0190905 A1 | 8/2011 | Behan |
| 2011/0206760 A1 | 8/2011 | Kliger |
| 2011/0213469 A1 | 9/2011 | Chin |
| 2011/0214189 A1 | 9/2011 | Gaitanar Is |
| 2011/0218143 A1 | 9/2011 | Kaushal |
| 2011/0218563 A1 | 9/2011 | Brooks |
| 2011/0245752 A1 | 10/2011 | Levine |
| 2011/0256123 A1 | 10/2011 | Ilan |
| 2011/0257580 A1 | 10/2011 | Meade |
| 2011/0263504 A1 | 10/2011 | Cerami |
| 2011/0269772 A1 | 11/2011 | Bearss |
| 2011/0270405 A1 | 11/2011 | Geitz |
| 2011/0270410 A1 | 11/2011 | Stack |
| 2011/0275891 A1 | 11/2011 | Shemi |
| 2011/0276091 A1 | 11/2011 | Melanson |
| 2011/0288080 A1 | 11/2011 | SaulnierSholler |
| 2011/0295054 A1 | 12/2011 | Aldridge |
| 2011/0295055 A1 | 12/2011 | Albrecht |
| 2011/0295151 A1 | 12/2011 | Bakos |
| 2011/0295286 A1 | 12/2011 | Harris |
| 2011/0301156 A1 | 12/2011 | Frank |
| 2011/0301353 A1 | 12/2011 | Tang |
| 2011/0307075 A1 | 12/2011 | Sharma |
| 2011/0320219 A1 | 12/2011 | Dang |
| 2012/0003204 A1 | 1/2012 | Park |
| 2012/0003634 A1 | 1/2012 | Fr Umkin |
| 2012/0004676 A1 | 1/2012 | Vargas |
| 2012/0029550 A1 | 2/2012 | Forsell |
| 2012/0041465 A1 | 2/2012 | Shalon |
| 2012/0046718 A1 | 2/2012 | Singh |
| 2012/0058107 A1 | 3/2012 | Tang |
| 2012/0059431 A1 | 3/2012 | Williams |
| 2012/0065571 A1 | 3/2012 | Thompson |
| 2012/0083819 A1 | 4/2012 | Wang |
| 2012/0087910 A1 | 4/2012 | Trieu |
| 2012/0088300 A1 | 4/2012 | Melton |
| 2012/0088967 A1 | 4/2012 | Laufer |
| 2012/0089170 A1 | 4/2012 | Dominguez |
| 2012/0095384 A1 | 4/2012 | Babkes |
| 2012/0095385 A1 | 4/2012 | Dominguez |
| 2012/0095483 A1 | 4/2012 | Babkes |
| 2012/0095494 A1 | 4/2012 | Dominguez |
| 2012/0095495 A1 | 4/2012 | Babkes et al. |
| 2012/0095497 A1 | 4/2012 | Babkes |
| 2012/0108590 A1 | 5/2012 | Birtalan |
| 2012/0110682 A1 | 5/2012 | Mather |
| 2012/0116286 A1 | 5/2012 | Williams |
| 2012/0121594 A1 | 5/2012 | Smith |
| 2012/0142760 A1 | 6/2012 | Kieffer |
| 2012/0148540 A1 | 6/2012 | Freeman |
| 2012/0157470 A1 | 6/2012 | Catron |
| 2012/0157495 A1 | 6/2012 | Munchhof |
| 2012/0158026 A1 | 6/2012 | Behan |
| 2012/0179086 A1 | 7/2012 | Shank |
| 2012/0184541 A1 | 7/2012 | Baell |
| 2012/0184893 A1 | 7/2012 | Thompson |
| 2012/0184967 A1 | 7/2012 | Levine |
| 2012/0208786 A1 | 8/2012 | Lyles |
| 2012/0209400 A1 | 8/2012 | Schurr |
| 2012/0213731 A1 | 8/2012 | Faustman |
| 2012/0214848 A1 | 8/2012 | Zhang |
| 2012/0215152 A1 | 8/2012 | Levine |
| 2012/0232460 A1 | 9/2012 | Raven |
| 2012/0232577 A1 | 9/2012 | Birk |
| 2012/0245087 A1 | 9/2012 | Jackson |
| 2012/0245553 A1 | 9/2012 | Raven |
| 2012/0253259 A1 | 10/2012 | Belhe |
| 2012/0253260 A1 | 10/2012 | Belhe |
| 2012/0253529 A1 | 10/2012 | Carlson |
| 2012/0258126 A1 | 10/2012 | Scholler |
| 2012/0263781 A1 | 10/2012 | Chancellor |
| 2012/0271217 A1 | 10/2012 | Stack |
| 2012/0029635 A1 | 11/2012 | Nguyen |
| 2012/0277210 A1 | 11/2012 | Catron |
| 2012/0277271 A1 | 11/2012 | Nadeson |
| 2012/0296365 A1 | 11/2012 | Nguyen |
| 2012/0301475 A1 | 11/2012 | Shemesh |
| 2012/0302602 A1 | 11/2012 | Frank |
| 2012/0309775 A1 | 12/2012 | Cheng |
| 2013/0005724 A1 | 1/2013 | Lassalle |
| 2013/0005964 A1 | 1/2013 | Luzzio |
| 2013/0006382 A1 | 1/2013 | Behan |
| 2013/0006672 A1 | 1/2013 | Dang |
| 2013/0011332 A1 | 1/2013 | Boyden |
| 2013/0013084 A1 | 1/2013 | Birk |
| 2013/0030350 A1 | 1/2013 | Albrecht |
| 2013/0030351 A1 | 1/2013 | Belhe |
| 2013/0034844 A1 | 2/2013 | Boyle |
| 2013/0035576 A1 | 2/2013 | OGrady |
| 2013/0041424 A1 | 2/2013 | Neisz |
| 2013/0071466 A1 | 3/2013 | Chancellor |
| 2013/0079329 A1 | 3/2013 | Hood |
| 2013/0079345 A1 | 3/2013 | Eickhoff |
| 2013/0079603 A1 | 3/2013 | Vargas |
| 2013/0133091 A1 | 5/2013 | Korman |
| 2013/0156726 A1 | 6/2013 | Ichim |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0177527 A1 | 7/2013 | Imran |
| 2013/0177550 A1 | 7/2013 | Imran |
| 2013/0178472 A1 | 7/2013 | Bellevergue |
| 2013/0189240 A1 | 7/2013 | Cho |
| 2013/0189353 A1 | 7/2013 | Imran |
| 2013/0190675 A1 | 7/2013 | Sandoski |
| 2013/0195970 A1 | 8/2013 | Imran |
| 2013/0197421 A1 | 8/2013 | Sharvit |
| 2013/0204208 A1 | 8/2013 | Olson |
| 2013/0210800 A1 | 8/2013 | Nair |
| 2013/0218289 A1 | 8/2013 | Gao |
| 2013/0245068 A1 | 9/2013 | Kwon |
| 2013/0247233 A1 | 9/2013 | Gaitanaris |
| 2013/0253408 A1 | 9/2013 | Krueger |
| 2013/0273061 A1 | 10/2013 | Huang |
| 2013/0274659 A1 | 10/2013 | Imran |
| 2013/0274789 A1 | 10/2013 | Brooks |
| 2013/0281911 A1 | 10/2013 | Babkes |

(56) References Cited

U.S. PATENT DOCUMENTS

| | | |
|---|---|---|
| 2013/0289139 A1 | 10/2013 | Radford |
| 2013/0289466 A1 | 10/2013 | Babkes |
| 2013/0296764 A1 | 11/2013 | Stack |
| 2013/0296913 A1 | 11/2013 | Foote |
| 2013/0310727 A1 | 11/2013 | Stack |
| 2013/0310833 A1 | 11/2013 | Brown |
| 2013/0324902 A1 | 12/2013 | Miller |
| 2013/0324906 A1 | 12/2013 | Neisz |
| 2013/0324907 A1 | 12/2013 | Huntley |
| 2013/0331359 A1 | 12/2013 | Yun |
| 2013/0331383 A1 | 12/2013 | SaulnierSholler |
| 2013/0331759 A1 | 12/2013 | Neisz |
| 2013/0337563 A1 | 12/2013 | Phan |
| 2013/0338741 A1 | 12/2013 | Singh |
| 2013/0344173 A1 | 12/2013 | Fogelman |
| 2013/0345670 A1 | 12/2013 | Rajagopalan |
| 2014/0004175 A1 | 1/2014 | Kliger |
| 2014/0005190 A1 | 1/2014 | Baell |
| 2014/0018719 A1 | 1/2014 | Chamorro |
| 2014/0024114 A1 | 1/2014 | Melton |
| 2014/0024991 A1 | 1/2014 | Chin |
| 2014/0039250 A1 | 2/2014 | Bachmann |
| 2014/0044641 A1 | 2/2014 | Toporik |
| 2014/0044736 A1 | 2/2014 | Hammers |
| 2014/0045815 A1 | 2/2014 | Hood |
| 2014/0051645 A1 | 2/2014 | Matschiner |
| 2014/0081416 A1 | 3/2014 | Clerc |
| 2014/0094734 A1 | 4/2014 | Stack |
| 2014/0121585 A1 | 5/2014 | Baker |
| 2014/0142720 A1 | 5/2014 | Stack |
| 2014/0180188 A1 | 6/2014 | Chin |
| 2014/0180192 A1 | 6/2014 | Ortiz |
| 2014/0194806 A1 | 7/2014 | Belhe |
| 2014/0194917 A1 | 7/2014 | Sharma |
| 2014/0200502 A1 | 7/2014 | Belhe |
| 2014/0213960 A1 | 7/2014 | Belhe |
| 2014/0221899 A1 | 8/2014 | Vargas |
| 2014/0243992 A1 | 8/2014 | Walsh |
| 2014/0276336 A1 | 9/2014 | Sharma |
| 2015/0196412 A1 | 7/2015 | Roselauf |
| 2015/0196419 A1* | 7/2015 | Roselauf ............... A61F 5/0079 604/8 |
| 2016/0095733 A1 | 4/2016 | Sharma et al. |
| 2018/0263803 A1 | 9/2018 | Sharma et al. |
| 2019/0365552 A1 | 12/2019 | Sharma |

FOREIGN PATENT DOCUMENTS

| | | |
|---|---|---|
| AU | 2012211067 A1 | 8/2013 |
| AU | 2010232570 B2 | 11/2013 |
| AU | 2014200766 A1 | 3/2014 |
| AU | 2012315575 A1 | 4/2014 |
| CA | 2756991 A1 | 10/2010 |
| CN | 1575155 A | 2/2005 |
| CN | 1713870 A | 12/2005 |
| CN | 2756991 Y | 2/2006 |
| CN | 102387762 A | 3/2012 |
| CN | 102470038 A | 5/2012 |
| CN | 103635212 A | 3/2014 |
| EP | 0278937 | 10/1993 |
| EP | 0480667 B1 | 3/1996 |
| EP | 0774571 A1 | 5/1997 |
| EP | 0754017 | 6/2002 |
| EP | 0843538 | 6/2002 |
| EP | 1420730 A2 | 5/2004 |
| EP | 1492477 A1 | 1/2005 |
| EP | 1492478 A1 | 1/2005 |
| EP | 2451411 A2 | 5/2012 |
| EP | 2521513 A1 | 11/2012 |
| EP | 2667910 A2 | 12/2013 |
| EP | 2413849 B1 | 7/2014 |
| EP | 2760502 A1 | 8/2014 |
| JP | H04-212348 | 8/1992 |
| JP | 2005-500127 A | 1/2005 |
| JP | 2010-523262 A | 7/2010 |
| JP | 2011-152425 A | 8/2011 |
| JP | 2012-522595 A | 9/2012 |
| KR | 2012-0008492 A | 1/2012 |
| WO | WO1988000027 | 1/1988 |
| WO | WO1991001117 | 2/1991 |
| WO | WO1994001165 | 1/1994 |
| WO | WO0012027 | 3/2000 |
| WO | 00/32137 A1 | 6/2000 |
| WO | WO0042949 | 7/2000 |
| WO | WO0145485 | 6/2001 |
| WO | WO2001049359 | 7/2001 |
| WO | 02/96327 A2 | 12/2002 |
| WO | 03/17882 A2 | 3/2003 |
| WO | 03/86246 A1 | 10/2003 |
| WO | WO03086247 | 10/2003 |
| WO | WO03086360 | 10/2003 |
| WO | 03/94785 A1 | 11/2003 |
| WO | WO03094784 | 11/2003 |
| WO | 2004/049982 A2 | 6/2004 |
| WO | 2004/064685 A1 | 8/2004 |
| WO | WO2004064680 | 8/2004 |
| WO | WO2004069331 | 8/2004 |
| WO | WO2004069332 | 8/2004 |
| WO | 2004/087014 A2 | 10/2004 |
| WO | WO2004087233 | 10/2004 |
| WO | WO2006064503 | 6/2006 |
| WO | WO2007007339 | 1/2007 |
| WO | WO2007072469 | 6/2007 |
| WO | WO2008023374 | 2/2008 |
| WO | 2008/112894 A1 | 9/2008 |
| WO | 2008/121409 A1 | 10/2008 |
| WO | 2008/121831 A1 | 10/2008 |
| WO | 2008/154450 A1 | 12/2008 |
| WO | 2010/115011 A1 | 10/2010 |
| WO | 2010/128495 A1 | 11/2010 |
| WO | 2011/006098 A2 | 1/2011 |
| WO | WO2011085234 | 7/2011 |
| WO | WO2011159271 | 12/2011 |
| WO | WO2012068377 | 5/2012 |
| WO | WO2012103531 | 8/2012 |
| WO | WO2013049779 | 4/2013 |
| WO | 2014/113483 A1 | 7/2014 |
| WO | WO2014153267 | 9/2014 |
| WO | 2015/071496 A1 | 5/2015 |
| WO | WO2016049149 | 3/2016 |
| WO | 2017/013266 A1 | 1/2017 |
| WO | WO2017132676 | 8/2017 |

OTHER PUBLICATIONS

International Preliminary Report on Patentability received for PCT Patent Application No. PCT/US2014/029846, dated Sep. 24, 2015, 16 pages.

International Preliminary Report on Patentability received for PCT Patent Application No. PCT/US2015/051668, dated Apr. 6, 2017, 10 pages.

International Preliminary Report on Patentability received for PCT Patent Application No. PCT/US2016/028509, dated Apr. 5, 2018, 7 pages.

International Preliminary Report on Patentability received for PCT Patent Application No. PCT/US2017/029571, dated Nov. 8, 2018, 12 pages.

International Search Report and Written Opinion received for PCT Patent Application No. PCT/US2016/028509, dated Aug. 12, 2016, 8 pages.

International Search Report for PCT/US2014/029846, dated Apr. 2, 2015.

International Search Report for PCT/US2015/051668, dated Apr. 19, 2016.

International Written Opinion received for PCT Patent Application No. PCT/US2014/029846, dated Apr. 2, 2015, 14 pages.

International Written Opinion received for PCT Patent Application No. PCT/US2015/051668, dated Apr. 19, 2016, 8 pages.

International Written Opinion received for PCT Patent Application No. PCT/US2017/029571, dated Sep. 11, 2017, 10 pages.

(56) References Cited

OTHER PUBLICATIONS

Klausner et al., "Expandable gastroretentive dosage forms", Journal of Controlled Release 90:143-162 (2003).
Sun et al., "Intestinal electric stimulation decreases fat absorption in rats: Therapeutic potential for obesity", Obes Res. Aug. 2004; 12(8):1235-42.
U.S. Pat. No. 8,668,662, dated Mar. 2014, Levine (withdrawn).
International Search Report—Application No. PCT/US2017/029571 dated Sep. 11, 2017.

* cited by examiner

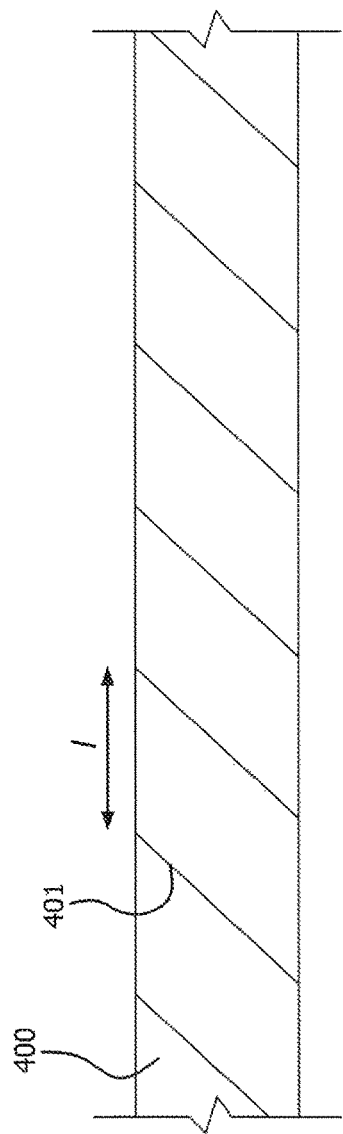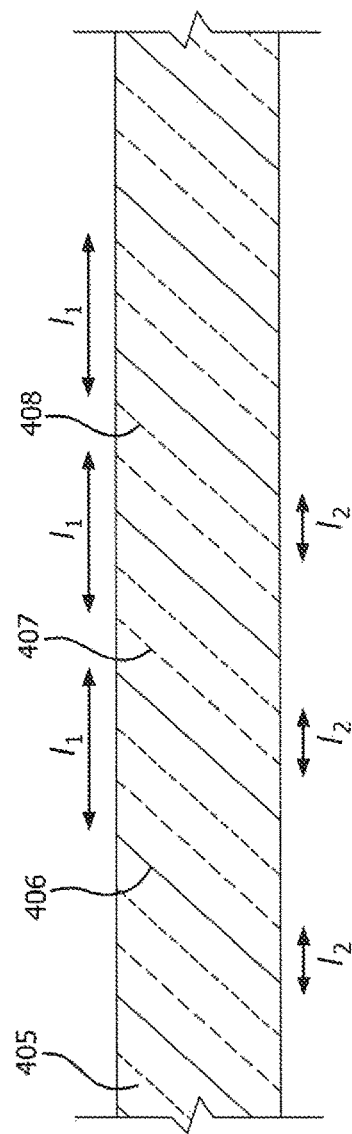
FIG. 4A
FIG. 4B

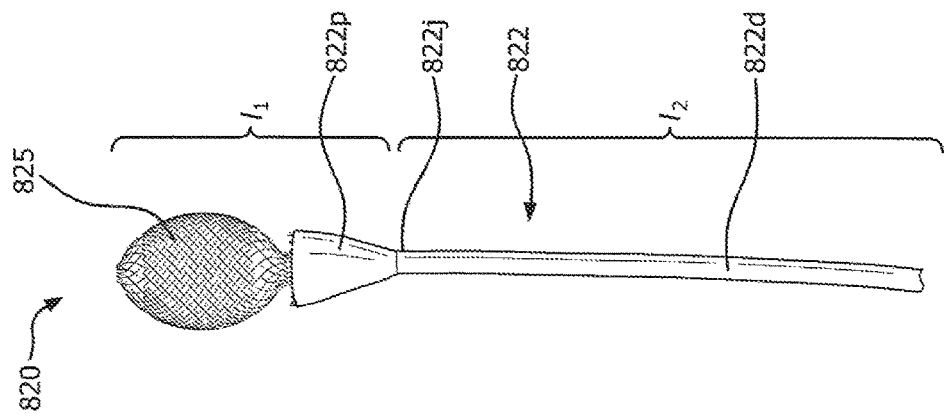
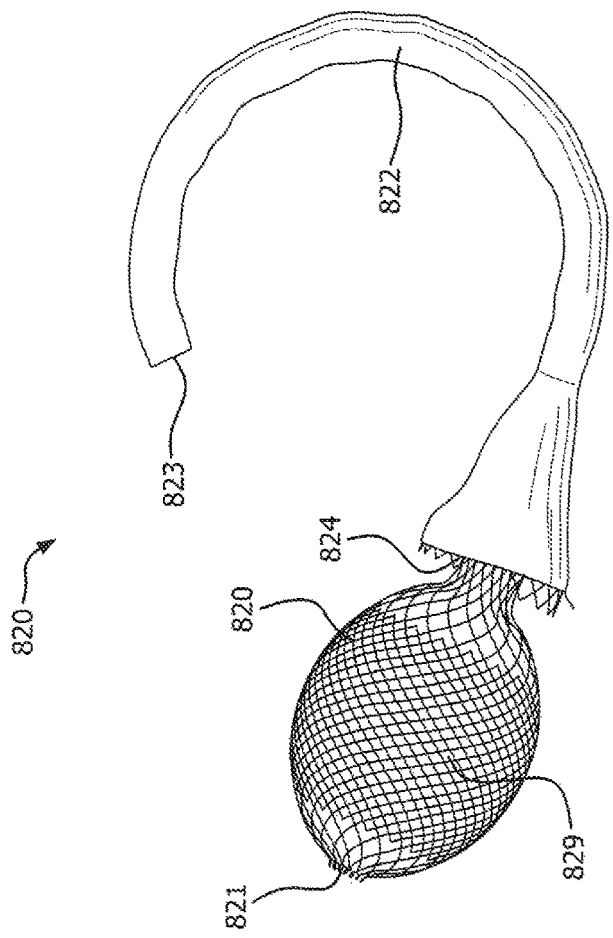
FIG. 8D
FIG. 8C

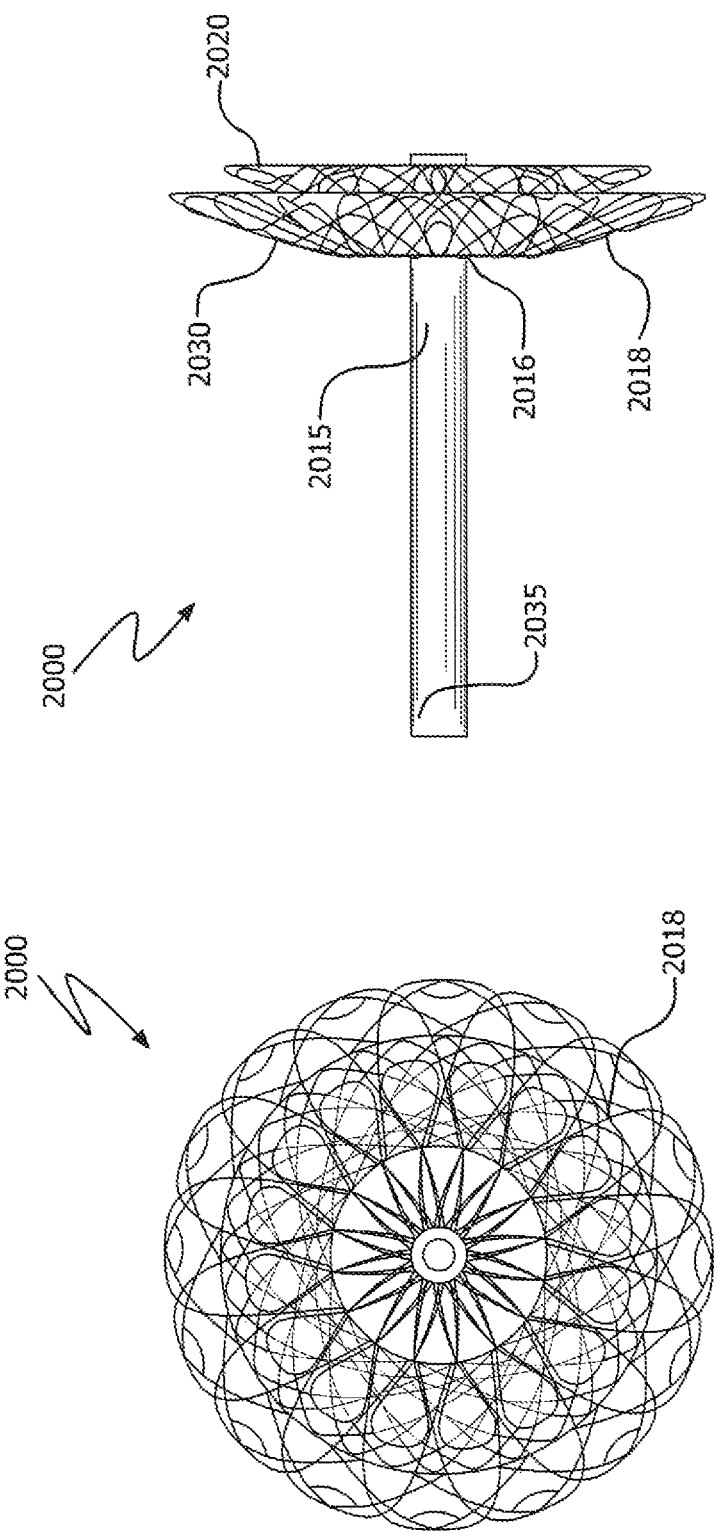

INTRAGASTRIC DEVICE FOR TREATING OBESITY

FIELD

The present specification relates generally to medical devices useful in the treatment of obesity. More particularly, the present specification relates to intragastric and gastrointestinal devices of dynamic weight that reduce gastric volume, slow gastric emptying, and/or bypass portions of the small intestine, thereby leading to patient weight loss.

BACKGROUND

Obesity is a common condition and growing public health problem in developed nations including the United States. As of 2009, more than two thirds of American adults, approximately 127 million people, were either overweight or obese. Over one third of American adults are obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States over $100 billion annually in direct and indirect health care expenses and in lost productivity. This trend is also apparent in many other developed nations.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m2 is associated with significant co-morbidities. Morbid obesity is defined as possessing either a body weight more than 100 pounds greater than ideal or a BMI greater than 40 kg/m2. Approximately 5% of the U.S. population meets at least one of the criteria for morbid obesity. Morbid obesity is associated with many diseases and disorders including, for example: diabetes; hypertension; heart attack; stroke; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are additionally associated with morbid obesity. Taken together, the diseases associated with morbid obesity markedly reduce the odds of attaining an average lifespan. The sequelae raise annual mortality rates in affected people by a factor of 10 or more.

Current treatments for obesity include diet, exercise, behavioral treatments, medications, surgery (open and laparoscopic), and endoscopic devices. New drug treatments for obesity are currently being evaluated in clinical trials. However, a high efficacy pharmaceutical treatment has not yet been developed. Further, short-term and long-term side effects of current pharmaceutical treatments often concern consumers, pharmaceutical providers, and/or their insurers. Generally, diet or drug therapy programs have been consistently disappointing, failing to bring about significant, sustained weight loss in the majority of morbidly obese people.

Currently, most operations used to treat morbid obesity include gastric restrictive procedures, involving the creation of a small (e.g., 15-35 ml) upper gastric pouch that drains through a small outlet (e.g., 0.75-1.2 cm), setting in motion the body's satiety mechanism. About 15% of operations used to treat morbid obesity performed in the United States involve combining a gastric restrictive procedure with a malabsorptive procedure. Typical malabsorptive procedures divide small intestinal flow into a biliary-pancreatic conduit and a food conduit. Potential long-term side effects associated with abdominal surgical procedures include herniation and small bowel obstruction. In addition, long-term problems specific to bariatric procedures also include gastric outlet obstruction, marginal ulceration, protein malnutrition, and vitamin deficiency.

Other surgical strategies for treating obesity include endoscopic procedures, many of which are still in development. Endoscopic procedures and devices to produce gastric pouch and gastrojejunal anastomosis are used to replicate laparoscopic procedures. Endoscopically placed gastric balloons restrict gastric volume and result in satiety with smaller meals. For example, U.S. patent application Ser. No. 10/221,562, now issued as U.S. Pat. No. 7,172,613 and assigned to Districlass Medical SA, describes an "intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume."

The silicone intragastric balloon (IGB) has been developed as a temporary aid to achieve weight loss specifically for people who weigh 40% or more of their ideal weight and who have had unsatisfactory results in their treatment of obesity, despite being cared for by a multidisciplinary team. This treatment is also indicated for morbidly obese patients who have a high morbidity and mortality risk for surgery. The placement and removal of the IGB is an endoscopic procedure and the balloon is designed to float freely inside the stomach. The IGB technique reduces the volume of the stomach and leads to a premature feeling of satiety. However, use of IGBs did not show convincing evidence of a greater weight loss. The relative risks for minor complications, for example, gastric ulcers and erosions, were significantly raised. All inflatable IGB devices suffer from the problem of deterioration of the balloon over time. This deterioration can result in deflation with loss of efficacy and complications such as small bowel obstruction secondary to balloon migration. Due to loss of efficacy over time, IGB devices are recommended only for short (<6 month) durations. In addition, rapid inflation of the balloon poses the risk of esophageal or gastric perforations, both of which are surgical emergencies. Deaths have been reported in patients using IGB treatment.

Endoscopic procedures are also used to deploy mesh structures into the stomach in an effort to occupy stomach volume and create the artificial sensation of being full. For example, U.S. patent application Ser. No. 11/657,231, assigned to Wilson-Cook Medical, Inc., describes an "intragastric device generally compris[ing] a strip digestive-resistant mesh material that is operable between a first configuration and a second configuration. The first configuration is sufficiently small to permit introduction of the digestive-resistant mesh material into a gastric lumen of the mammal. The second configuration is sufficiently large to prevent the digestive-resistant mesh material from passing through the mammal's pylorus, thereby permitting the mesh member to act as an artificial bezoar."

Although endoscopically placed balloon structures can be effective, they are not without their associated risks and complications. Mesh structures are effective in occupying available gastric volume but they do not address gastric emptying. Migration and small bowel obstruction from such devices continue to remain a significant problem. Therefore, a need exists for an intragastric device to treat obesity that combines the benefits obtained through reducing stomach volume, slowing gastric emptying, and providing a bypass for food past the pylorus and a portion of the small intestine, while remaining relatively safe. The device should also include a component for preventing migration of the entire device out of the stomach. This device should limit side effects and be able to be deployed and removed in a non-invasive manner with relative ease. In addition, this device should have the option of further treating obesity by including the benefits obtained by malabsorptive diversion procedures. The addition of this optional benefit would make the device effective in treating not only obesity, but type II diabetes as well.

Typical metal structures cannot survive the hostile environment, particularly with respect to the high acidity, of the stomach. Intragastric devices comprising acid-sensitive components, such as metal wires, are typically covered or coated in an acid-resistant material (i.e. silicone) to prevent degradation of these components by acidic gastric contents. Conventional manufacturing processes for creating these coated intragastric devices first coat the metal wires of the device and then form the wires into the desired end shape of the device. As the shapes and structures of intragastric devices become more complicated, these conventional processes are unable to properly create the desired end product. A shape memory metal, such as Nitinol, is heat-set at temperatures in excess of 400° C. Coating the metal with an acid-resistant material and then heat-setting into the final shape would result in destruction of the coating during exposure to the high temperatures. Therefore, a method of manufacture is needed wherein the wires of the intragastric device are first formed into the desired end shape and are then coated with a corrosion-resistant material. Such a method will take care to prevent the coating and covering or clogging of the spaces or openings between the wires of the wire mesh. Such a method will also produce a finished device that is still flexible enough to be converted from a compressed, first pre-deployment shape to an expanded, post-deployment shape.

Specific surgical options for the treatment of obesity also include laparoscopic sleeve gastrectomy (LSG) and laparoscopic roux-en-y-gastric bypass (RGB) surgery. Gastrectomy refers to a partial or full surgical removal of the stomach. LSG is a restrictive treatment, surgical weight-loss procedure in which the stomach is reduced to approximately 25% of its original size by surgical removal of a large portion following the major curve. The open edges are then attached together (often with surgical staples) to form a sleeve or tube with a banana shape. The procedure permanently reduces the size of the stomach. The procedure is performed laparoscopically and is not reversible. Following the operation, the stomach empties its contents rapidly into the small intestine, but with little or no vomiting (characteristic of other restrictive procedures).

LSG involves a longitudinal resection of the stomach on the greater curvature from the antrum starting opposite the nerve of Latarjet up to the angle of His. The first step of the procedure is the division of the vascular supply of the greater curvature of the stomach which is achieved with the section of the gastro-colic and gastro-splenic ligaments close to the stomach. The greater curvature is completely freed up to the left crus of the diaphragm to resect the gastric fundus that harbors the ghrelin secreting cells of the stomach. The second step of the procedure is the longitudinal gastrectomy that "sleeves" the stomach to reduce its shape to a narrow tube. The pylorus and part of the antrum are preserved, resulting in a lesser curvature-based "restrictive" gastric sleeve.

Sleeve gastrectomy (also called gastric sleeve) is usually performed on extremely obese patients, with a body mass index of 40 or more, where the risk of performing a gastric bypass or duodenal switch procedure may be too large. A two-stage procedure is performed: the first is a sleeve gastrectomy; the second is a conversion into a gastric bypass or duodenal switch. Patients usually lose a large quantity of their excess weight after the first sleeve gastrectomy procedure but, if weight loss ceases, the second step is performed. For patients that are obese but not extremely obese, sleeve gastrectomy alone is a suitable operation with minimal risks. Sleeve gastrectomy is currently an acceptable weight loss surgery option for obese patients as a single procedure. Most surgeons prefer to use a bougie (tapering cylindrical instrument) having an outer diameter between 32-60 French (the optimal bougie size is 32 Fr-36 Fr) with the procedure. The ideal approximate remaining capacity of the stomach after the procedure is 15 ml.

One of the mechanisms involved in weight loss observed after the LSG is the dramatic reduction of the capacity of the stomach. The concept of restriction has been widely used in bariatric surgery in vertical banded gastroplasty (VBG) and laparoscopic adjustable gastric banding (LAGB). The distension of the small gastric pouch in the LAGB procedure or VBG is intended to account for the feeling of early fullness, enhanced satiety and decreased hunger experienced by a patient after the ingestion of small quantities of food.

The hormonal modifications induced by LSG differ from those found after a purely restrictive procedure such as LAGB. Ghrelin, a peptide hormone mainly produced in the fundus of the stomach, is believed to be involved in the mechanisms regulating hunger. There is a significant reduction in ghrelin associated with resection of the gastric fundus.

What makes LSG a preferable option lies in the fact that the operation is a straightforward procedure that can generally be completed laparoscopically, even in the case of an extremely obese patient. It does not involve any digestive anastomosis and no mesenteric defects are created, eliminating the risk of internal hernia. In addition, no foreign material is used as in the case of gastric banding, the whole digestive tract remains accessible to endoscopy, and it is not associated with Dumping syndrome. Also, the risk of peptic ulcer is low and the absorption of nutrients, vitamins, minerals and drugs is not altered.

Early reports of LSG have shown it to be safe and effective with marked weight loss and significant reduction of major obesity-related comorbidities. The question whether LSG may work as a sole bariatric procedure in the long term cannot yet be answered. For this reason, LSG is proposed as the first step of a staged approach in patients for whom a biliopancreatic diversion with duodenal switch (BPD-DS) or RGB seems too hazardous because of a very high BMI (super obesity=BMI >50 or super-super obesity=BMI >60) and/or associated diseases whether related or not to obesity.

Laparoscopic roux-en-y-gastric bypass (RGB) involves the creation of a small (20-30 ml) gastric pouch and a Roux limb (typically 75-105 cm) that reroutes a portion of the alimentary tract to bypass the distal stomach and proximal small bowel. Following RGB, a pleiotropic endocrine response may contribute to improved glycemic control, appetite reduction, and long-term changes in body weight. RGB also has a profoundly positive impact on obesity-related comorbidities and quality of life. Other advantages include established long-term effectiveness for sustained weight loss, reduction of comorbidities, minimal risk for long-term nutritional sequelae, and effective relief of gastroesophageal reflux disease (GERD). RGB is not without risks. Common causes of death include pulmonary embolism and anastomotic leaks. Nonfatal perioperative complications include anastomotic leaks, venous thromboembolism, wound infections, small bowel obstruction, and bleeding. Postoperative gastrointestinal complications include nausea and vomiting, micronutrient deficiencies, and possible weight regain.

Failures after these bariatric procedures are common and patients start regaining weight or the progressive weight loss stops at a sub-therapeutic level. Therefore, there is a need for salvage therapy after one or more failed bariatric procedures. What is needed is a device to be used following bariatric surgery that will combine the benefits of gastric volume reduction, bilio-pancreatic diversion and/or intestinal bypass to enhance the weight loss effects of the device. What is also needed is a device that will further reduce the volume of a surgically restricted stomach to reduce the amount of calories that can be consumed. The device will also bypass the proximal small intestine or the roux limb of the intestine in order to produce intestinal mal absorption, bilio-pancreatic diversion or both. The device can further act to delay gastric emptying, release the gastric hormones associated with satiety, and stimulate the gastric nerves associated with sensation of satiety. The device could be combined with other therapeutic agents such as electrical stimulation, magnetic stimulation, or pharmaceutical agents.

The device can be used as a primary therapeutic procedure for weight loss or as a bridge to surgery for a definitive weight loss procedure. The device may also be used in the treatment of other conditions including, but not limited to, metabolic syndrome, diabetes mellitus, dyslipidemias and cardiovascular disease.

SUMMARY

The present specification discloses an intragastric device for treating obesity comprising: a compressible component having a pre-deployment configuration and a post-deployment configuration and adapted to be positioned and free-floating within a stomach of a patient when in said post-deployment configuration; and a sleeve having a proximal end, a distal end, and a lumen within wherein said sleeve is attached at its proximal end to a distal end of said compressible component and extends through a pylorus of said patient such that said distal end of said sleeve is positioned within a mid-duodenum of said patient, further wherein said sleeve is configured to transit food from said stomach of said patient to said mid-duodenum such that said food bypasses said pylorus and a proximal duodenum of said patient; wherein said compressible component is configured to occupy space in said stomach and provide positioning support to said sleeve such that said sleeve does not migrate in a distal direction into a patient's jejunum or more than 5 cm in a proximal direction in said stomach, further wherein said compressible component does not include food sequestering or delayed gastric emptying properties.

The intragastric device may be configured to be delivered by a catheter.

Optionally, the compressible component is composed of a shape memory metal. The shape memory metal may be Nitinol. Optionally, the intragastric device further comprises a non-porous balloon positioned over said shape memory metal and configured to reduce the exposure of said shape memory metal to gastric acid. The balloon may be inflatable with air, water, and saline. The intragastric device may be configured to have a functional life of at least one year wherein functional life is defined as a time period before said shape memory metal begins to degrade as a result of expose to gastric acid. The balloon may be sutured to said compressible component.

Optionally, the intragastric device further comprises a stent positioned between said compressible component and said sleeve and configured to be positioned in said pylorus.

The compressible component may have a shape comprising any one of a balloon, double balloon, ball, parachute, inverted parachute, disc, double disc, horseshoe, flower, teardrop, double teardrop, cylinder, inverted square pyramid, funnel, bobbin, lotus, wine glass, or orange peel.

The sleeve may have a shape comprising any one of a cylinder or funnel.

Optionally, the compressible component and the sleeve are not physically attached at any point to a patient's anatomy.

Optionally, the compressible component and the sleeve are configured to be atraumatic to the patient's anatomy.

The compressible component may be configured to apply pressure to said stomach to induce a feeling of fullness or satiety in said patient.

Optionally, the intragastric device further comprises a second compressible component attached to a proximal end of said compressible component configured to occupy additional stomach space and provide additional pressure to said stomach.

Optionally, the compressible component further comprises a collar at its distal end configured to assist in positioning said sleeve.

The present specification also discloses a gastrointestinal device for treating obesity comprising a three-dimensional porous structure configurable between a compressed pre-deployment configuration to facilitate delivery and an expanded post-deployment configuration. The porous structure includes a first opening at its proximal end and a larger second opening at its distal end. The porous structure also includes a sleeve coupled to its distal end. Optionally, the device further includes a suture at the proximal end of the wire mesh structure to facilitate retrieval and an anti-migration component positioned at the junction of the porous structure with the sleeve. The porous structure is deployed in a patient's stomach such that the anti-migration component sits proximal to the patient's pylorus and prevents migration of the entirety of the device into and through the pylorus. The sleeve extends through the pylorus, into the duodenum and ends in the duodenum or jejunum. Food enters the device from the first opening at the proximal end of the porous structure, passes through the porous structure and sleeve, and exits at the distal end of the sleeve. The device treats obesity by providing a relatively immovable volume occupying structure in the stomach and a bypass for food past the pylorus and proximal portion of the small intestine. Optionally, the device further acts to slow the passage of food through the digestive tract. Patients with the device experience satiety more quickly and have a prolonged sensation of satiety. Optionally, the device is anchorless and atraumatic. Optionally, the intragastric device is used to deliver prebiotic and/or probiotic therapy to the patient.

The aforementioned and other embodiments of the present invention shall be described in greater depth in the drawings and detailed description provided below.

BRIEF DESCRIPTION OF THE DRAWINGS

These and other features and advantages of the present invention will be appreciated as they become better understood by reference to the following detailed description when considered in connection with the accompanying drawings, wherein:

FIG. 4A is an illustration of a portion of a sleeve component of an intragastric device in a post-deployment configuration in accordance with one embodiment of the present specification, depicting a single wire support spiraling along the body of the sleeve;

FIG. 4B is an illustration of a portion of a sleeve component of an intragastric device in a post-deployment configuration in accordance with one embodiment of the present specification, depicting multiple wire supports spiraling along the body of the sleeve;

FIG. 8C is an illustration of an intragastric device comprising a wire mesh structure and attached sleeve, in accordance with one embodiment of the present specification;

FIG. 8D is an illustration of the intragastric device of FIG. 16C with the sleeve straightened to depict the device dimensions relative to the surrounding anatomy;

FIG. 20A illustrates another embodiment of the free floating structure before deployment, according to one embodiment;

FIG. 20B illustrates a circular mesh-shaped structure after deployment, according to one embodiment;

DETAILED DESCRIPTION

Figure 1:
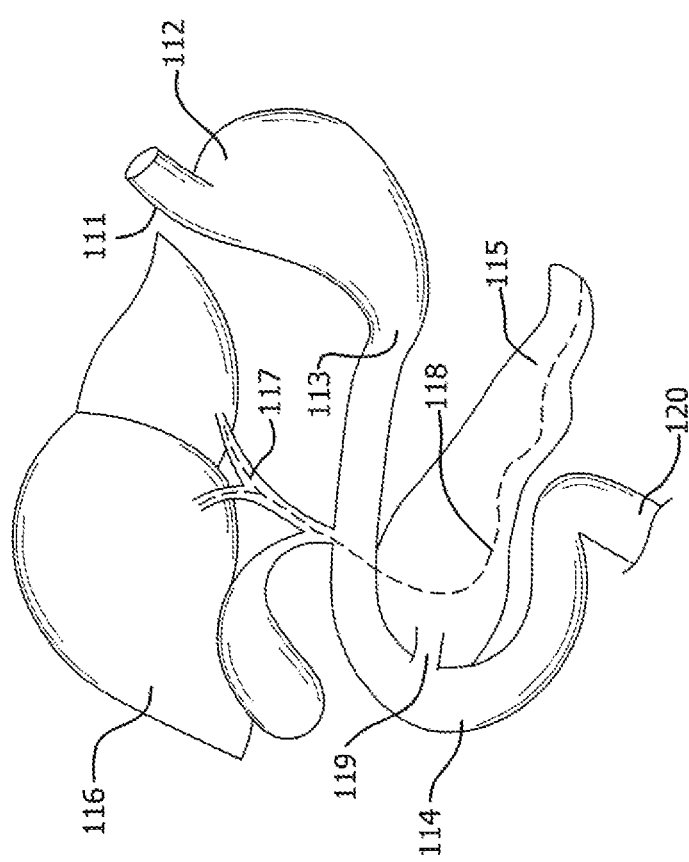
FIG. 1 is an illustration of an upper gastrointestinal system.

In one embodiment, the present specification is directed toward an intragastric device of dynamic weight used in obese patients to induce weight loss. In various embodiments, the intragastric device comprises a porous three dimensional structure having a pre-deployment shape and a post-deployment shape. In one embodiment, the porous three dimensional structure is a non-inflatable wire mesh structure, or a spiral structure made of shape memory metal or shape memory polymer that changes from a pre-deployment compressed cylindrical shape to a post-deployment sphere, oval, kidney bean or any predefined shape of significant volume. In another embodiment, the intragastric device is made of a plastic material or a polymer such as polyether ether ketone (PEEK) or polyester or a bioresorbable material. The device changes back and forth from the pre-deployment to post-deployment shape by minimal mechanical force and/or temperature changes arising from the room temperature pre-deployment shape to the body temperature post-deployment shape.

In another embodiment, the device comprises compressible free-floating structure in the stomach with an attached sleeve which passes through the pylorus and into the duodenum. The device in this embodiment is anchorless and atraumatic, as it is not physically attached to any part of the GI tract and does not damage the GI tissue.

In one embodiment, the device is delivered endoscopically to the stomach via a catheter. The device can be placed through the endoscope, over an endoscope or over a guidewire with endoscopic or fluoroscopic guidance/assistance.

The device has a pre-deployment compressed shape to facilitate insertion and a post-deployment expanded shape that resides in the gastric lumen. Post-deployment volume of the device is significantly larger than pre-deployment volume. In one embodiment, the post-deployment device has a volume of at least 100 ml. The post-deployment device occupies a significant volume in the stomach, thereby reducing available gastric volume available for storage of ingested food. This restricts the amount of food intake, inducing satiety and curbing one's appetite. In one embodiment, the device is also designed to intermittently, with gastric peristalsis, slow or block the passage of the food from the stomach into the small intestine, thereby slowing gastric emptying. In various embodiments, the device also functions to create a biliopancreatic diversion, either by bypassing ingested food past pancreatic secretions or by bypassing pancreatic secretions past ingested food.

In one embodiment, the device comprises a shape memory metal and self-expands once deployed to change from the pre-deployment shape to the post-deployment shape. In another embodiment, the device comprises a temperature sensitive metal that is cooled in its pre-deployment shape and then self-expands when exposed to human body temperature to achieve its post-deployment shape. In another embodiment, an expansion tool is used to apply minimal mechanical force to change the device shape from its pre-deployment shape to its post-deployment shape. In another embodiment, a plastic, polymer, carbon fiber or a bioresorbable material is used to construct the intragastric device.

In one embodiment, the wire structure contains differently weighted material to assist in proper positioning within the stomach. In one embodiment, lighter weighted material is positioned at the top of the wire structure proximate to the top openings and heavier weighted material is positioned at the bottom of the structure, proximate to the bottom openings. This differential weighting insures that the device will be properly situated within the stomach to effectuate the intended effect of slower gastric emptying. In addition, the differential weighting provides for proper gastric positioning without the need of physically anchoring the wire mesh structure to the stomach wall. The differential weight property can also be provided by the ingested food material that enters the device and is selectively accumulated toward the bottom of the device facilitated by the gravitational pull. The differential weight can also be provided by using different amounts of material in the top and bottom halves. The wire mesh structure is free to move about within the stomach while still maintaining its correct top to bottom alignment facilitated by the gravitational pull.

In one embodiment, the device comprises a wire mesh structure which, when in the post-deployment shape, includes mesh openings between the wires of the mesh structure. In one embodiment, the mesh openings are greater than 1 mm in diameter. In one embodiment, the wires of the wire mesh structure are coated with a corrosion-resistant material. The corrosion resistant material prevents exposure and subsequent degradation of the wires of the wire mesh structure from acidic gastric contents once deployed. The corrosion-resistant material completely covers the wires of the wire mesh but does not cover the mesh openings. In one embodiment, the corrosion-resistant material comprises parylene. Parylene is beneficial as a coating in that it is durable, may mitigate nickel ion leaching, and has a lower profile (is thinner once applied). In various embodiments, the corrosion-resistant material comprises silicone, polyester, polyether ether ketone (PEEK), a medical grade epoxy, ceramic, an additional metal, or any other suitable, flexible corrosive resistant material. In one embodiment, the coating metal is tantalum. Tantalum provides corrosive resistance and radiopacity. In one embodiment, wherein the coating is ceramic, the ceramic coating has a thickness of several angstroms. In various embodiments, any one or combination of the above corrosive resistant materials is used to coat the metal of the wire mesh structure.

In one embodiment, the mesh openings are differentially structured to regulate the flow of food in and out of the mesh. In one embodiment, at least one opening on the bottom half of the device is larger than any of the openings on the upper half of the device, allowing food entering the mesh to exit without the need for further reduction in size of food material.

In another embodiment, the intragastric device further includes an anti-migration component, or collar, coupled to a portion of its distal end. The anti-migration component, similar to the wire mesh of the intragastric device, is configurable between a first, compressed configuration for delivery, and a second, expanded configuration once deployed. The anti-migration component functions as a physical stopper preventing passage of the intragastric device through the pylorus. In various embodiments, the anti-migration component has a diameter that is greater than the diameter of a relaxed pylorus. In one embodiment, the anti-migration component comprises an extension of the wire mesh structure of the intragastric device. In another embodiment, the anti-migration component is a separate piece of wire mesh which is attached to a portion of the distal end of the intragastric device. In various embodiments, the anti-migration component has a shape approximating a bumper, half-bumper, disc, saucer, or any other shape which will prevent migration of the device past the pylorus.

In other embodiments, a sleeve can be attached to the intragastric device, where the sleeve extends from the stomach into the duodenum where it empties, or through the duodenum and into the jejunum. In one embodiment, the sleeve functions to transit the sequestered chyme from the wire mesh structure directly to the mid duodenum or mid-jejunum. In another embodiment, the sleeve is coupled to the intragastric device but does not directly receive food from the device. In this embodiment, the proximal end of the sleeve is distal to the device and receives food directly from either the stomach or the duodenum. The food entering the sleeve exits at the distal end, into the duodenum or jejunum, bypassing a portion of the small intestine.

The sleeve therefore acts to bypass portions of the gastrointestinal (GI) tract in order to limit the absorption of specific materials in the intestine. The benefits provided by a sleeve are similar to those provided by Roux-en-Y gastric bypass surgery, namely, weight loss and improvement of type II diabetes.

After implantation, the gastrointestinal device of the present specification, particularly the collar, is in constant physical contact with the patient's anatomy without being actually physically attached to the patient's anatomy. This is accomplished by the sleeve being pulled down by the peristaltic actions of the small intestine. As the sleeve is pulled down, the collar of the wire mesh structure contacts the stomach proximal to the pylorus. The sleeve is constantly in physical contact with the pylorus. However, this constant contact with the pylorus does not block food passage. The openings of the wire mesh structure and the lumen of the sleeve pass food through pylorus without occluding it at any point, allowing the food to pass into the intestines. The intragastric device of the present specification physically engages the gastric emptying region of stomach without fully occluding it any point. The intragastric device of the present specification functions as a variable outlet drain and does not act as a stopper to the passage of food.

The gastrointestinal device of the present specification is designed to maximize the amount of food captured and passed through the sleeve and into the intestines rather than minimizing the amount of food passing into intestines. By being in constant contact with the pylorus and stomach, the device is designed to prevent food from passing around and outside of it. In various embodiments, at least 10% of the food exiting a patient's stomach passes through the device and not around the device. In one embodiment, at least 50% of the food exiting a patient's stomach passes through the device and not around the device. In various embodiments, this food that passes into the device and through the sleeve never comes into contact with the patient's duodenum, thereby allowing the device to function as a true pyloric bypass.

In one embodiment, the device is an inflatable balloon with an attached sleeve, wherein the balloon is not in fluid communication with a lumen of the sleeve and the balloon merely acts to hold the sleeve in position without the need to anchor or fix the sleeve to the gastrointestinal wall. The balloon can be inflated or deflated with fluid and is designed to reside in a person's stomach. The sleeve is flexibly attached to the balloon and has a proximal opening and a distal opening wherein the proximal opening is designed to reside proximal to a patient's ampulla and the distal opening is designed to reside distal to a patient's ampulla. Partially digested food enters the proximal opening and exits the distal opening, bypassing the ampullary region. The sleeve is not anchored or fixed to any portion of the gastrointestinal wall.

Wire Mesh Structure

In various embodiments, the intragastric device comprises a porous three dimensional structure having a pre-deployment shape and a post-deployment shape. In one embodiment, the device, in the post-deployment configuration, comprises a three dimensional wire mesh structure defining an internal volume and having a proximal end and a distal end.

In various embodiments, the wire mesh structure includes free ends or 'nodes' comprising bends or curves in the wire of the wire mesh structure wherein these bends or curves are unsupported and not connected to any other portion of the wire mesh. In some embodiments, the wire mesh structure includes two pluralities of nodes. A first plurality is positioned at the proximal end of the structure and a second plurality is positioned at the distal end of the structure. When the wire mesh structure is compressed to its pre-deployment configuration, the first and second plurality of nodes at the proximal and distal ends of the structure respectively, become gathered together or 'bunched up'. This creates a larger cross-sectional area (or diameter) at the proximal and distal ends of the structure when compared to the cross-sectional area of the compressed structure between said ends. As its cross-sectional area becomes larger, the compressed wire mesh structure becomes increasingly difficult to deploy through a narrow delivery device or catheter. This delivery problem can be addressed in at least two different ways. In various embodiments, the number of nodes in each plurality of nodes is reduced. Reducing the number of nodes in each plurality makes the structure easier to compress and creates a smaller cross-sectional area at the ends of the structure. This reduces the force applied by the compressed structure to the delivery catheter, thereby making it easier to pass the compressed structure through the catheter. In various embodiments, a portion of the nodes from one or both of the first and second plurality of nodes is moved from said ends of the structure and positioned along the body of the structure, creating additional pluralities of nodes. This 'staggering' of the nodes reduces the cross-sectional area of the compressed structure at any given point and distributes the force applied by the compressed structure to the delivery catheter, again easing the passage of the delivery structure through the catheter. In various embodiments, the number of nodes in each plurality is reduced and the nodes are staggered in multiple pluralities throughout the structure to reduce and distribute the force applied by the compressed structure to the delivery catheter. Reducing and distributing said force allows for easier delivery and for the use of a delivery catheter having a smaller diameter. Reduced and distributed forces also allow for the creation of larger mesh structures that can be compressed to smaller sizes.

In various embodiments, each plurality of nodes comprises 10 to 100 individual nodes. In one embodiment, each plurality of nodes comprises 44 nodes. In another embodiment, each plurality of nodes comprises 36 nodes. In various embodiments, a wire mesh structure includes 2 to 60 pluralities of nodes distributed latitudinally at different locations along its length. In one embodiment, the nodes are staggered such that at least 10% of the total number of nodes in the structure are positioned at the proximal and distal ends. In various embodiments, no more than 75% of the total number of nodes are positioned in any one plurality of nodes. In various embodiments, the nodes are distributed within at least three different lateral pluralities along the length of the structure.

The compressibility of the wire mesh structure also depends on the flexibility of the mesh. The flexibility, in turn, depends upon, among other variables, the thickness of the wire, the angle of wire intersections, and the number of wires. Regarding the angle of wire intersections, as the wires of the structure are arranged more parallel to one another, the structure becomes more flexible. In various embodiments, the wire mesh structure, in a pre-deployment configuration, has an overall length of 5 to 50 cm and each wire has a thickness in a range of 0.1 to 1 mm. In one embodiment, each wire has a thickness of 0.44 mm. The wires of the wire mesh structure have a bending strain which determines how they behave as the structure is compressed. In various embodiments, the wires are comprised of a shape memory metal, such as, in one embodiment, Nitinol. The shape memory metal has a certain bending strain percentage beyond which the metal loses its ability to exactly regain its previous shape. The strain percentage (%) can be defined by the following formula:

$$\text{strain \%} = 2t/R \times 100$$

wherein t=thickness of the wire and R=radius of the bend. In one embodiment, once the strain percentage reaches 8%, a permanent change is introduced to the shape memory metal such that it will no longer return fully to its original shape. This factor becomes important as the wire mesh structure is compressed to its pre-deployment shape for delivery. In various embodiments, the wire mesh structure includes a collar or circular extension of the wire mesh at its distal end which functions as an anti-migration component. This collar must me folded out distally during compression such that the compressed structure will fit into the delivery device or catheter. A 'bump' in the wire mesh structure is introduced as the collar is folded out during compression. A strain percentage of less than 8% creates a smaller bump in the compressed wire mesh structure, allowing for easier passage of the compressed structure through a delivery catheter. Therefore, in various embodiments, the wire mesh structure is configured having a wire thickness and a bend radius at the collar such that the strain percentage at the collar will be no more than 20%, and preferably less than 8%. In various embodiments, the radius of the collar is less than 10 times the wire thickness. In various embodiments, the strain percentage is in a range of 0.1 to 20%. In various embodiments, the wire of the wire mesh has a thickness of 0.1 to 1.0 mm and the collar has a bend radius of 0.013 to 20 cm. In one embodiment, the wire of the wire mesh has a thickness of 0.4 mm. In various embodiments, the wire thickness and bend radius are configured to satisfy the following statement:

$$2t < R < 2000t$$

wherein t=thickness of the wire and R=radius of the bend.

In various embodiments, the ends of the wire(s) of the wire mesh structure are terminated in such a way to minimize the possibility of traumatic injury to body tissues during delivery and retrieval and while deployed. In some embodiments, the wire mesh structure comprises a single wire folded into a three dimensional structure. In other embodiments, the wire mesh structure comprises more than one wire joined and folded into a three dimensional structure. In various embodiments, the free ends of the wire or wires are joined by crimping a titanium tube or Nitinol (or other shape memory metal) tube over said free ends. In other embodiments, the free ends of the wire or wires are joined by spot welding said free ends together. In one embodiment, the intersections of the wires are not welded. In another embodiment, the intersections of the wires are welded.

In one embodiment, the wire mesh structure is enveloped in a silicone balloon that compresses to a capsule for delivery. After delivery, the wire mesh structure expands together with the envelope. The balloon envelope slows down the exposure of the wire mesh to acid, which corrodes the Nitinol material of the mesh, thereby prolonging the device life.

Sleeve

In various embodiments, the intragastric device of the present specification further comprises a flexible sleeve component coupled to the wire mesh structure. In multiple embodiments, any of the wire mesh structures discussed above is coupled with any of the sleeve components discussed below. The sleeve component comprises an elongate tubular body having a proximal end and a distal end a lumen within.

In one embodiment, the sleeve has a consistent diameter along its entire length. In other embodiments, the sleeve comprises a funnel shape proximate its proximal end wherein the diameter of the sleeve is greatest at the first opening at the proximal end of the sleeve body and then decreases gradually as it extends distally until it reaches a minimum diameter at a position proximal to the midpoint of its length. The diameter then remains constant distally along the remainder of its length.

In various embodiments, wherein the wire mesh structure includes a collar at its distal end, the proximal end of the sleeve is attached to the bottom surface of said collar by one of the means listed above. In various embodiments, when the device is compressed into its pre-deployment configuration, the sleeve body is pulled upon to assist in folding out the collar. If the proximal end of the sleeve is attached to the bottom surface of the collar as described above, the collar is not fully straightened when folded out, resulting in the creation of a large bulge at the collar when the device is in the pre-deployment configuration. The bulge has a large diameter comprising the thickness of the wire mesh structure and double the thickness of the sleeve. Therefore, in preferred embodiments, the proximal end of the sleeve is attached to the free ends, or nodes, of the collar by a plurality of loose sutures. The sleeve is sutured to each node much similar to the way in which the fabric of an umbrella is attached to the end of each spine of the umbrella. When an umbrella is closed, the fabric collapses down to allow for compression. The intragastric device of the present specification functions in a similar manner. In various embodiments, as the wire mesh structure is compressed for loading onto a delivery device, the distal end of the sleeve is pulled upon. The loose sutures attaching the sleeve to the nodes of the wire mesh allow the sleeve to move relative to the wire mesh such that the collar is pulled distally and extended into a more linear shape. Such an attachment avoids the creation of a large bulge at the collar of the pre-deployment configuration. When the sleeve body is pulled upon during compression, the collar is folded out more completely and the resultant bulge has a smaller diameter, comprising only the thickness of the wire mesh structure. In various embodiments, when the intragastric device is in the pre-deployment configuration, there is minimum to zero overlap between the collar and the sleeve. Upon deployment, the shape memory properties of the wire mesh structure cause the collar to pull the sleeve onto itself as it expands, much like an umbrella expanding its fabric as it opens.

In various embodiments, each node at the distal end of the wire mesh structure (or collar) is attached to the proximal end of the sleeve via a suture. This can lead to bulking at the attachment of the wire mesh structure to the sleeve. Therefore, in other embodiments, fewer nodes are sutured to the sleeve. For example, in one embodiment, every other node is sutured to the sleeve to reduce the number of suture knots and decrease bulking. The inclusion of glue and multiple loops in each suture knot can also lead to bulking at the attachment point of the wire mesh structure to the sleeve. As such, in various embodiments, glue is not used and each suture knot is limited to one loop. Suturing of the sleeve to the nodes can lead to sliding of the suture knots along the length of wire comprising the nodes, resulting in unintended movement of the sleeve relative to the wire mesh structure. To prevent sliding, in various embodiments, each suture knot is placed at the first junctions of the wires proximal to each node. In effect, each suture is then placed over two wires and cannot slide along one or the other. To eliminate excessive bulking, in various embodiments, fewer than every first wire junction is sutured to the sleeve. For example, in one embodiment, every other first wire junction is sutured to the sleeve.

In various embodiments, any sharp ends of wires in the wire mesh and/or sleeve are crimped and looped onto themselves or looped outward to act as pulling points for moving the sleeve into the intestines or for connecting the sleeve to the wire mesh structure.

The distal end of the sleeve can be designed to be weighted so that the sleeve remains in an elongated shape extending through a portion of the duodenum. In one embodiment, the sleeve includes a small weight attached to its distal end. In another embodiment, wherein the second opening at the distal end of the sleeve body is positioned along the sleeve body at its distal end, the distal end of the sleeve body further includes a blind pouch. The blind pouch functions to intermittently trap a small portion of food or fluid there within. The trapped food or fluid acts to weigh down the distal end of the sleeve body, thereby keeping the sleeve component elongated. In one embodiment, the distal end of the sleeve is reinforced with at least a second layer to assist in keeping the distal end positioned downward and prevent it from folding up.

In one embodiment, the sleeve comprises a wire mesh configuration having a plurality of nodes, similar to the configuration described above for the wire mesh structure.

In another embodiment, the sleeve component comprises a membrane that is flexible and compressible by the contractions of the small intestine. In one embodiment, the sleeve includes a minimum level of structure which imparts upon the sleeve a minimum amount of structural strength to resist buckling from gastrointestinal forces and remain functional. In one embodiment, the minimum level of structure comprises a single structure extending along at least 10% of a length of the sleeve to provide the sleeve with linear strength. In various embodiments, the single structure is a straight wire, a wire helix, or a wire mesh. In one embodiment, the membranous sleeve component comprises a plurality of horizontal and/or vertical support elements along the length of the sleeve body. In one embodiment, the horizontal elements include wire rings spaced apart along the length of the sleeve body. In various embodiments, the rings are spaced between 2 and 24 inches apart. In one embodiment, the rings are spaced 6 inches apart. In one embodiment, the vertical support elements include elongate metal wires. In various embodiments, the wires are between 2 and 60 inches in length. In one embodiment, the metal wires are 6 inches in length. In another embodiment, the membranous sleeve component comprises a spiral metal wire extending along its length. The spiral metal wire provides support to the sleeve component and maintains its elongated shape. In various embodiments, the spiral metal wire is comprised of a shape memory metal, such as Nitinol. The spiral metal wire must not be too tight such that, once the sleeve in compressed for delivery, it becomes kinked and cannot regain its full shape. In various embodiments, the spiral metal wire of the sleeve has a thickness of 0.1 to 1.0 mm. In one embodiment, the spiral metal wire of the sleeve has a thickness of 0.2 mm. As similarly discussed above with reference to the collar bend radius, the bend radius of the spiral metal wire of the sleeve should be such to create a strain percentage that will be in a range of 0.1 to 20%, and preferably less than 8%. In various embodiments, the strain percentage (%) of the spiral metal wire can be defined by the following formula:

$$\text{Strain \%} = \frac{d}{200} \times \left[\frac{1}{Rf} - \frac{1}{Ri}\right]$$

wherein d is the diameter of the wire, Rf is the final bend radius, and Ri is the initial bend radius. Therefore, in various embodiments, the spiral metal wire has a pitch in a range of 5 to 150 mm. In one embodiment, the spiral metal wire has a pitch of 60 mm. In various embodiments, the sleeve includes more than one spiral metal wire to provide greater support while still preventing permanent kinking. In one embodiment, the sleeve includes three spiral metal wires wherein each individual wire has a pitch of 60 mm and the wires are spaced such that the pitch between two separate wires is 20 mm. In another embodiment, the sleeve includes six spiral or helical wires to provide structural support to the sleeve. In various embodiments, the membrane of the sleeve component extends proximally onto the lower portion of the wire mesh structure and covers all or a portion of said lower portion.

The sleeve is flexible and compressible such that during delivery it is restrained in a compressed configuration on the distal end of a delivery device. In one embodiment, the sleeve telescopes into itself to shorten its length and facilitate delivery. In addition, when the device is in the pre-deployment configuration, the sleeve can be folded onto itself to shorten its length and assist with placement in a delivery device or catheter. In various embodiments, the sleeve is folded 2 to 10 times upon itself and then folded or wrapped along a delivery device or catheter for delivery. In one embodiment, the sleeve is fed coaxially over a guidewire, a delivery device or catheter. In another embodiment, the sleeve is folded along the side or around a delivery device or catheter. This helps prevent the sleeve from sticking to the guidewire and/or delivery device/catheter as the guidewire and delivery device/catheter are retracted, which is sometimes encountered when the sleeve has been fed coaxially over the guidewire or delivery device/catheter.

In other embodiments, some intragastric devices of the present embodiment include a sleeve having a shorter length than the lengths described above. In various embodiments, the short sleeve has an overall length of 100-120 mm. In various embodiments, the short sleeve has a funnel shape or cone shape. In some embodiments, the short sleeve comprises a wire formed into a wire mesh structure or braid having a plurality of nodes, similar to the configuration described above for the wire mesh structure. In one embodiment, the braid is created using a single wire. In one embodiment, the wire is composed of a shape memory metal. In one embodiment, the shape memory metal is Nitinol. In other embodiments, the braid is created by machine braiding multiple wires. In some embodiments, the pitch, or distance between nodes, is uniform. In other embodiments, the pitch is variable. The ends of the braid are designed to be atraumatic. In one embodiment, the ends are blunted. In another embodiment, the ends are capped with a soft polymeric tip. In some embodiments, a portion of the short sleeve is coated with a covering. In some embodiments, the covered portion comprises the floating nodes. In one embodiment, the covering is silicone. In various embodiments, the diameter of the proximal end of the sleeve is approximately equal to the outer diameter of an anti-migration collar at the distal end of a wire mesh structure. In such embodiments, the proximal end of the sleeve is fitted over and attaches to the anti-migration collar. In other embodiments, the diameter of the proximal end of the sleeve is smaller than the outer diameter of an anti-migration collar and approximately equal to the diameter of a neck of the collar connecting said collar to said wire mesh structure. In these embodiments, the proximal end of the sleeve is attached to said neck of said collar.

In one embodiment, the number of nodes is uniform across the braid. In one embodiment, the number of nodes is 24. In other embodiments, the number of nodes is variable across the braid. For example, in various embodiments, the short sleeve braid includes 24 nodes at the proximal end and 18 or 12 nodes at the distal end. In these embodiments, the nodes comprising the difference in number of nodes between the two ends (for example, 6 or 12 nodes) are floating nodes and are positioned along the body of the short sleeve.

Once an intragastric device having a short sleeve is deployed, the short sleeve intermittently engages and blocks a patient's pylorus without being anchored to the pylorus. This prevents food from passing through the pylorus and forces the food to pass through the short sleeve from the stomach and into the duodenum, thus regulating gastric outflow. In various embodiments, an opening at the distal end of the short sleeve is 1-30 mm in diameter wherein the size of the diameter determines the rate of gastric outflow. In one embodiment, the opening can be 0 mm when the pylorus is engaged, thereby completely blocking outflow. Therefore, food is allowed to enter the duodenum from the stomach only when the pylorus is not engaged or only partially engaged.

In various embodiments, the sleeve has a high coefficient of friction compared to sleeves of the prior art. In various embodiments, the sleeve has a coefficient of friction ranging from 0.01-0.30. In one embodiment, the sleeve has a coefficient of friction equal to or less than 0.10. It has been encountered with relatively smooth sleeves that, during deployment, the smooth sleeve can become stuck to the inside of a delivery catheter or stuck to itself, resulting in destruction of the sleeve as force is applied to free the sleeve. Therefore, a sleeve with a rougher outer surface can be easier to feed into a delivery device or catheter and then deploy. In various embodiments, the sleeve includes a matte outer surface. In other embodiments, a particulate matter or relatively rough substance, such as corn starch or biocompatible powder, is applied to the outer surface of the sleeve prior to loading the sleeve into a delivery device and deployment.

In various embodiments, the sleeve includes one or more radiopaque markers to ensure proper positioning of the sleeve using radiographic imaging. In various embodiments, the radiopaque markers include a plurality of individual markings along an outer surface of the sleeve body. In other embodiments, the radiopaque marker includes a single line extending along an outer surface of the sleeve body. A spiraled single line can indicate twisting of the sleeve. In still other embodiments, the radiopaque markers include a plurality of individual markings and a single line extending along an outer surface of the sleeve body. In other embodiments, no radiopaque markings are necessary as the wire thickness of the support elements of the sleeve is great enough to allow for radiographic visualization.

In another embodiment, the flexible member or sleeve has a surface optimized for adherence and growth of microorganisms. In one embodiment, the device comprises a rigid member, such as a freely floating mesh structure and a flexible member, such as a freely floating sleeve structure, with surfaces of both the members designed to promote micro-organism adherence and growth. The microorganisms produce a desired therapeutic effect including assistance in weight loss, glycemic control, or treatment of irritable bowel syndrome, *clostridium difficile* or any other condition responsive to a prebiotic or a probiotic therapy.

Retrieval Mechanism

In various embodiments, the wire mesh structure or wire mesh structure with coupled sleeve component includes one or more retrieval mechanisms with at least one retrieval mechanism positioned proximate the at least one opening at the proximal end of the wire mesh structure. In one embodiment, the retrieval mechanism comprises an 80 lb. retrieval suture.

Anti-Migration Component

In various embodiments, the wire mesh structure or wire mesh structure with coupled sleeve component includes one or more anti-migration components or collars. In one embodiment, the anti-migration component is comprised of a metal. In one embodiment, the metal is a shape memory metal, such as Nitinol. The anti-migration component is preferably positioned at the distal end of the wire mesh structure (at the junction of the wire mesh structure with the sleeve component in the embodiment of the device including a sleeve) and, once the device is deployed, comes to rest proximal to the pylorus. The anti-migration component functions to prevent passage of the wire mesh structure or entire device through the pylorus.

In various embodiments, various components of the device, including the wire mesh structure, retrieval mechanism, and/or anti-migration component are coated with a therapeutic drug to enhance functionality of the device.

In various embodiments, the wire mesh structure, hook, and/or anti-migration component include a radiopaque marker for radiographic visualization to facilitate delivery and retrieval. In various embodiments, the wire mesh structure, hook, and/or anti-migration component include an ultrasound marker for ultrasound visualization to facilitate delivery and retrieval.

Delivery Device

The present specification also discloses various embodiments of a delivery device used to deploy an intragastric device in the gastrointestinal tract of a patient. An intragastric device is preloaded onto a delivery device which is then used to deliver the wire mesh of the intragastric device into the stomach and the sleeve of the intragastric device into the proximal small intestine.

In one embodiment, a delivery device comprises an elongate tubular body having a coaxial plunger and catheter and a plurality of handles. The handles are manipulated to deploy the sleeve and wire mesh structure of the intragastric device in multiple stages. In one embodiment, the tubular body includes a trigger which controls movement of the various components of the delivery device to effectuate intragastric device deployment.

In various embodiments, the intragastric device can be retrieved using a standard overtube, endoscope, and grasper.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is an illustration of an upper gastrointestinal system. After swallowing, food passes rapidly through the esophagus 111 into the stomach 112. There, it is digested for a period of time and undergoes the process of dilution to an iso-osmotic concentration by grinding and mixing with gastric juices. The stomach 112 relaxes to accommodate the volume of ingested food. As the stomach 112 gets filled with food the sensation of fullness or satiety is generated by stretch receptors in the gastric wall and the person stops eating. The iso-osmotic food, known as chyme, then passes through the pylorus 113 into the duodenum 114. Passage of chyme into the duodenum 114 results in the release of enzyme rich pancreatic secretions from the pancreas 115 and bile salt rich biliary secretions from the liver 116. The biliary secretions travel through the common bile duct 117 where they combine with the pancreatic secretions arriving through the pancreatic duct 118 and the two ducts combine to form the ampulla of vater 119. The ampulla of vater 119 serves as the entry point for the secretions to be deposited into the duodenum 114. In the jejunum 120, the mixing of pancreatic and biliary secretions with the chyme results in the digestion of proteins, fats, and carbohydrates, which are then absorbed into the blood stream.

Figure 2A:
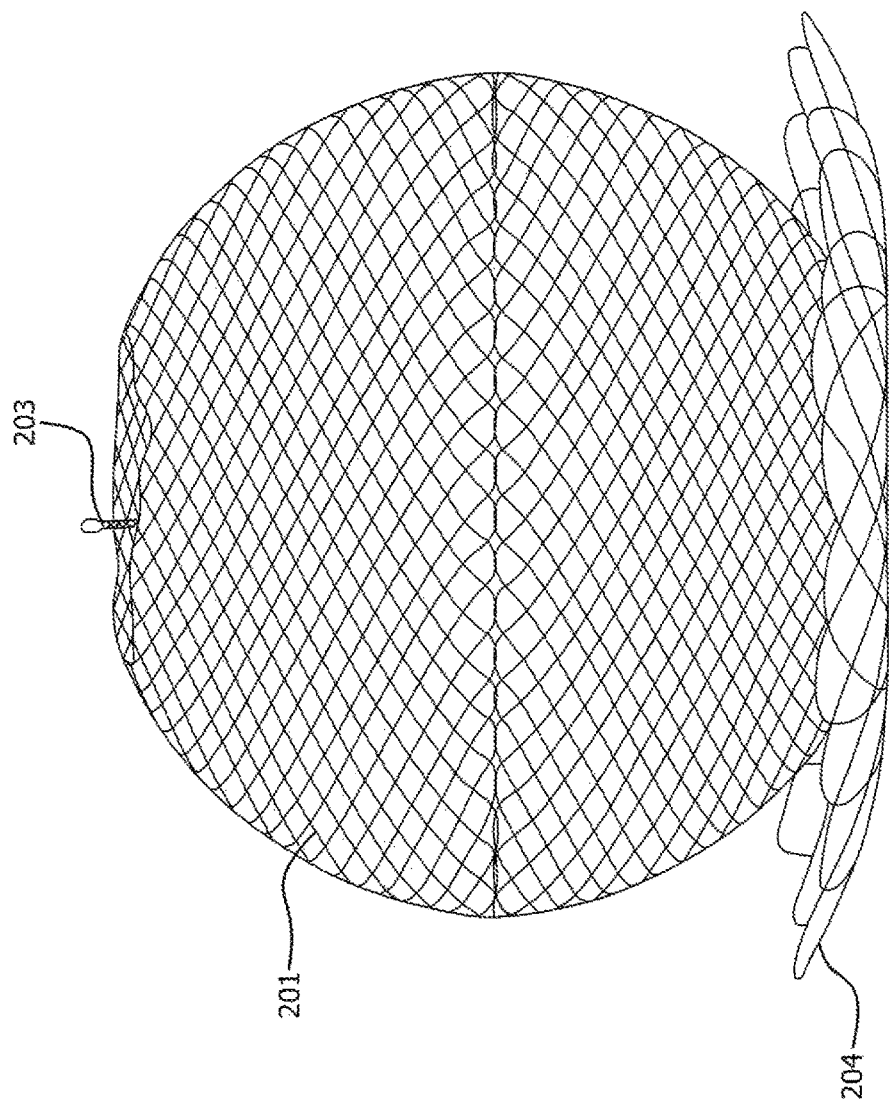
FIG. 2A is an illustration of a wire mesh structure in a post-deployment configuration with a proximally sloping anti-migration disc or collar attached to its distal end, in accordance with one embodiment of the present specification.

FIG. 2A is an illustration of a wire mesh structure 201 of an intragastric device in a post-deployment configuration with a proximally sloping anti-migration disc or collar 204 extending from or attached to its distal end, in accordance with one embodiment of the present specification. The wire mesh structure 201 comprises a three dimensional porous structure having an internal volume. The wire mesh structure 201 has an oval shape and includes a retrieval mechanism 203. In one embodiment, the retrieval mechanism is a silk suture loop. In one embodiment, the retrieval mechanism is an 80 lb. retrieval suture. The anti-migration collar 204 is proximally sloping in that it comprises a distal portion of the wire mesh structure 201 that is folded such that the distally directed end of the wire mesh structure 201 is made to point toward the proximal end of the wire mesh structure 201. In other embodiments, the collar 204 comprises any curved/atraumatic structure positioned circumferentially around the distal end of the wire mesh structure 201. The collar 204 helps prevent the wire mesh structure 201 from entering and passing through the pylorus. In one embodiment, the wire mesh structure 201 includes a bulbous, predominantly spherical or ovoid proximal end and an expanded distal end. In one embodiment, the distal half of the structure is covered with a membrane to impede the passage of food out of the structure 201, directing the food through a distal opening. In one embodiment, the structure 201 has an optional anti-reflux valve at the proximal end and another optional valve at the distal end. The valve at the distal end acts to control the flow of chyme or partially digested food from the inside of the structure 201 to the outside of the structure 201.

Figure 2B:
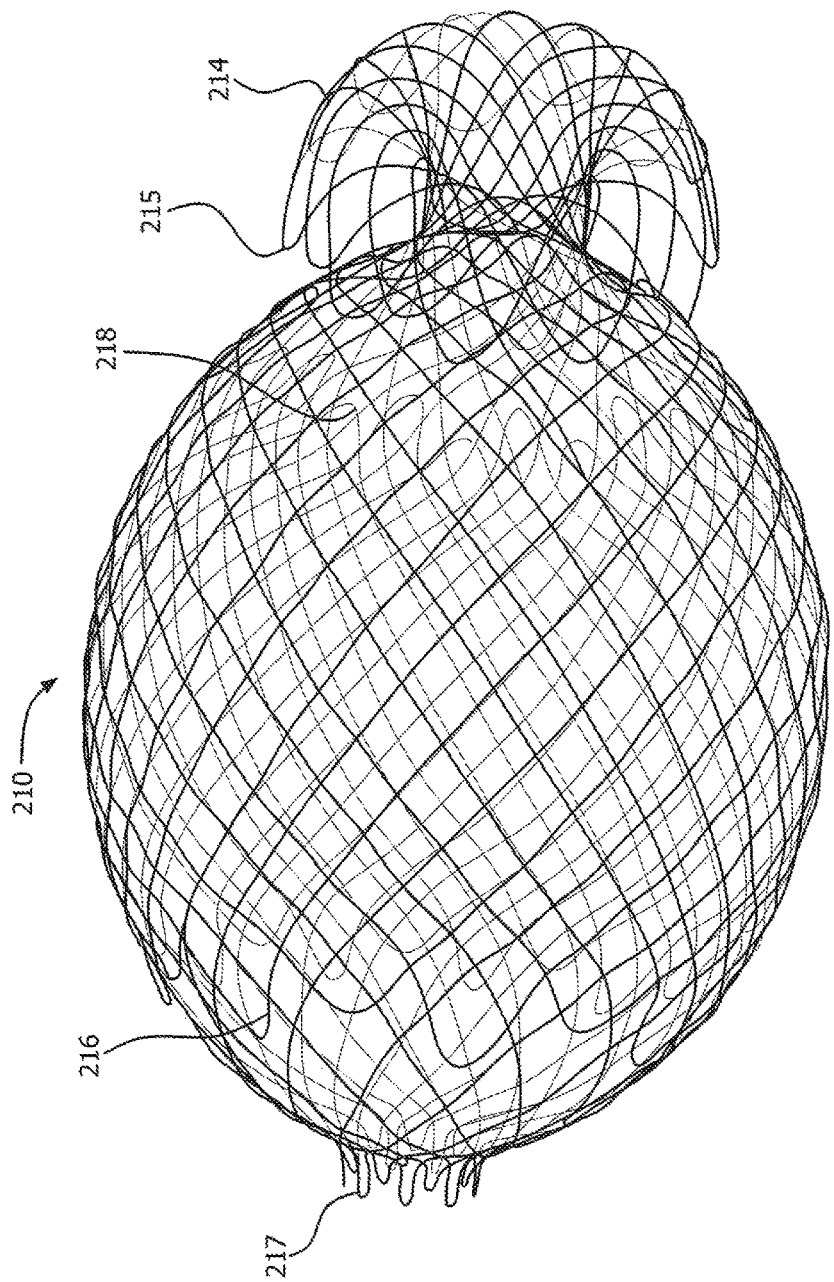
FIG. 2B is an illustration of a wire mesh structure in a post-deployment configuration with a proximally curving anti-migration collar formed at its distal end, in accordance with one embodiment of the present specification.

FIG. 2B is an illustration of a wire mesh structure 210 in a post-deployment configuration with a proximally curving anti-migration collar 214 formed at its distal end, in accordance with one embodiment of the present specification. The wire mesh structure 210 has an oval shape with a proximal end and a distal end. The wire mesh structure 210 includes staggered nodes 216, 218 within its body to facilitate compression for delivery and removal. The wire mesh structure 210 also includes a set of staggered nodes 217 at its proximal end. The staggered nodes 217 at the proximal end provide a location for grasping, thereby enhancing ease of retrieval. The anti-migration collar 214 is formed from a continuation of the wire of the wire mesh structure 210 at its distal end. The anti-migration collar 214 bends proximally, toward the body of the wire mesh structure 210, and its ends 215 are formed in a rounded fashion to be atraumatic to body tissues. In various embodiments, the wire mesh structure 210 has no sharp edges, preventing the occurrence of abrasions, and a radial force high enough to prevent any significant or permanent deformation by gastric contractions and passage through the pylorus, but low enough such that the wire mesh structure 210 is not too rigid, allowing it to be affected by gastric contractions enough to facilitate movement of food through the wire mesh structure 210. In some embodiments, the wire mesh structure can withstand a contractile force up to 200 mm Hg without being completely compressed.

Figure 3A:
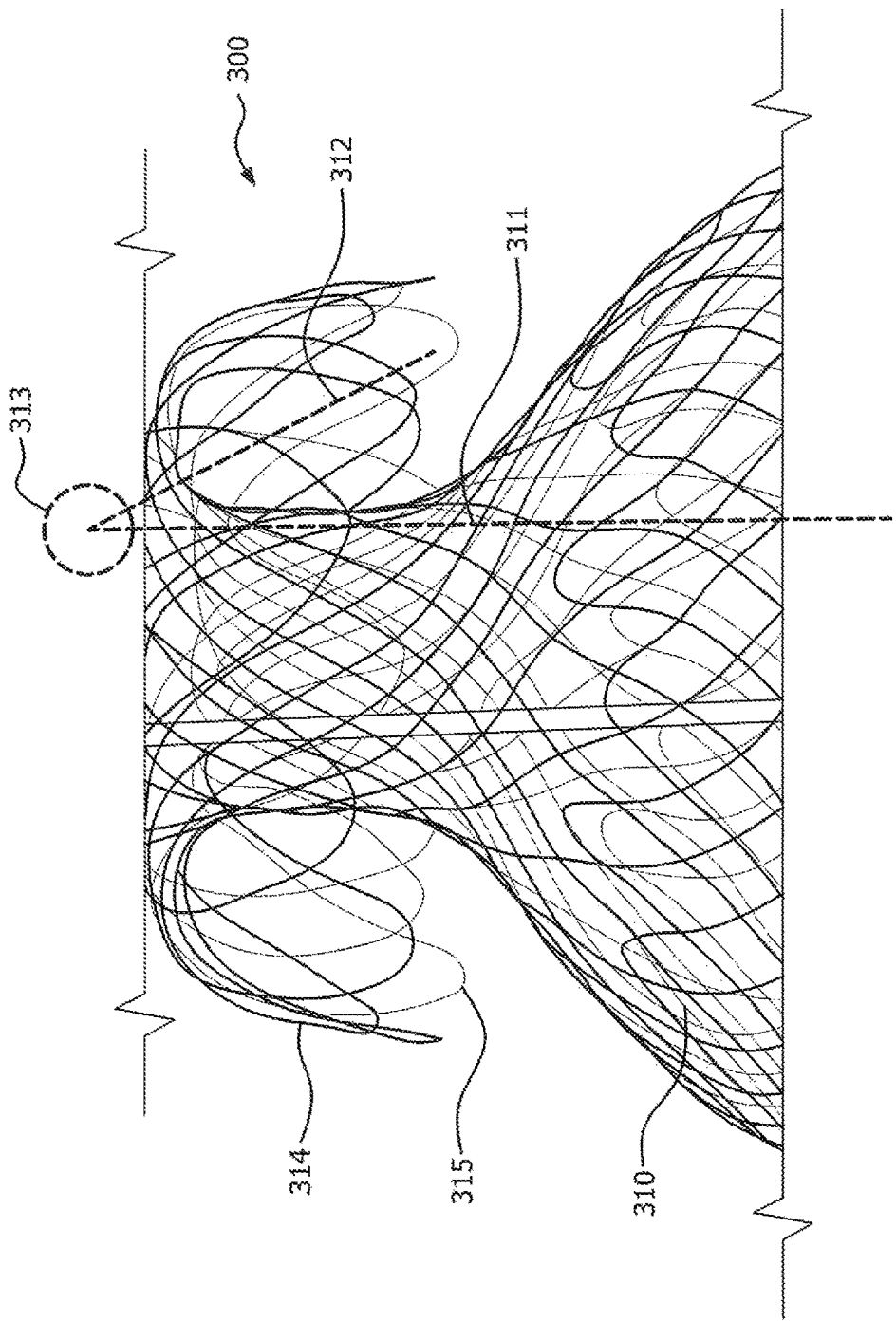
FIG. 3A is a close-up illustration of an atraumatic anti-migration collar of a wire mesh structure of an intragastric device, in accordance with one embodiment of the present specification.

FIG. 3A is a close-up illustration of an atraumatic anti-migration collar 314 of a wire mesh structure 310 of an intragastric device 300, in accordance with one embodiment of the present specification. The anti-migration collar 314 has a toroid bulb shape and comprises rounded ends 315 which extend proximally toward the wire mesh structure 310. The rounded ends 315 are designed to be atraumatic to body tissues. As discussed above, in some embodiments, the ends 315 are separated into various nodes to prevent bunching of the wires when compressed, which could lead to erosions. The long axis of the collar 312 is curved at an angle 313 greater than 90° compared to the long axis of the mesh 311 such that the rounded ends 315 are pointing in the direction toward the wire mesh structure 310.

Figure 3B:
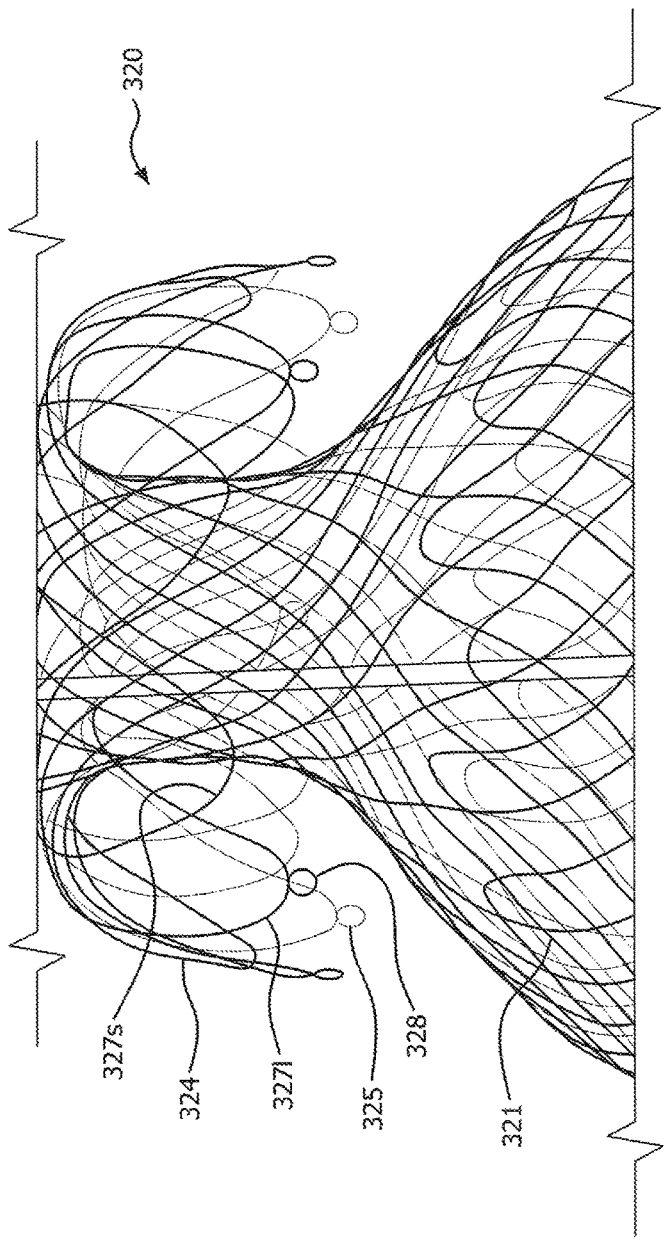
FIG. 3B is a close-up illustration of an atraumatic anti-migration collar of a wire mesh structure of an intragastric device, in accordance with another embodiment of the present specification.
Figure 3D:
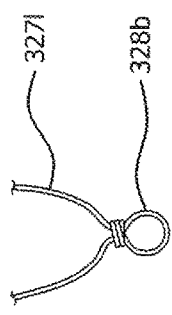
FIG. 3D is an illustration of hoops formed from separate wire hoops that are sutured to the free ends of the long nodes in accordance with one embodiment of the specification.
Figure 3C:
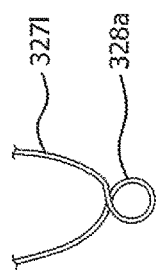
FIG. 3C is an illustration of hoops formed by twisting the free ends of long nodes into a hoop shape in accordance with one embodiment of the present specification.

FIG. 3B is a close-up illustration of an atraumatic anti-migration collar 324 of a wire mesh structure 321 of an intragastric device 320, in accordance with another embodiment of the present specification. The anti-migration collar 324 has a toroid bulb shape and comprises rounded ends 325 which extend proximally toward the wire mesh structure 321. The rounded ends 325 are designed to be atraumatic to body tissues. In some embodiments, the ends 325 are separated into various nodes 327*l*, 327*s* to prevent bunching of the wires when compressed, which could lead to erosions. The nodes include long nodes 327*l* and short nodes 327*s*, wherein the long nodes 327*l* extend further in a proximal direction back toward the top of the wire mesh structure 321 than the short nodes 327*s*. In some embodiments, the collar 324 includes 9 long nodes 327*l* and 9 short nodes 327*s*. The free ends of the long nodes 327*l* include hoops 328 for suturing a proximal end of a sleeve component. The hoops 328 extend outward away from the free ends of the long nodes 327*l*. In one embodiment, hoops 328*a* (FIG. 3C) are formed from twisting the free ends of the long nodes 327*l* into a hoop shape. In another embodiment, hoops 328*b* (FIG. 3D) comprise separate wire hoops that are sutured to the free ends of the long nodes 327*l*. In some embodiments, once the sleeve is attached, additional suture knots are placed at the junction of the twist or separate wire hoop to prevent sliding of the sleeve attachment.

In some embodiments, a sleeve component is attached to the distal end of the wire mesh structure or the collar of the intragastric device. In various embodiments, the sleeve component of the present specification is made of polytetrafluoroethylene (PTFE) or polyethylene or cast PTFE (e.g., Teflon), PTFE with fluorinated ethylene propylene (FEP) or perfluoroalkoxy (PFA) coating, PFA, extruded FEP and extruded PFA or extruded PTFE or a fluoropolymer or silicone. In one embodiment, a silicone sleeve is manufactured by hand pouring and braiding. In another embodiment, a silicone sleeve is manufactured by machine braiding. In various embodiments, the sleeve component has a length in a range of 6 inches to 6 feet or longer. In one embodiment, the sleeve component has a length of 24 inches. In another embodiment, the sleeve component has a length of 30 inches. In various embodiments, the sleeve component has a diameter in a range of 1 cm to 10 cm. In one embodiment, the sleeve component has a diameter of 3 cm.

FIG. 4A is an illustration of a portion of a sleeve component 400 of an intragastric device in a post-deployment configuration in accordance with one embodiment of the present specification, depicting a single wire support 401 spiraling along the body of the sleeve 400. The metal wire needs to have a tight enough spiral to provide support but must not be too tight such that, once the sleeve in compressed for delivery, it becomes kinked and cannot regain its full shape. Referring to FIG. 4A, the spiral metal wire 401 has a pitch depicted by length/which is equal to 60 mm. With a wire thickness of 0.1 to 1 mm, this pitch gives the spiral metal wire a strain percentage that will be no more than 20%, and preferably less than 8%.

FIG. 4B is an illustration of a portion of a sleeve component 405 of an intragastric device in a post-deployment configuration in accordance with one embodiment of the present specification, depicting multiple wire supports 406, 407, 408 spiraling along the body of the sleeve 405. The sleeve includes more than one spiral metal wire to provide greater support while still preventing permanent kinking. Referring to FIG. 4B, each individual wire 406, 407, 408 has a pitch depicted by length $l_1$ which is equal to 60 mm. The wires 406, 407, 408 are spaced such that the pitch between two separate wires, depicted by length $l_2$, is equal to 20 mm.

Figure 4C:
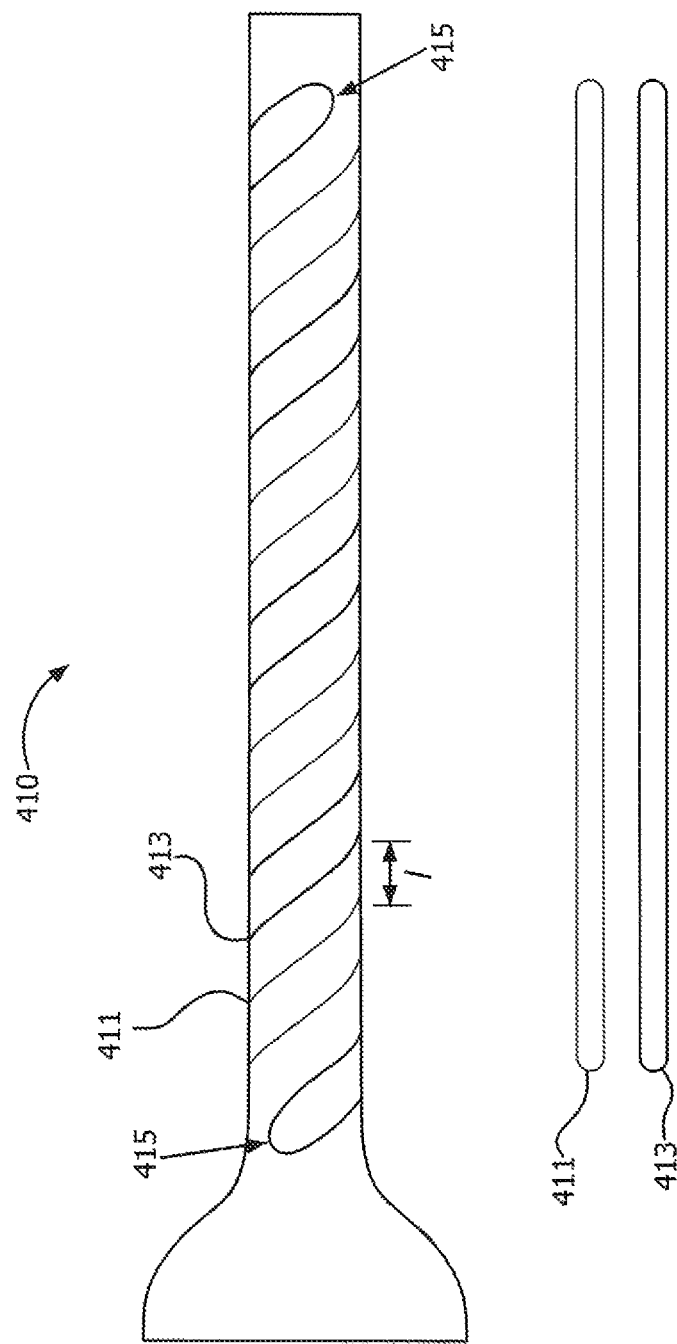
FIG. 4C is an illustration of a funnel shaped sleeve component of an intragastric device in a post-deployment configuration in accordance with one embodiment of the present specification, depicting spiral wire loop supports on the sleeve.

FIG. 4C is an illustration of a funnel shaped sleeve component 410 of an intragastric device in a post-deployment configuration in accordance with one embodiment of the present specification, depicting spiral wire loop supports 411, 413 on the sleeve 410. In the embodiment depicted in FIG. 4C, the sleeve 410 includes two sets of wire loop supports 411, 413. Each set of wire loop supports 411, 413 includes a loop comprising two individual wires, for a total of four wires on the sleeve 410. Each wire loop support 411, 413 is finished with blunted ends 415 to be atraumatic to body tissues. The wire loop supports 411, 413 are twisted into a spiral configuration and looped along the length of the sleeve 410. In one embodiment, the pitch, or distance between each loop 411, 413 (and between each wire of each loop 411, 413) is defined by length/and is approximately 15 mm.

In one embodiment, the opening of the funnel shaped sleeve is well suited for attachment to the nodes of the collar positioned at the distal end of the wire mesh structure of some embodiments of the intragastric device.

Figure 5:
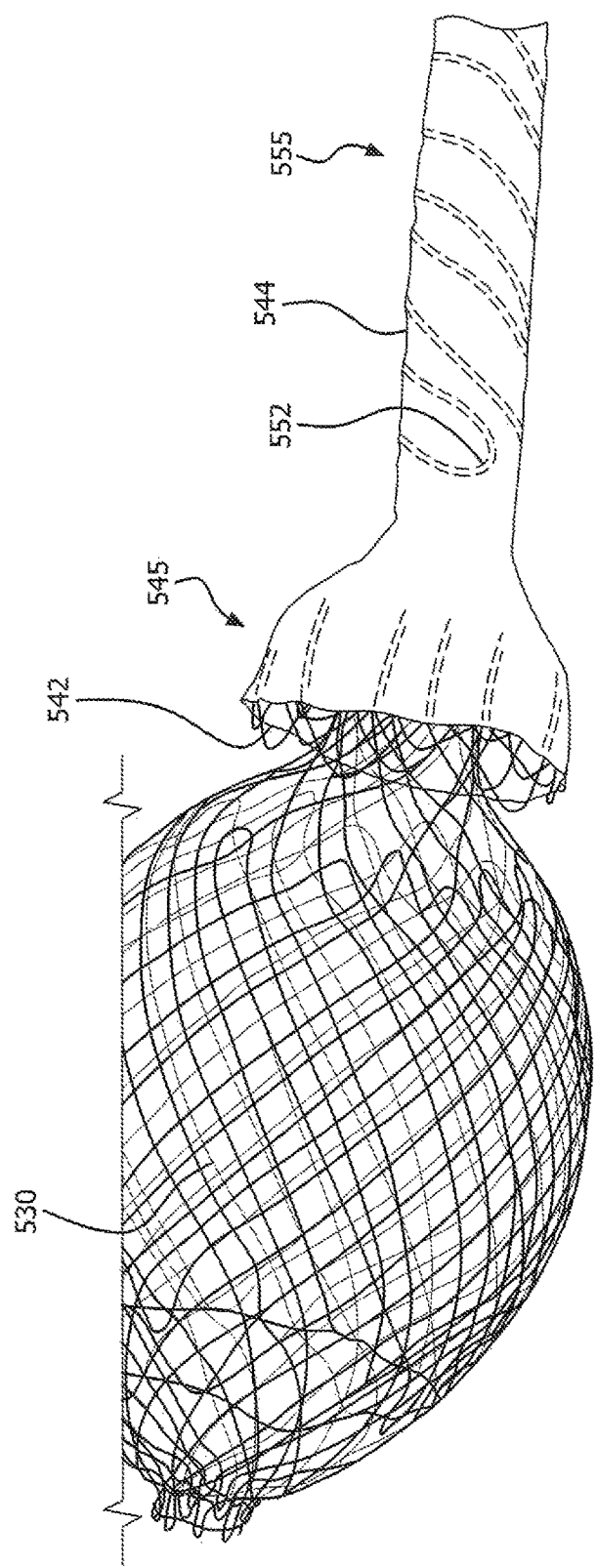
FIG. 5 is an illustration of a wire mesh structure with attached sleeve component in a post-deployment configuration in accordance with one embodiment of the present specification, depicting a blunt end of a wire mesh support toward the proximal end of the sleeve.

FIG. 5 is an illustration of a wire mesh structure 530 with attached sleeve component 544 in a post-deployment configuration in accordance with one embodiment of the present specification, depicting a blunt end 552 of a wire mesh support toward the proximal end of the sleeve 544. The sleeve 544 is connected to a proximally curving, atraumatic anti-migration collar 542 at the distal end of the wire mesh structure 530 and includes a proximal section 545 having four layers and a center section 555 having three layers.

Figure 6:
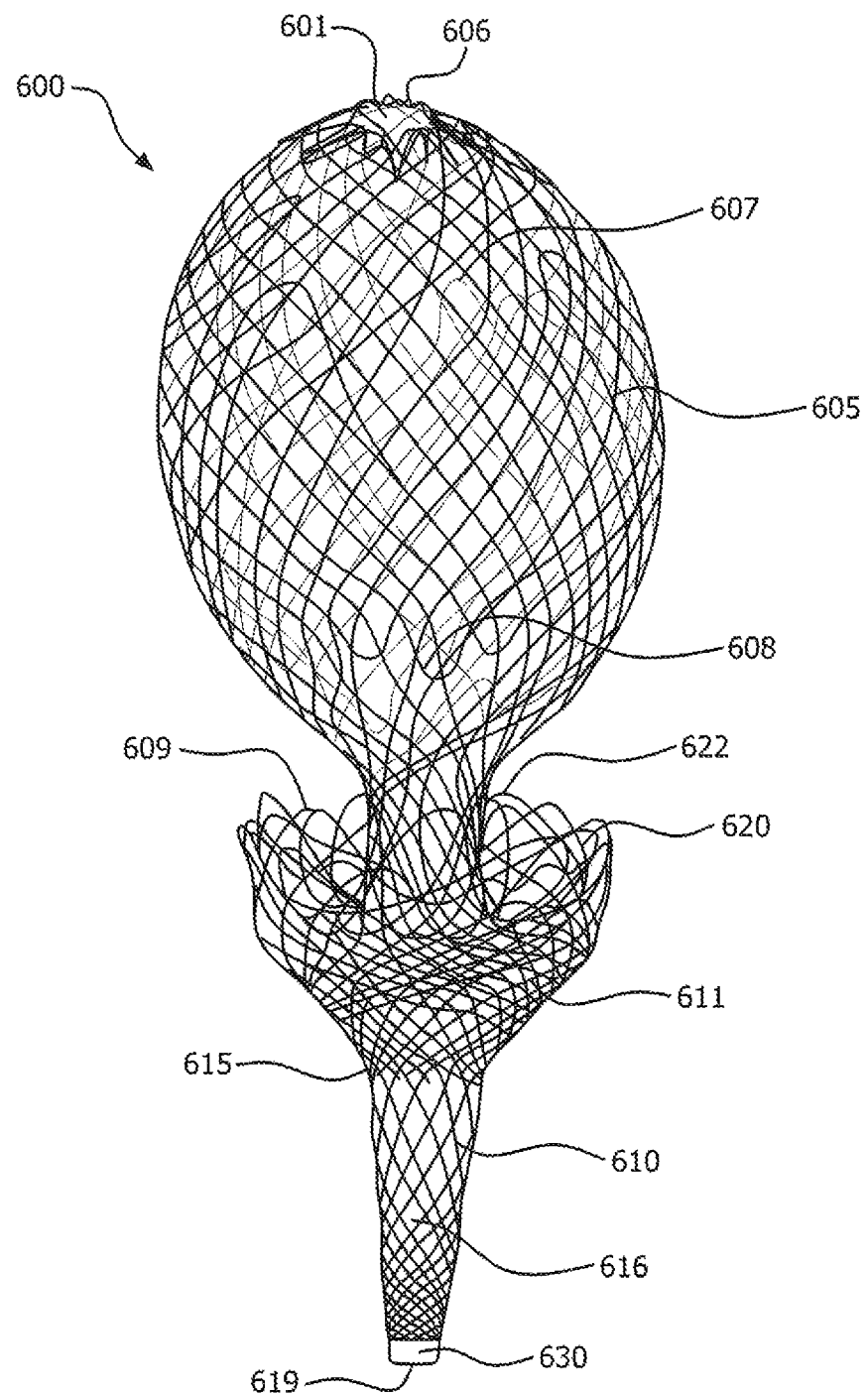
FIG. 6 is an illustration of an intragastric device with a funnel shaped sleeve in a post-deployment configuration, in accordance with one embodiment of the present specification.

FIG. 6 is an illustration of an intragastric device 600 with a funnel shaped sleeve 610 in a post-deployment configuration, in accordance with one embodiment of the present specification. The intragastric device 600 includes a wire mesh structure 605 having a proximal end and a distal end with an anti-migration collar 620 formed at said distal end. The sleeve 610 includes a proximal end and a distal end and is attached via its proximal end to the anti-migration collar 620.

The wire mesh structure 605 comprises at least one metal wire folded about itself to create a crisscross weave pattern with a plurality of free curved ends, or nodes, along the structure. In its expanded, post-deployment configuration, the wire mesh structure 605 has an oval shape. To facilitate optimal expansion and compression for easier delivery and removal, the wire mesh structure 605 includes a plurality of staggered nodes 606, 607, 608, 609 along its length. A first set of staggered nodes 606 is positioned at the proximal end of the wire mesh structure 605 and circumscribes a first opening 601. In one embodiment, each node in said first set of staggered nodes 606 is bent upwards to extend in a direction opposite from an interior of the wire mesh structure 605. The nodes in said first set of staggered nodes 606 are used as grasping points for a retrieval device during removal of the intragastric device 600. The wire mesh structure 605 includes a second set of staggered nodes 607 distal to said first set 606 and proximal to a midpoint of said wire mesh structure 605. A third set of staggered nodes 608 is positioned distal to said midpoint and proximal to the distal end of the wire mesh structure 605. A fourth set of staggered nodes 609 is positioned at the distal end of the wire mesh structure 605 and comprises the free end of the anti-migration component 620. All of the curves comprising the nodes in each set of staggered nodes 606, 607, 608, 609 are designed to have a bend that is atraumatic to body tissues. The nodes are staggered to prevent bunching of the bending points of the wire and bulking of the wire mesh structure as it is compressed to its pre-deployment configuration. Spreading the nodes along the length of the wire mesh structure allows for an overall smaller diameter of the device once it is compressed.

The sleeve 610 includes a proximal portion 611 and a distal portion 616 which join at a transition point 615 along the sleeve 610 body. Both the proximal portion 611 and the distal portion 616 of the sleeve 610 are funnel shaped, each having a diameter that decreases as the portions 611, 616 extend distally. In one embodiment, the diameter of the proximal portion 611 is substantially the same as the diameter of the anti-migration collar 620 at a proximal end of said proximal portion 611. The diameter of the proximal portion 611 decreases as the proximal portion 611 extends distally until the sleeve 610 transitions into its distal portion 616, at which point the diameters of the proximal portion 611 and the distal portion 616 are equal. The diameter of the distal portion 616 then decreases as said distal portion 616 extends distally. The distal portion 616 of the sleeve 610 ends in a second opening 619 at a distal end of the intragastric device 600. In one embodiment, the proximal portion 611 has a length that is less than a length of the distal portion 616. In various embodiments, the funnel shaped sleeve 610 comprises at least one wire support. In some embodiments, the at least one wire support comprises the same wire(s) in both the proximal portion 611 and distal portion 616. In other embodiments, the proximal portion 611 and distal portion 616 comprise separate wire supports and the wires are joined together at a distal end of the proximal portion 611 and a proximal end of the distal portion 616. In one embodiment, the separate wires are spot welded together. The wire is folded upon itself to create a crisscross weave pattern in the sleeve 610. In both the proximal 611 and distal portions 616, the intersecting sections of the wire come closer to one another as the portions 611, 616 extend distally and the funnel shape narrows, such that the weave pattern becomes tighter at the distal ends of each portion 611, 616. The sleeve 610 includes curves or free ends, similar to the nodes of the wire mesh structure 605, at its proximal end and distal end. The free ends are designed to be atraumatic to body tissues. The free ends at the proximal end of the sleeve 610 are attached to the nodes of the fourth set of staggered nodes 609 of the wire mesh structure 605 via one or more sutures 622. The free ends at the distal end of the sleeve 610 circumscribe the second opening 619. In various embodiments, the sleeve 610 is a short sleeve having a total length in a range of 5 cm-120 cm. In one embodiment, the sleeve 610 is a short sleeve having a total length of 60 cm. In one embodiment, the sleeve 610 includes a soft atraumatic tip 630 at its distal end. The tip 630 contains no wires and is included to prevent injury to the intestinal mucosa from the sleeve tip.

When the sleeve 610 is attached to the wire mesh structure 605, the proximal end of the proximal portion 611 of the sleeve 610 is slid over and covers at least a portion of the anti-migration component 620 such that the proximal portion 611 of the sleeve 610 covers an opening at the distal end of the wire mesh structure. This positioning enables fluid communication between the interior of the wire mesh structure 605 and an interior of the sleeve 610 and establishes a pathway for food from said first opening 601, into said interior of said wire mesh structure 605, through said interior of said sleeve 610, and out of said second opening 619.

Figure 7:
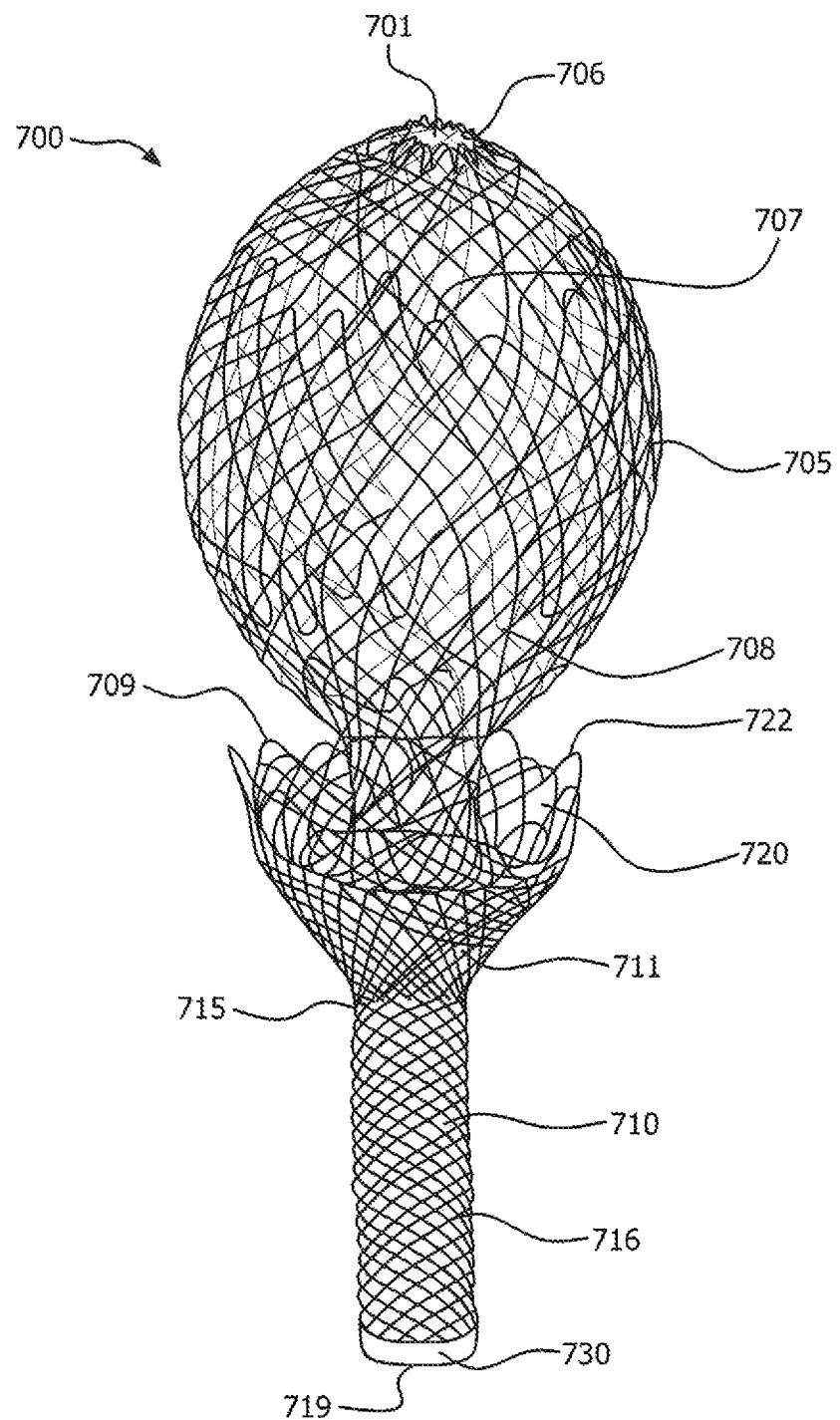
FIG. 7 is an illustration of an intragastric device with a cylindrically shaped sleeve in a post-deployment configuration, in accordance with one embodiment of the present specification.

FIG. 7 is an illustration of an intragastric device 700 with a cylindrically shaped sleeve 710 in a post-deployment configuration, in accordance with one embodiment of the present specification. The intragastric device 700 includes a wire mesh structure 705 having a proximal end and a distal end with an anti-migration collar 720 formed at said distal end. The sleeve 710 includes a proximal end and a distal end and is attached via its proximal end to the anti-migration collar 720. In one embodiment, the sleeve 710 includes a soft atraumatic tip 730 at its distal end. The tip 730 contains no wires and is included to prevent injury to the intestinal mucosa from the sleeve tip.

The wire mesh structure 705 is similar to the structure 605 discussed with reference to FIG. 6 and includes an oval shape with a crisscross weave pattern, a plurality of staggered nodes 706, 707, 708, 709, and a first opening 701 at its proximal end. All of the curves comprising the nodes in each set of staggered nodes 706, 707, 708, 709 are designed to have a bend that is atraumatic to body tissues.

The sleeve 710 includes a proximal portion 711 and a distal portion 716 which join at a transition point 715 along the sleeve 710 body. The proximal portion 711 of the sleeve 710 is funnel shaped and includes a diameter that decreases as the portion 711 extends distally. In one embodiment, the diameter of the proximal portion 711 is substantially the same as the diameter of the anti-migration collar 720 at a proximal end of said proximal portion 711. The diameter of the proximal portion 711 decreases as the proximal portion 711 extends distally until the sleeve 710 transitions into its distal portion 716, at which point the diameters of the proximal portion 711 and the distal portion 716 are equal. The diameter of the distal portion 716 then continues at the same size as said distal portion 716 extends distally, giving the distal portion 716 a substantially cylindrical shape. The distal portion 716 of the sleeve 710 ends in a second opening 719 at a distal end of the intragastric device 700. In one embodiment, the proximal portion 711 has a length that is less than a length of the distal portion 716.

In various embodiments, the funnel shaped proximal portion 711 of the sleeve 710 comprises at least one wire support. The wire is folded upon itself to create a crisscross weave pattern in the sleeve 710. The intersecting sections of the wire come closer to one another as the portion 711 extends distally and the funnel shape narrows, such that the weave pattern becomes tighter at the distal end of the proximal portion 711. In various embodiments, the distal portion 716 includes at least one helical wire support extending along its cylindrical length. The helical wire support has a consistent pitch such that a resultant helical weave structure has the same pattern along the length of the distal portion 716 of the sleeve 710. In some embodiments, the helical wire support of the distal portion 716 is an extension of the at least one wire support of the proximal portion 711. In other embodiments, the proximal portion 711 and distal portion 716 comprise separate wire supports and the wires are joined together at a distal end of the proximal portion 711 and a proximal end of the distal portion 716. In one embodiment, the separate wires are spot welded together.

The sleeve 710 includes curves or free ends, similar to the nodes of the wire mesh structure 705, at its proximal end and distal end. The free ends are designed to be atraumatic to body tissues. The free ends at the proximal end of the sleeve 710 are attached to the nodes of the fourth set of staggered nodes 709 of the wire mesh structure 705 via one or more sutures 722. The free ends at the distal end of the sleeve 710 circumscribe the second opening 719. In various embodiments, the sleeve 710 is a short sleeve having a total length in a range of 5 cm-120 cm. In one embodiment, the sleeve 710 is a short sleeve having a total length of 60 cm. The funnel shaped conical section can vary from being 1% of the total sleeve length to being 100% of the total sleeve length.

When the sleeve 710 is attached to the wire mesh structure 705, the proximal end of the proximal portion 711 of the sleeve 710 is slid over the anti-migration component 720 such that the proximal portion 711 of the sleeve 710 covers an opening at the distal end of the wire mesh structure. This positioning enables fluid communication between the interior of the wire mesh structure 705 and an interior of the sleeve 710 and establishes a pathway for food from said first opening 701, into said interior of said wire mesh structure 705, through said interior of said sleeve 710, and out said second opening 719.

Figure 8A:
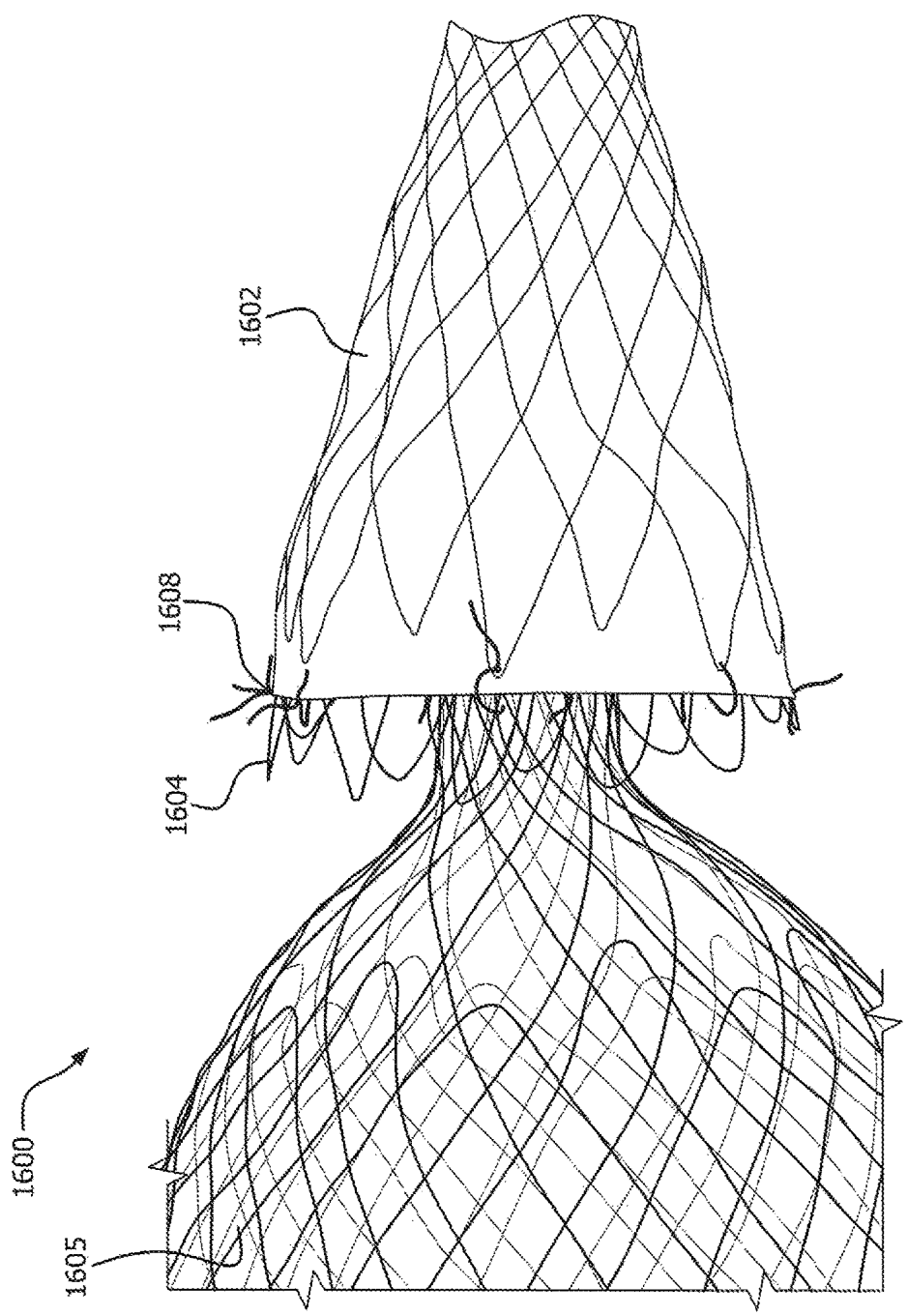
FIG. 8A is a close-up illustration of a funnel shaped sleeve attached to an anti-migration collar of a wire mesh structure of an intragastric device, in accordance with one embodiment of the present specification.

FIG. 8A is a close-up illustration of a funnel shaped sleeve 802 attached to an anti-migration collar 804 of a wire mesh structure 805 of an intragastric device 800, in accordance with one embodiment of the present specification. The sleeve 802 is attached to the anti-migration collar 804 via a plurality of sutures 808.

Figure 8B:
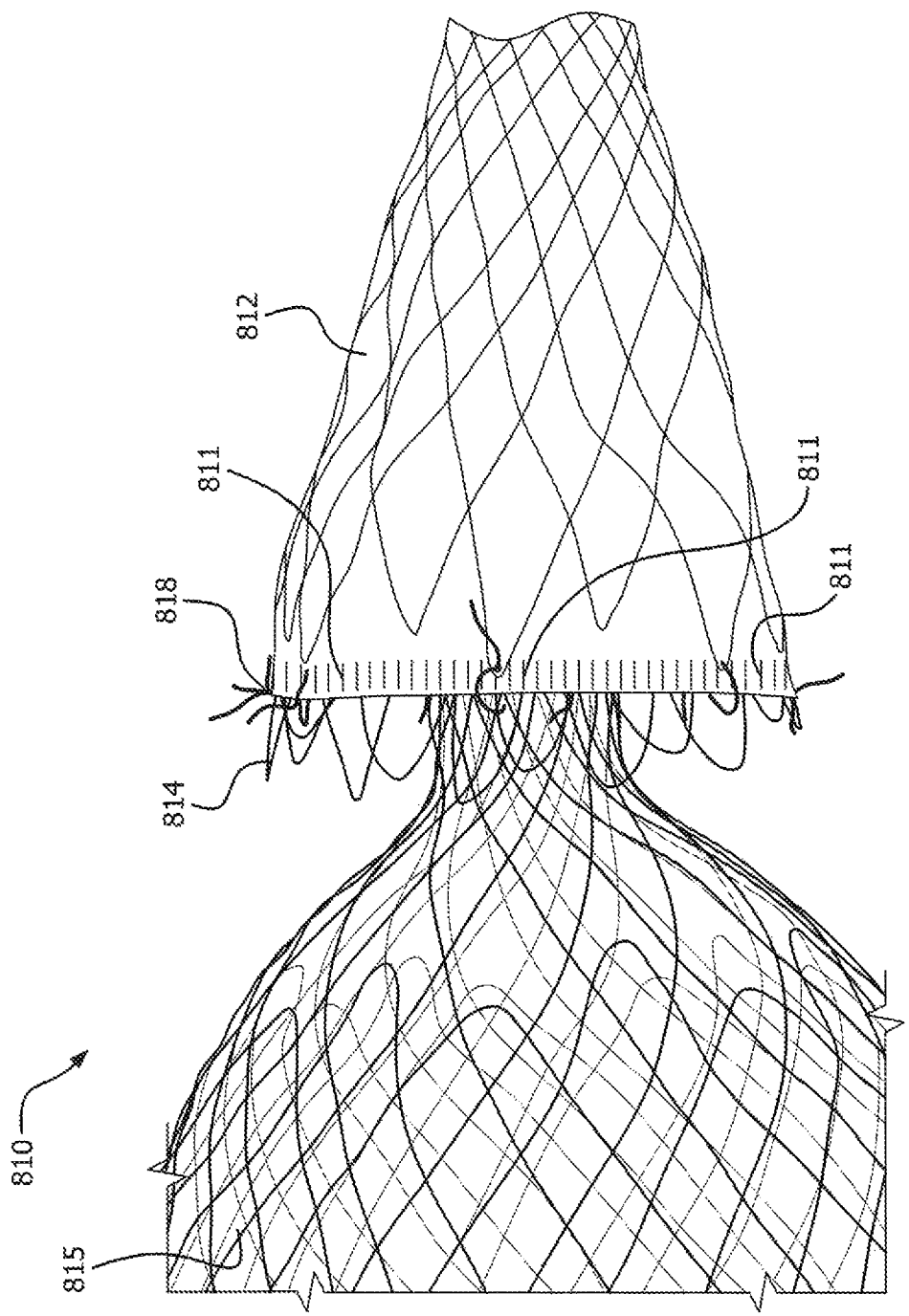
FIG. 8B is a close-up illustration of a funnel shaped sleeve attached to an anti-migration collar of a wire mesh structure of an intragastric device and having a proximal sleeve end having frayed edges, in accordance with another embodiment of the present specification.

FIG. 8B is a close-up illustration of a funnel shaped sleeve 812 attached to an anti-migration collar 814 of a wire mesh structure 815 of an intragastric device 810, in accordance with another embodiment of the present specification. The sleeve 812, attached to the anti-migration collar 814 via a plurality of sutures 818, includes a plurality of frayed edges 811 at its proximal end to make said edges less traumatic to body tissues.

FIG. 8C is an illustration of an intragastric device 820 comprising a wire mesh structure 825 and attached sleeve 822, in accordance with one embodiment of the present specification. The wire mesh structure 825 is anchorless and includes atraumatic wire ends. In one embodiment, the wire mesh structure 825 is composed of Nitinol. The wire mesh structure 825 includes an anti-migration collar 824 to which the sleeve 822 is attached. In some embodiments, the wire mesh structure 825 includes retrieval drawstrings positioned proximate its proximal end, as depicted with reference to FIG. 8E. The sleeve 822 comprises an anchorless, impermeable, fluoropolymer liner designed to extend into the proximal portion of the small bowel, particularly the mid-duodenum. In various embodiments, the sleeve 822 includes an embedded Nitinol stent structure within polymer layers such that the sleeve 822 is atraumatic and no portion of the Nitinol comes into contact with the small intestine. In one embodiment, the sleeve 822 includes radiopaque markers for assistance with proper delivery and placement.

The wire mesh structure 825 is anchorless and occupies a space within the stomach. The wire mesh structure 825 is free to float within the stomach and intermittently exerts gentle, atraumatic stretching forces on a portion of the stomach as it comes into contact with the inner stomach wall. The stretching forces induce the sensation of satiety in the patient. The anti-migration collar 824 is appropriately shaped to receive the attached sleeve 822. Gastric contents enter the wire mesh structure 825 through a first opening 821 at the proximal end of the wire mesh structure 825 or through openings 829 between the wires of the wire mesh structure 825 and are directed into the attached sleeve 822. The gastric contents then pass through the sleeve 822 and empty out a second opening 823 at the distal end of the sleeve 822, either into the duodenum or jejunum, depending on the length of the sleeve 822. The sleeve 822 is pre-attached to the anti-migration collar 824 of the wire mesh structure 825. The Nitinol stent structure embedded in the sleeve 822 provides support to the sleeve 822 and prevents it from torsion or being kinked by actions of the intestinal musculature. Additionally, the Nitinol stent structure provides a gentle, radial stretching force on the small intestinal wall, inducing a sensation of satiety in the patient and preventing the passage of chyme around the sleeve 822.

FIG. 8D is an illustration of the intragastric device 820 of FIG. 8C with the sleeve 822 straightened to depict the device 820 dimensions relative to the surrounding anatomy. The sleeve 822 includes a proximal, funnel or cone shaped portion 822p attached to the anti-migration collar of the wire mesh structure 825 and a distal, cylindrically shaped portion 822d extending distally from said proximal portion 822p. The wire mesh structure 825 and proximal portion 822p of the sleeve 822 are configured to reside in the stomach of the patient and together have a maximum outer diameter of approximately 8 inches and a length $l_1$. In some embodiments, length $l_1$ is approximately 10 inches. In some embodiments, the volume of a fully deployed wire mesh structure 825 is approximately 1 liter. The proximal portion 822p of the sleeve 822 and the distal portion 822d of the sleeve 820 meet at a junction point 822j which is configured to sit at the patient's pylorus. The distal portion 822d of the sleeve 820 is configured to reside in the small intestine of the patient, particularly the duodenum, and has a maximum outer diameter of approximately 1.0 inches and a length $l_2$. In some embodiments, length $l_2$ is approximately 10 to 25 inches. In some embodiments, the length $l_2$ of the distal portion 822d is such that the distal end of the sleeve 822 is positioned in the duodenum so gastric contents pass from the stomach, through the device 820, and directly into the duodenum, bypassing the pylorus. In other embodiments, the length $l_2$ is such that the distal end of the sleeve 822 is positioned in the jejunum so gastric contents pass from the stomach, through the device 820, and directly into the jejunum, bypassing the pylorus and duodenum. In other embodiments, the wire mesh structure has a maximum diameter of 18 inches, a maximum length of 24 inches, and a maximum volume of 2.5 liters.

Figure 8E:
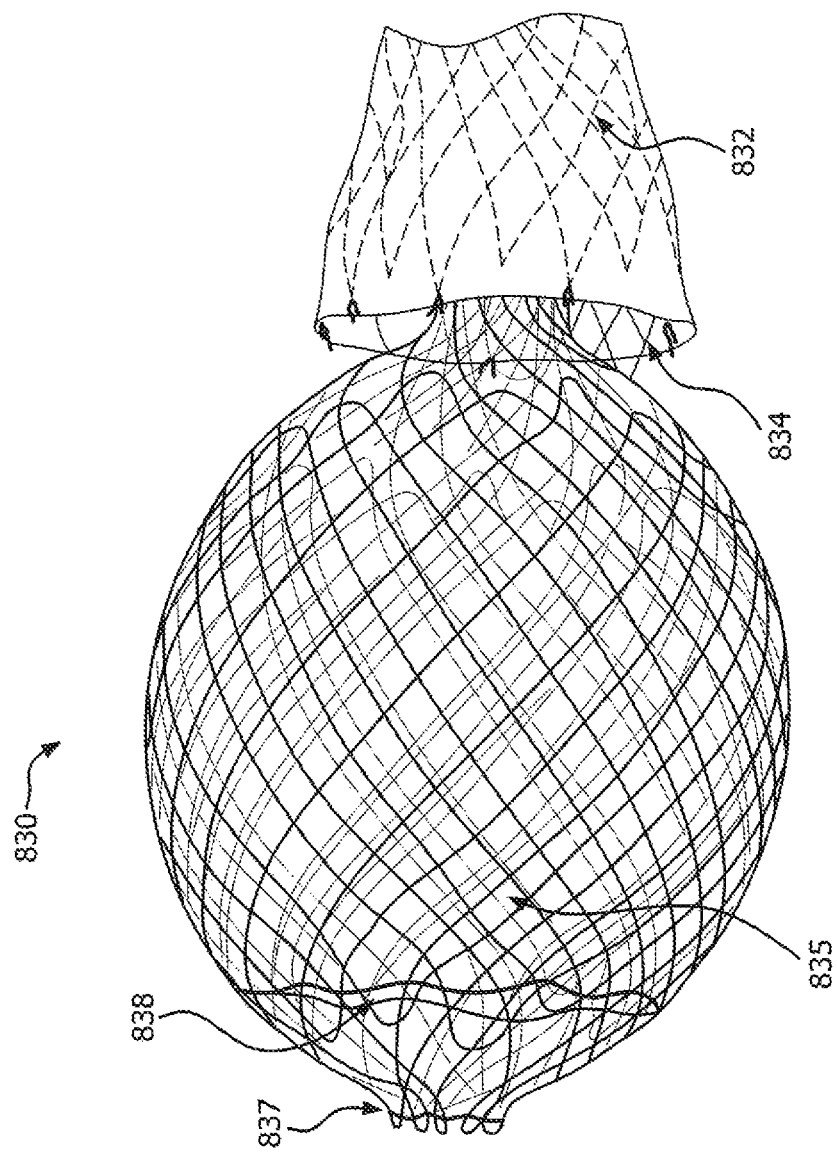
FIG. 8E is an illustration of a wire mesh structure and sleeve of an intragastric device, depicting retrieval drawstrings on said wire mesh structure, in accordance with one embodiment of the present specification.

FIG. 8E is an illustration of a wire mesh structure 835 and sleeve 832 of an intragastric device 830, depicting retrieval drawstrings 837, 838 on said wire mesh structure 835, in accordance with one embodiment of the present specification. The sleeve 832 is attached to an anti-migration collar 834 at the distal end of the wire mesh structure 835. In some embodiments, the anti-migration collar 834 includes loops in the wires of the nodes at the distal end of the nodes, as seen with reference to FIG. 4C, and the sleeve 832 is sutured to the anti-migration collar 834 at these loops. In the pictured embodiment, a pair of retrieval drawstrings 837, 838 are located on the wire mesh structure 835 proximate its proximal end. A first drawstring 837 is positioned at the proximal end of the wire mesh structure 835 and the second drawstring 838 is positioned distal to the first drawstring 837 but still proximate the proximal end of the wire mesh structure 835. The retrieval drawstrings 837, 838 pass through the openings between the wires of the wire mesh structure 835. During retrieval, free ends of the retrieval drawstrings 837, 838 are pulled on using a grasper to constrict the wire mesh structure 835 to a smaller outer diameter so it may be removed from the patient through an endoscope. In one embodiment, the two drawstrings 837, 838 are interconnected operably such that constricting one drawstring results in the other drawstring constricting simultaneously.

Figure 8F:
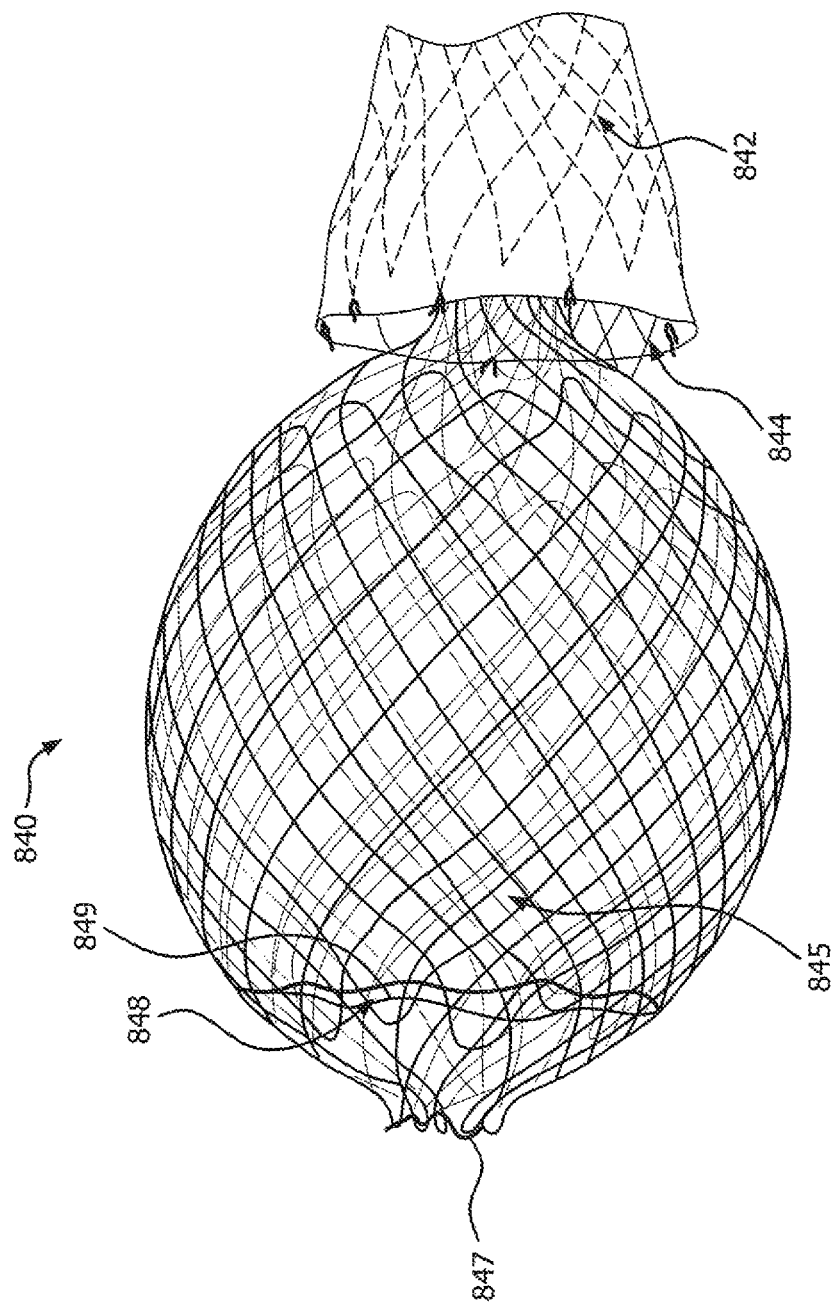
FIG. 8F is an illustration of a wire mesh structure and sleeve of an intragastric device, depicting a single retrieval drawstring on said wire mesh structure, in accordance with one embodiment of the present specification.

FIG. 8F is an illustration of a wire mesh structure 845 and sleeve 842 of an intragastric device 840, depicting a single retrieval drawstring 848 on said wire mesh structure 845, in accordance with one embodiment of the present specification. The sleeve 842 is attached to an anti-migration collar 844 at the distal end of the wire mesh structure 845. In some embodiments, the anti-migration collar 844 includes loops in the wires of the nodes at the distal end of the nodes, and the sleeve 842 is sutured to the anti-migration collar 844 at these loops. In the pictured embodiment, a single retrieval drawstring 848 is located on the wire mesh structure 845 proximate its proximal end. The retrieval drawstrings 848 passes through the openings between the wires of the wire mesh structure 845. During retrieval, free ends of the retrieval drawstring 848 are pulled on using a grasper to constrict the wire mesh structure 845 to a smaller outer diameter so it may be removed from the patient through an endoscope. In the pictured embodiment, the single drawstring 848 is sufficient to constrict two pluralities of nodes 847, 849 on the wire mesh structure 845, a first plurality 847 at the proximal end of the wire mesh structure 845 and a second plurality 849 at the level of the drawstring 848. In other embodiments, a single drawstring is sufficient for constricting one or more than two pluralities of nodes on the wire mesh structure.

In some embodiments, wherein the sleeve includes metal wire supports, the ends of the wire or wires are designed to be atraumatic to body tissues. In various embodiments, the wire ends are blunted, folded upon the wire, or welded to other wire ends. In other embodiments, the distal end of the sleeve includes a component designed to make said distal end atraumatic to body tissues. FIG. 9A is a cross-sectional illustration of a distal end of a sleeve 905, depicting one embodiment of a component 910 designed to configure said distal end to be atraumatic to body tissues. The component 910 has a cylindrical shape with a proximal end 911, a distal end 919, and a lumen 916 within. The component 910 is open at both ends 911, 919. The lumen 916 of the component 910 is in fluid communication with a lumen 906 of the sleeve 905 to allow for food to pass through the wire mesh of the device, the sleeve 905, and the component 910. The distal end 919 is rounded into a blunt shape that is atraumatic to body tissues. An outer surface of the component 910 includes a groove 913 configured to receive a circular member or O-ring 914. To attach the component 910 to the sleeve 905, the distal end of the sleeve 905 is coaxially slid onto the proximal end 911 of the component 910 such that a portion of the sleeve 905 is positioned over said groove 913. The O-ring 914 is then placed over the sleeve 905 and into the groove 913, providing a robust connection of the sleeve 905 to the component 910. The distal sleeve end 907 is then folded in a proximal direction back toward the sleeve 905 body. In one embodiment, the component 910 includes a circular flange 912 which extends outwardly from the outer surface of the component 910 and then in a proximal direction. The flange 912 serves to cover any sharp ends present in the folded distal sleeve end 907 and further protect body tissues from trauma. In various embodiments, the component 910 has a length in a range of 5 mm to 500 mm, an outside diameter in a range of 3 mm to 30 mm, and an inside diameter in a range of 0.5 to 50 mm.

Figure 9B:
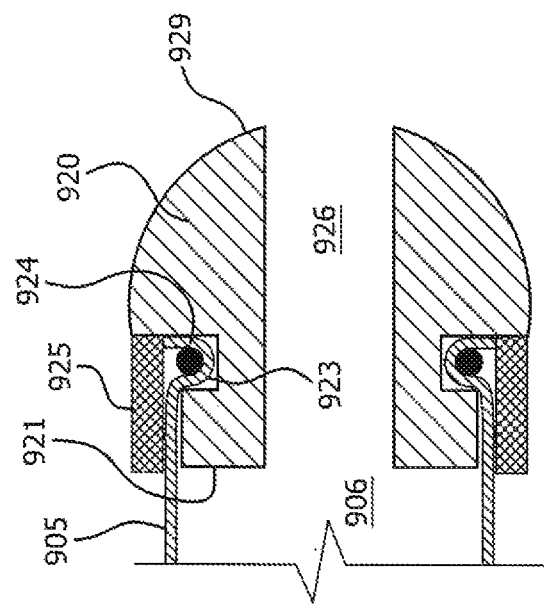
FIG. 9B is a cross-sectional illustration of a distal end of a sleeve, depicting another embodiment of a component designed to configure said distal end to be atraumatic to body tissues.
Figure 9A:
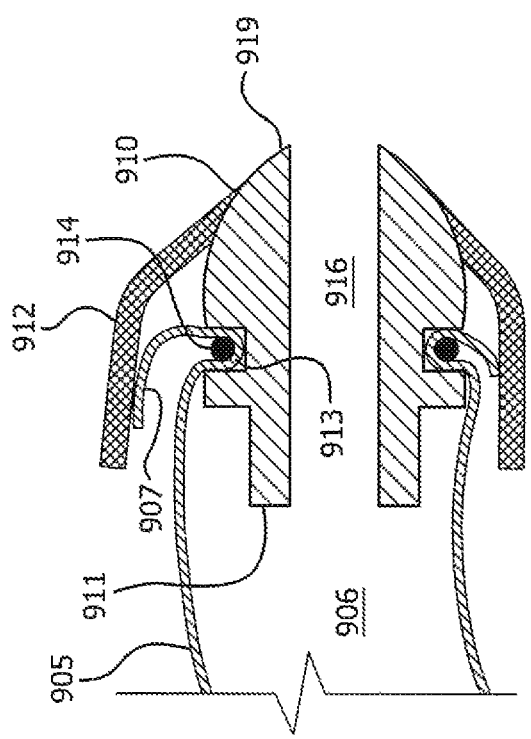
FIG. 9A is a cross-sectional illustration of a distal end of a sleeve, depicting one embodiment of a component designed to configure said distal end to be atraumatic to body tissues.

FIG. 9B is a cross-sectional illustration of a distal end of a sleeve 905, depicting another embodiment of a component 920 designed to configure said distal end to be atraumatic to body tissues. The component 920 has a cylindrical shape with a proximal end 921, a distal end 929, and a lumen 926 within. The component 920 is open at both ends 921, 929. The lumen 926 of the component 920 is in fluid communication with a lumen 906 of the sleeve 905 to allow for food to pass through the wire mesh of the device, the sleeve 905, and the component 920. The distal end 929 is rounded into a blunt shape that is atraumatic to body tissues. An outer surface of the component 920 includes a groove 923 configured to receive a circular member or O-ring 924. To attach the component 920 to the sleeve 905, the distal end of the sleeve 905 is coaxially slid onto the proximal end 921 of the component 920 such that a portion of the sleeve 905 is positioned over said groove 923. The O-ring 924 is placed over the sleeve 905 and into the groove 923. The distal sleeve end is then folded in a proximal direction back toward the sleeve 905 body. A heat shrink tube 925 is then placed over said distal sleeve end and said O-ring 924. Heat is applied to the heat shrink tube 925 to shrink the tube 925 such that it securely connects the sleeve 905 to the component 920. Any sharp ends in the distal sleeve end are contained under the heat shrink tube 925 and are not exposed to body tissues.

Figure 9C:
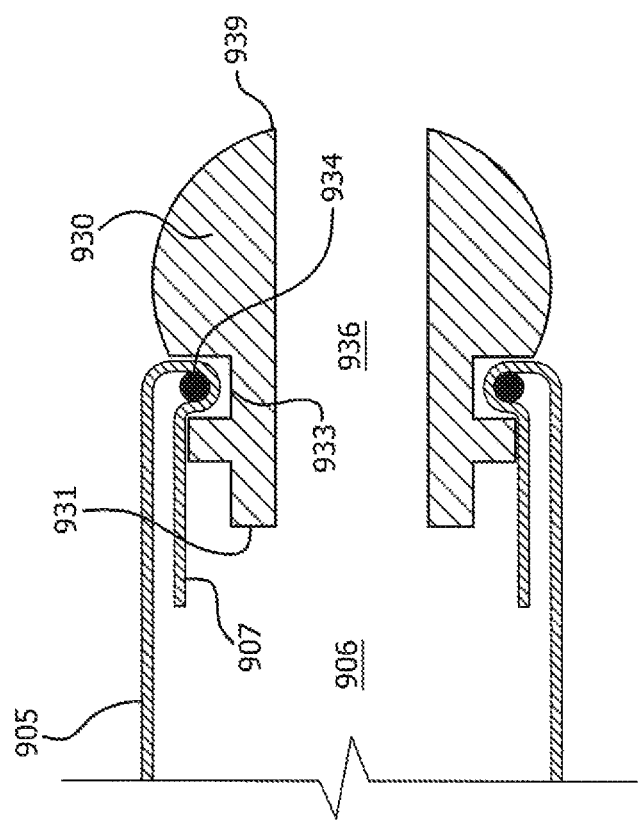
FIG. 9C is a cross-sectional illustration of a distal end of a sleeve, depicting another embodiment of a component designed to configure said distal end to be atraumatic to body tissues.

FIG. 9C is a cross-sectional illustration of a distal end of a sleeve 905, depicting another embodiment of a component 930 designed to configure said distal end to be atraumatic to body tissues. The component 930 has a cylindrical shape with a proximal end 931, a distal end 939, and a lumen 936 within. The component 930 is open at both ends 931, 939. The lumen 936 of the component 930 is in fluid communication with a lumen 906 of the sleeve 905 to allow for food to pass through the wire mesh of the device, the sleeve 905, and the component 930. The distal end 939 is rounded into a blunt shape that is atraumatic to body tissues. An outer surface of the component 930 includes a groove 933 configured to receive a circular member or O-ring 934. To attach the component 930 to the sleeve 905, the sleeve 905 is first everted to be inside out. The distal end of the sleeve 905 is then coaxially slid onto the distal end 939 of the component 930 such that a portion of the sleeve 905 is positioned over said groove 933. The O-ring 934 is placed over the sleeve 905 and into the groove 933. The sleeve 905 is then folded in a proximal direction back over the O-ring 934 and proximal end 931 of the component 930, providing a robust connection of the sleeve 905 to the component 930. This process of connecting the sleeve 905 to the component 930 ensures that the distal sleeve end 907 will become positioned within the sleeve lumen 906. Any sharp ends in the distal sleeve end 907 are contained within the sleeve lumen 906 and are not exposed to body tissues.

Figure 10:
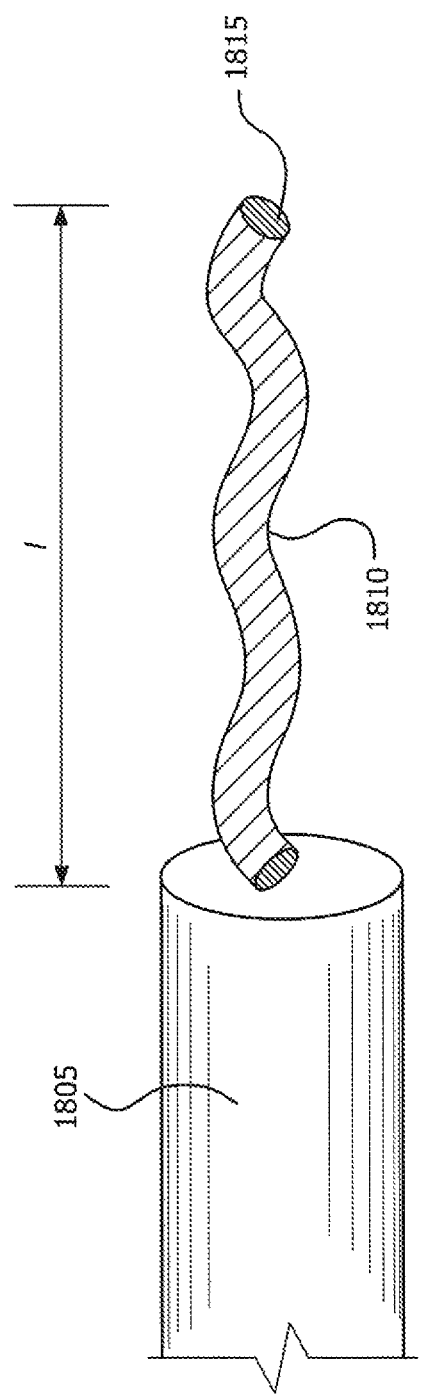
FIG. 10 is an illustration of a distal end of a sleeve with a positioning tail attached thereto, in accordance with one embodiment of the present specification.

FIG. 10 is an illustration of a distal end of a sleeve 1005 with a positioning tail 1010 attached thereto, in accordance with one embodiment of the present specification. The positioning tail 1010 is attached to the distal end of a short sleeve 1005 having a length of 5 mm to 500 mm. The positioning tail 1010 comprises a ribbon of material extending from the distal end of the sleeve 1005 into a patient's duodenum and is used to help maintain proper implant orientation of the sleeve 1005 relative to a patient's pylorus. In various embodiments, the positioning tail 1010 has a length/in a range of 5 mm to 500 mm. In one embodiment, the positioning tail 1010 has a length/of 25 mm. In one embodiment, the distal end of the positioning tail 1010 includes a bead 1015 for weighing down said distal end. In another embodiment, the distal end of the positioning tail includes a plurality of separate free ends similar to a horse tail. In other embodiments, the distal end of the positioning tail includes any mechanism or component designed to provide additional weight or tugging upon said distal end to allow for pulling on said tail to ensure proper sleeve orientation. In one embodiment, the distal end of the positioning tail does not include any additional components.

Figure 11A:
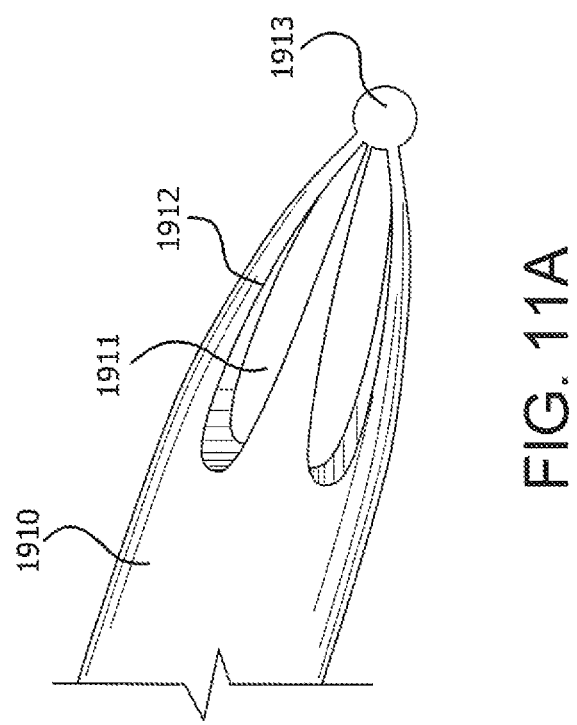
FIG. 11A is an illustration of a distal end of a sleeve comprising a plurality of fringes joined to a ball, in accordance with one embodiment of the present specification.

FIG. 11A is an illustration of a distal end of a sleeve 1110 comprising a plurality of fringes 1112 joined to a ball 1113, in accordance with one embodiment of the present specification. In various embodiments, the distal end of the sleeve 1110 comprises two or more fringes 1112. In one embodiment, the distal end of the sleeve 1110 comprises four fringes 1112. Each fringe 1112 comprises a portion of sleeve material which is separate from adjacent fringes 1112. The fringes 1112 are separated from one another by a space 1111 which allows food passing through the intragastric device to exit from the sleeve 1110. In various embodiments, each fringe 1112 has a length in a range of 5 mm to 500 mm and a width in a range of 1 mm to 15 mm. In some embodiments, the width of each fringe 1112 decreases as the fringe 1112 extends distally. The fringes 1112 are connected to a ball 1113 at the most distal end of the sleeve 1110. In various embodiments, the ball 1113 has a diameter in a range of 2 mm to 30 mm. In various embodiments, the ball 1113 is glued or bonded to each fringe 1107. The ball 1113 serves to join the fringes 1112 together and to weigh down the distal end of the sleeve 1110 to assist with proper device orientation. Since the ball 1113 has a spherical shape, it has no sharp edges and is atraumatic to body tissues. In another embodiment, the most distal ends of the fringes 1112 are tied together into a knot to form the ball 1113 and no additional ball component is required. In some embodiments, the fringes 1112 and ball 1113 are parachute shaped. In one embodiment, the circumference of the ball is designed to sit inside an outer catheter of a delivery device.

Figure 11B:
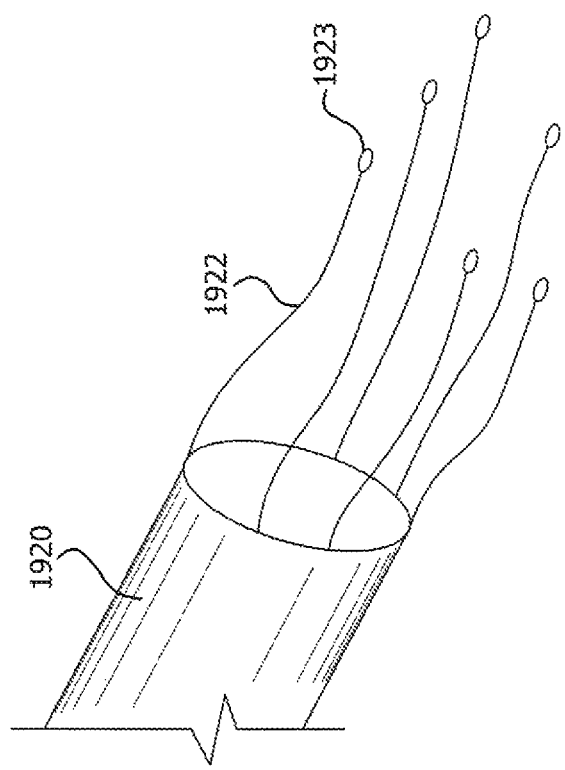
FIG. 11B is an illustration of a distal end of a sleeve having at least one suture with attached suture loop or bead extending therefrom, in accordance with one embodiment of the present specification.

FIG. 11B is an illustration of a distal end of a sleeve 1120 having at least one suture 1122 with attached suture loop or bead 1123 extending therefrom, in accordance with one embodiment of the present specification. In one embodiment, the sleeve 1120 includes six sutures 1122. In various embodiments, the sutures 1122 have a length in a range of 5 mm to 500 mm. In one embodiment, the sutures 1122 are composed of UHMWPE. A proximal end of each suture 1122 is attached to the distal end of the sleeve 1120 and a distal end of each suture 1122 includes an attached suture loop or bead 1123. The suture loops or beads 1123 are designed to add weight to the distal end of the sleeve 1120 to pull the sleeve 1120 into the proper implant orientation. Since the suture loops or beads 1123 each have a spherical shape, they have no sharp edges and are atraumatic to body tissues.

Figure 12A:
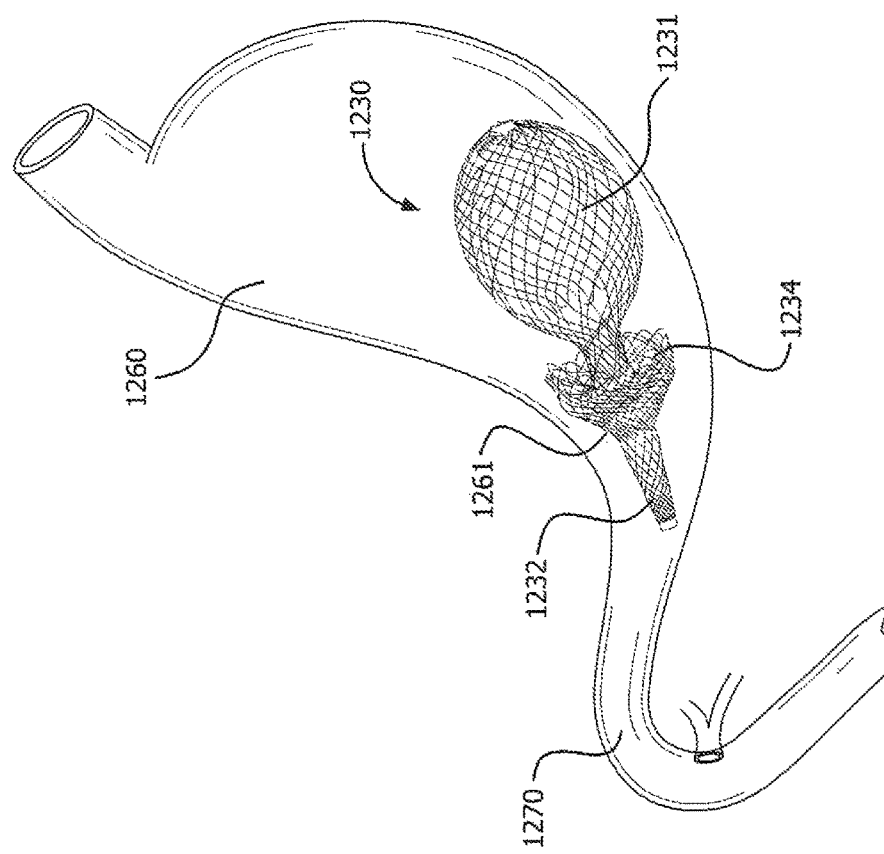
FIG. 12A is an illustration of an intragastric device having an oval shaped wire mesh structure deployed in the gastrointestinal tract of a patient, in accordance with one embodiment of the present specification.

FIG. 12A is an illustration of an intragastric device 1230 having an oval shaped wire mesh structure 1231 deployed in the gastrointestinal tract of a patient, in accordance with one embodiment of the present specification. In the pictured embodiment, the device 1230 includes a wire mesh structure 1231 having an anti-migration collar 1234 and attached sleeve 1232. The device 1230 is deployed such that the wire mesh structure 1231 resides in the stomach 1260 with the anti-migration collar 1234 positioned just proximal to the pylorus 1261 and the sleeve 1232 extending through the pylorus 1261 and into the duodenum 1270. The distal end of the sleeve 1232 resides in the duodenum 1270. The anti-migration collar prevents migration of the totality of the device 1230 through the pylorus 1261 and into the duodenum 1270. The device 1230 occupies a volume of the stomach 1260, does not move entirely past the pylorus 1261, and provides a bypass for food past the pylorus 1261 and a portion of the duodenum 1270. In various embodiments, the sleeve 1232 is a short sleeve having a length in a range of 5 cm-120 cm. In one embodiment, the sleeve 1232 is a short sleeve having a total length of 60 cm. In some embodiments, the short sleeve 1232 functions to weigh down wire mesh structure 1231 and orient the wire mesh structure 1231 in the correct direction toward the pylorus 1261. In addition, in one embodiment, the device 1230 having a short sleeve 1232 is capable of moving freely within the patient's stomach 1260 after deployment. The short sleeve 1232 is capable of passing back and forth through the pylorus 1261 atraumatically. During situations when the device 1230 has moved such that the short sleeve 1232 is not positioned within the pylorus 1261 and duodenum 1270 but is rather in the stomach 1260 with the remainder of the device 1230, the short sleeve also functions to impede and regulate the flow of food into the pylorus 1261. This occurs as food enters the device 1230 at the proximal end of the wire mesh structure 1231 and travels through the wire mesh structure 1231 and sleeve 1232, where its progress is slowed as it passes through the funnel shaped sleeve 1232. At no time during its proper function is the device fixedly or permanently anchored to the wall of the gastrointestinal tract. After deployment, for a majority of its functional time, at least a portion of the device or the entire device is free to move relative to the stomach or small intestine. As a result of its included lumen, at no time during its normal function does the device completely or permanently block the passage of gastric contents into the small intestine for any clinically meaningful duration of time. Based on the shape of the sleeve, in various embodiments, the device can increase, decrease, or have no effect on, gastric emptying.

Figure 12B:
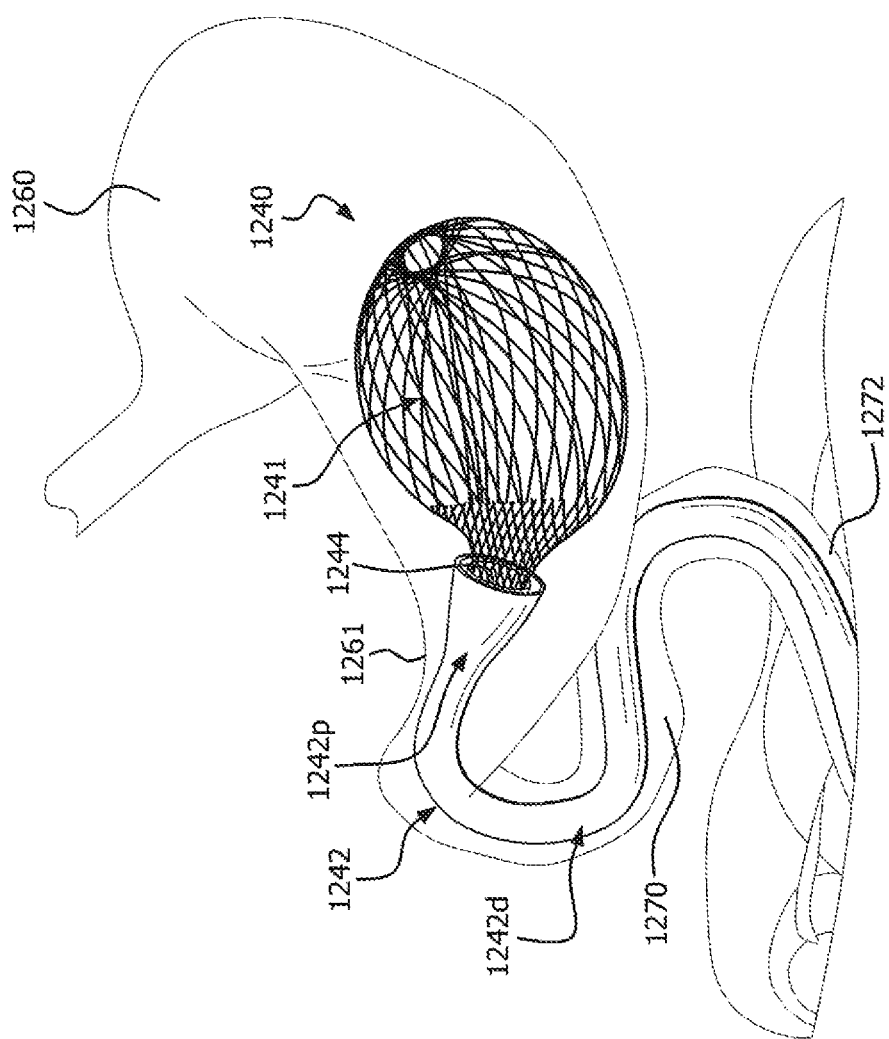
FIG. 12B is an illustration of an intragastric device having an oval shaped wire mesh structure deployed in the gastrointestinal tract of a patient, in accordance with another embodiment of the present specification.

FIG. 12B is an illustration of an intragastric device 1240 having an oval shaped wire mesh structure 1241 deployed in the gastrointestinal tract of a patient, in accordance with another embodiment of the present specification. The wire mesh structure 1241 is positioned in the patient's stomach 1260 and includes an anti-migration collar 1244 to which is attached a sleeve 1242. The sleeve 1242 includes a proximal, funnel shaped portion 1242p which resides in the stomach, just proximal to the pylorus 1261. The sleeve 1242 also includes a distal, cylindrically shaped portion 1242d which passes through the pylorus 1261 and the duodenum 1270 and ends in the jejunum 1272, where it releases the gastric contents passing through the intragastric device 1240, effectively bypassing the pylorus 1261 and duodenum 1270. In another embodiment, the sleeve has a shorter length and ends in the duodenum such that gastric contents passing through the intragastric device bypass only the pylorus and a proximal portion of the duodenum. At no time during its proper function is the device fixedly or permanently anchored to the wall of the gastrointestinal tract. After deployment, for a majority of its functional time, at least a portion of the device or the entire device is free to move relative to the stomach or small intestine. As a result of its included lumen, at no time during its normal function does the device completely or permanently block the passage of gastric contents into the small intestine for any clinically meaningful duration of time. Based on the shape of the sleeve, in various embodiments, the device can increase, decrease, or have no effect on, gastric emptying.

Figure 13A:
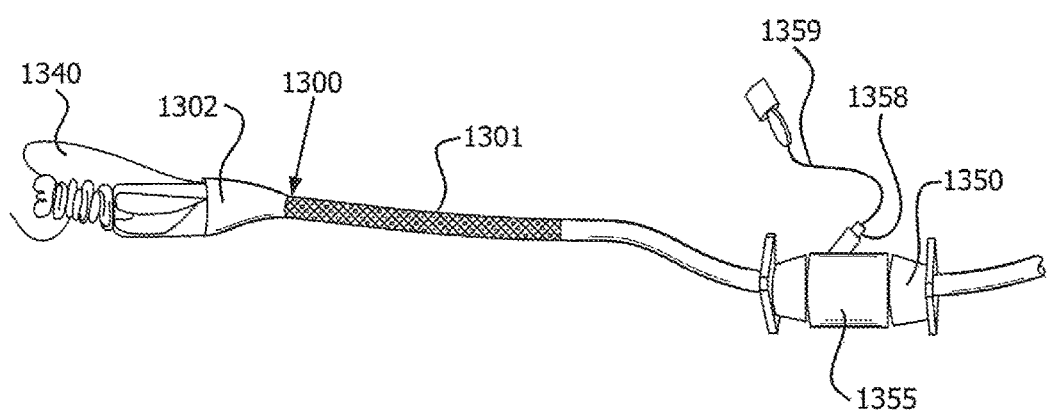
FIG. 13A is an illustration of a first exemplary delivery device for an intragastric device, in accordance with one embodiment of the present specification.

FIG. 13A is an illustration of a first exemplary delivery device 1350 for an intragastric device 1300, in accordance with one embodiment of the present specification. An intragastric device 1300, comprising a compressed wire mesh structure 1301 and sleeve 1302, is positioned coaxially about the distal end of the delivery device or catheter 1350. A suture or thread 1340 is wrapped about the intragastric device 1300, maintaining the intragastric device 1300 in its compressed configuration. The catheter 1350 further includes a thread port 1358 from which the suture or thread 1340 used to compress the intragastric device 1300 exits the proximal end of the catheter 1350. A physician pulls on the free end 1359 of the suture or thread 1340 to release the intragastric device 1300. In one embodiment, the catheter 1350 also includes a locking mechanism 1355 for locking the device 1350 in position.

Figure 13B:
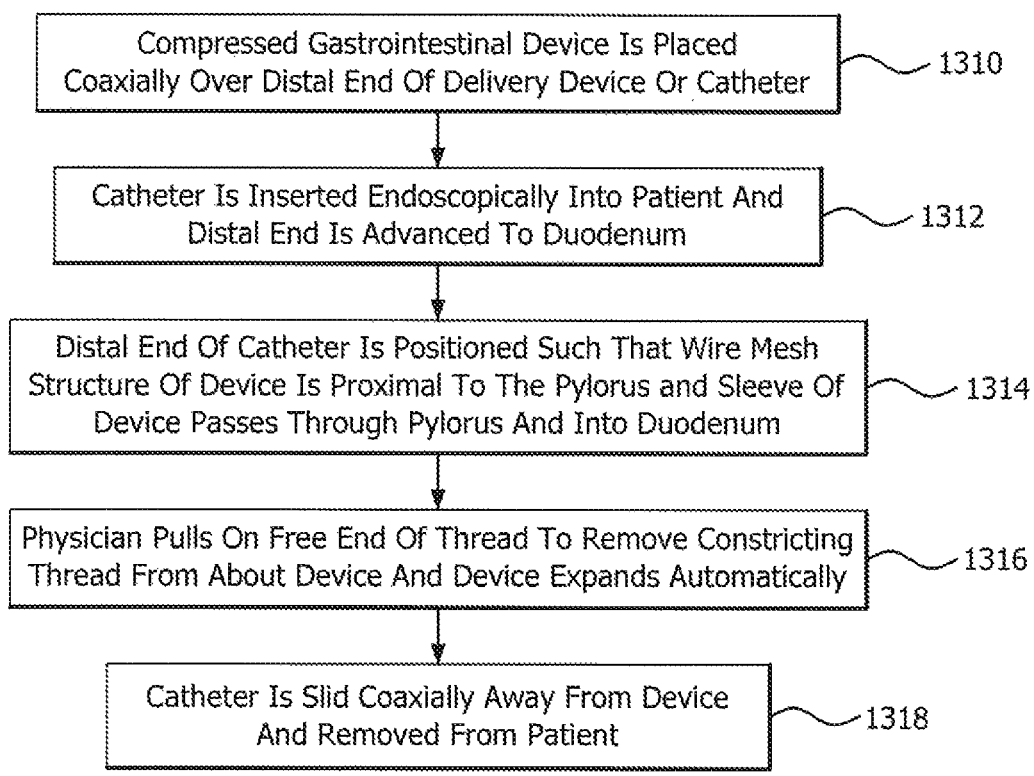
FIG. 13B is a flow chart illustrating the steps involved in delivering an intragastric device using the delivery device of FIG. 13A, in accordance with one embodiment of the present specification.

FIG. 13B is a flow chart illustrating the steps involved in delivering an intragastric device using the delivery device of FIG. 13A, in accordance with one embodiment of the present specification. At step 1310, a compressed intragastric device is placed coaxially over the distal end of the delivery device or catheter. The catheter is then inserted endoscopically into the patient and its distal end is advanced to the duodenum at step 1312. Then, at step 1314, the distal end of the catheter is positioned such that the wire mesh structure of the intragastric device is in the stomach just proximal to the pylorus and the sleeve of the device passes through the pylorus and into the duodenum. At step 1316, the physician pulls on the free end of the thread to remove the constricting thread from about the intragastric device, allowing the intragastric device to expand automatically. Finally, at step 1318, the catheter is slid coaxially away from the intragastric device and removed from the patient.

In various embodiments, the delivery device includes atraumatic distal ends.

Figure 14A:
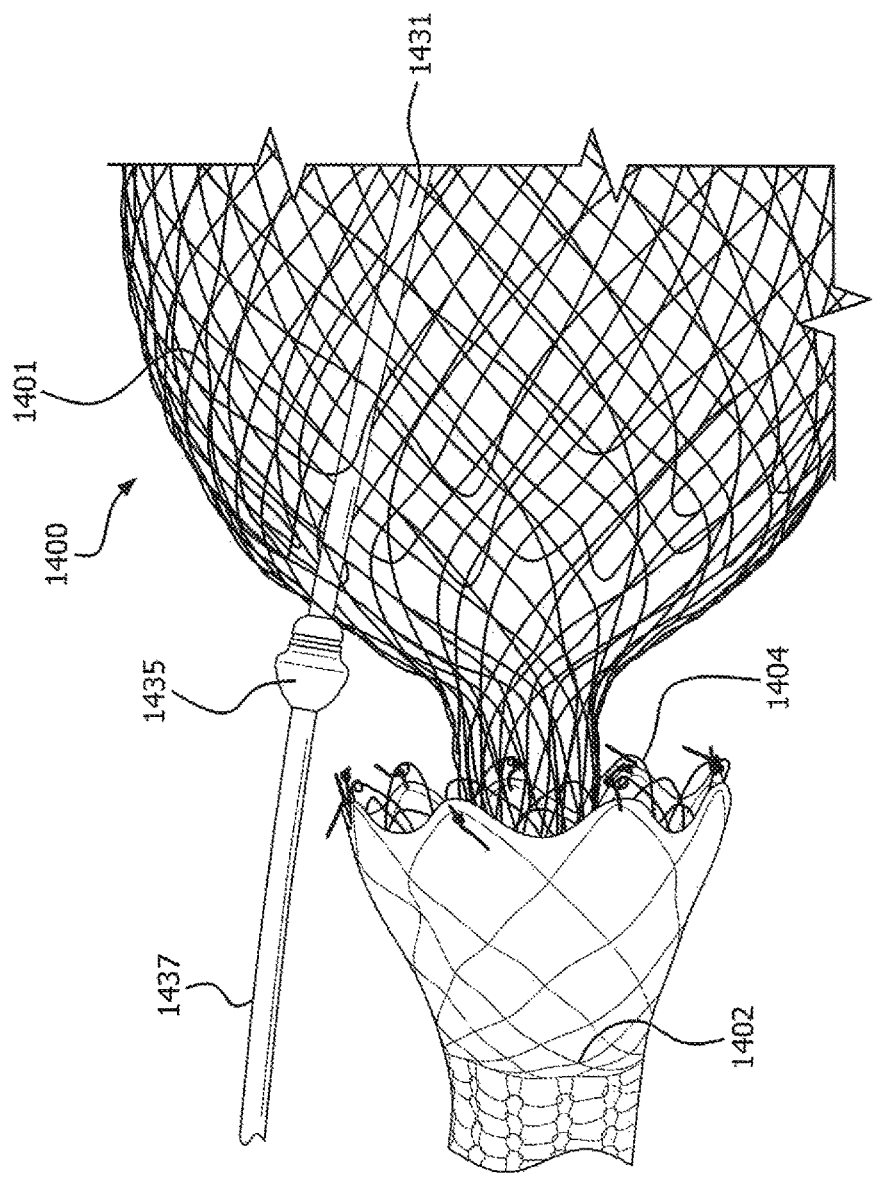
FIG. 14A is an illustration of a wire mesh structure of an intragastric device being loaded onto a delivery device, in accordance with one embodiment of the present specification.

FIG. 14A is an illustration of a wire mesh structure 1401 of an intragastric device 1400 being loaded onto a delivery device, in accordance with one embodiment of the present specification. Referring to FIG. 14A, a portion of the inner catheter 1431 and pilot component 1437 of the delivery device are depicted. The delivery device includes a proximal spherical component 1435 at the transition from inner catheter 1401 to pilot component 1437. The wire mesh structure 1401 includes a sleeve 1402 attached to its anti-migration collar 1404. When loading the intragastric device 1400 onto the delivery device, the pilot component 1437 is passed through an off-center opening between the wires of the wire mesh structure 1401 such that the proximal spherical component 1435 is positioned just distal to the wire mesh structure 1401 and the inner catheter 1431 lies within the internal volume of the wire mesh structure 1401.

Figure 14B:
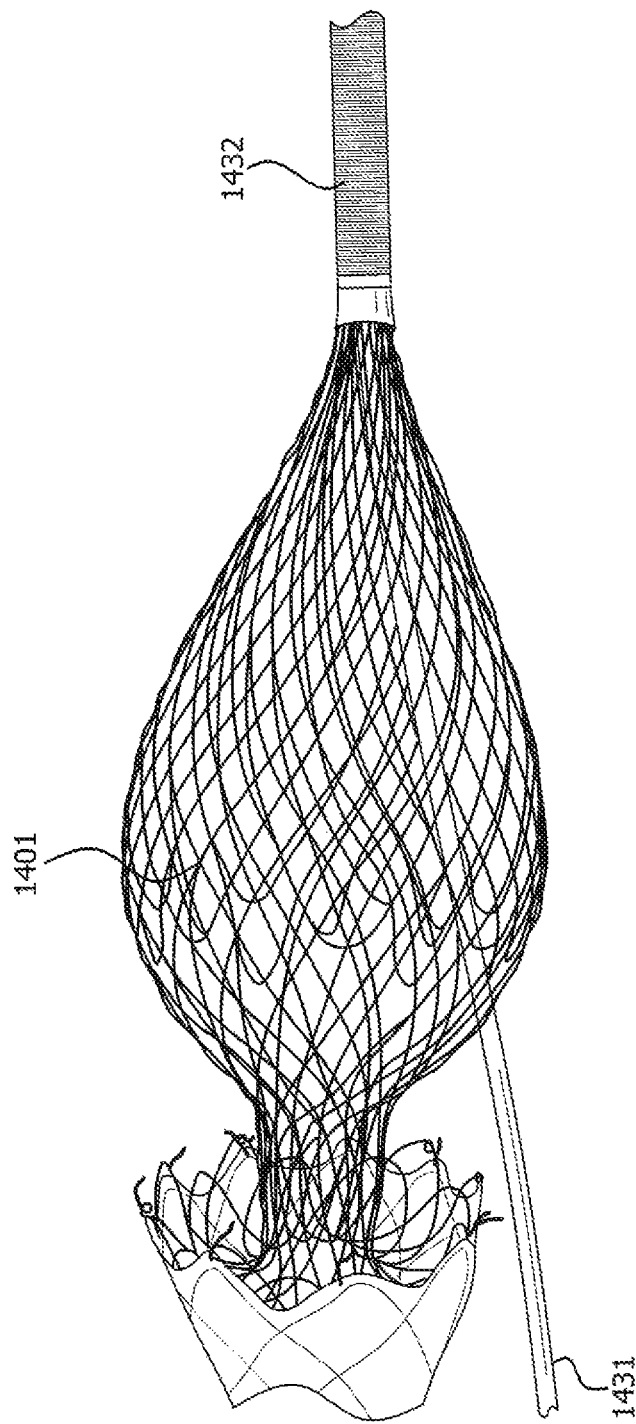
FIG. 14B is an illustration of the wire mesh structure of FIG. 14A further loaded onto the delivery device.

FIG. 14B is an illustration of the wire mesh structure 1401 of FIG. 14A further loaded onto the delivery device. The proximal end of the wire mesh structure 1401 has been compressed and is now contained within the distal end of the outer catheter 1432 of the delivery device. The proximal spherical component is no longer visible as the wire mesh structure 1401 has been advanced proximally along the inner catheter 1431. Referring to FIG. 14B, the inner catheter is depicted exiting the wire mesh structure 1401 through an opening offset from center of the wire mesh structure 1401. The sleeve is then wrapped coaxially about the inner catheter as described with reference to FIG. 14C. In another embodiment, the inner catheter (and attached pilot component) continues within the wire mesh structure and exits through an opening in a side of the proximal, funnel shaped portion of the sleeve. In another embodiment, the inner catheter continues within the wire mesh structure and exits through an opening in a side of the distal, cylindrically shaped portion of the sleeve. In yet another embodiment, the inner catheter continues within the wire mesh structure, passes through the entire sleeve, and exits through the opening in the distal end of the sleeve.

Figure 14C:
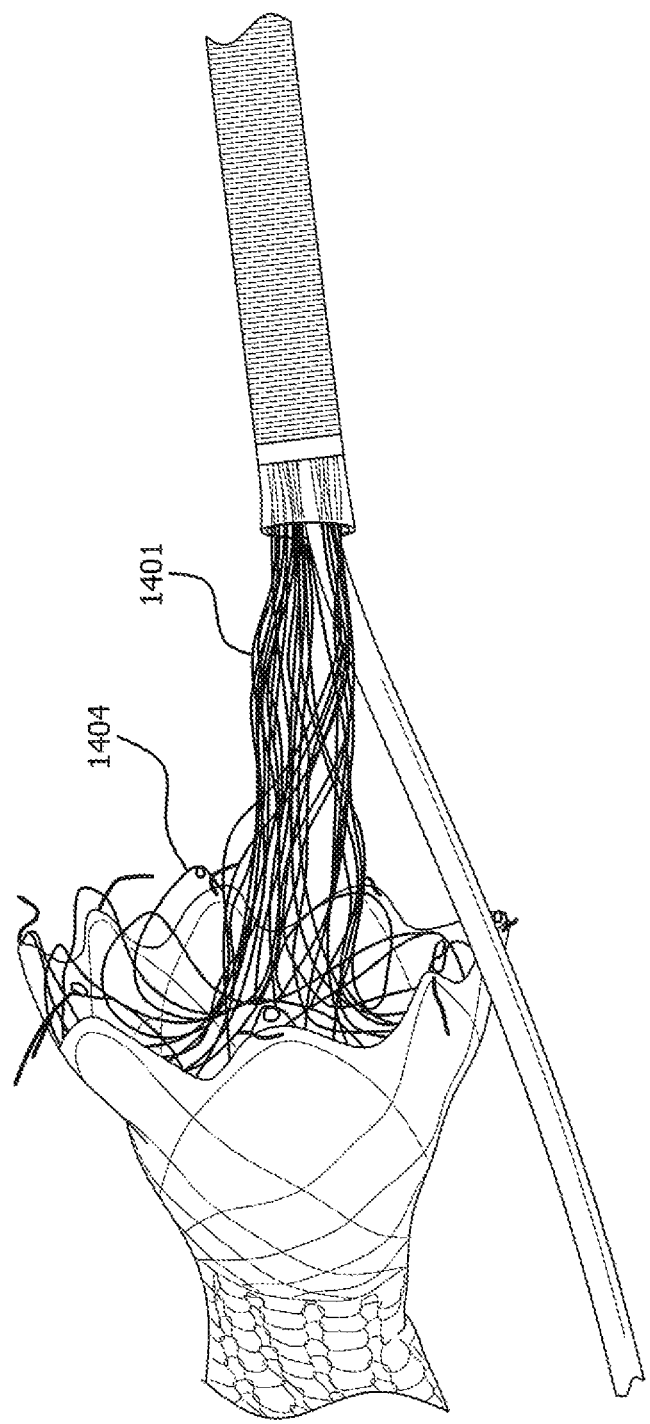
FIG. 14C is an illustration of the wire mesh structure of FIG. 14A loaded onto the delivery device such that only the anti-migration collar remains to be loaded.
Figure 14D:
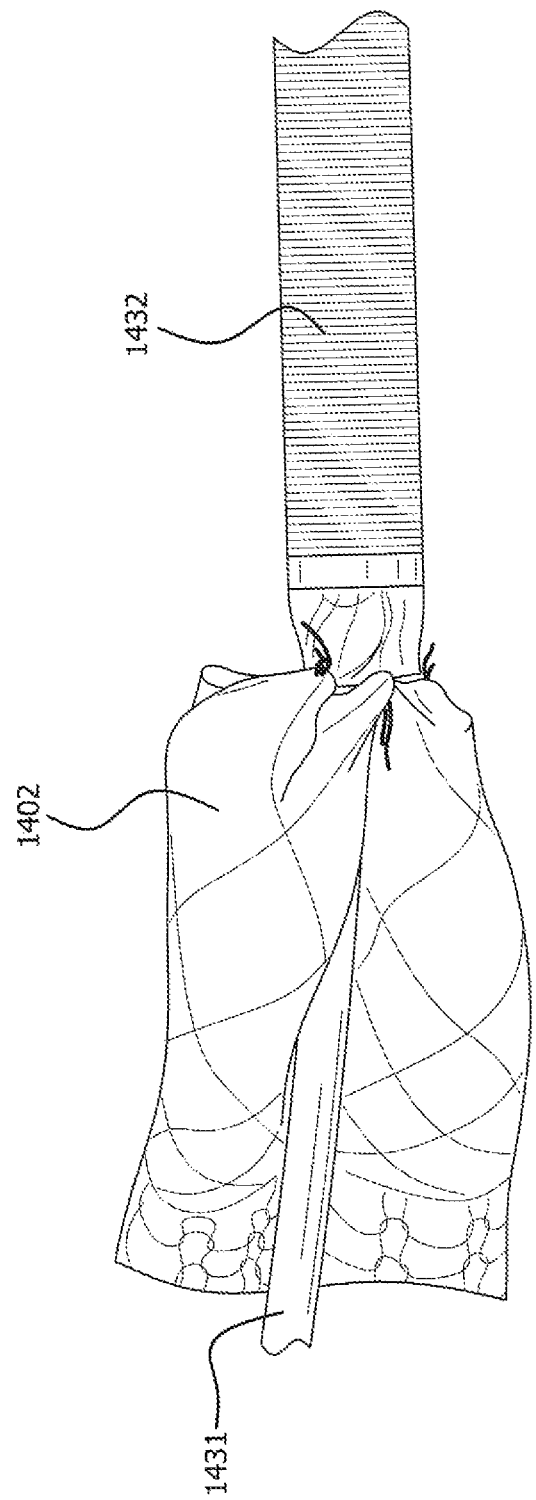
FIG. 14D is an illustration of the wire mesh structure of FIG. 14A fully loaded onto the delivery device.

FIG. 14C is an illustration of the wire mesh structure 1401 of FIG. 14A loaded onto the delivery device such that only the anti-migration collar 1404 remains to be loaded. FIG. 14D is an illustration of the wire mesh structure of FIG. 14A fully loaded onto the delivery device. Referring to FIG. 14D, the wire mesh structure is no longer visible as it is fully contained within the distal end of the outer catheter 1432. The sleeve 1402 is depicted wrapped coaxially about the inner catheter 1431.

Figure 14E:
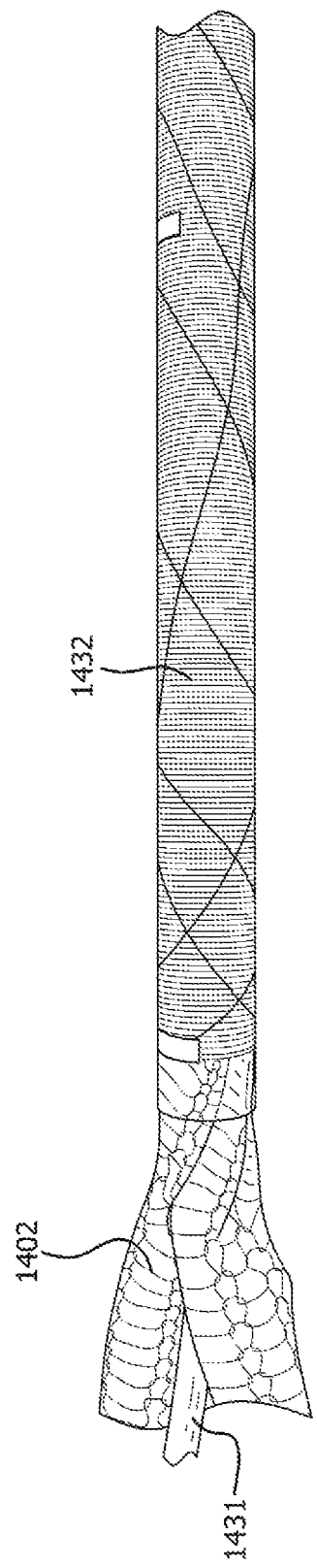
FIG. 14E is an illustration of a sleeve of the intragastric device of FIG. 14A partially loaded onto the delivery device.
Figure 14F:
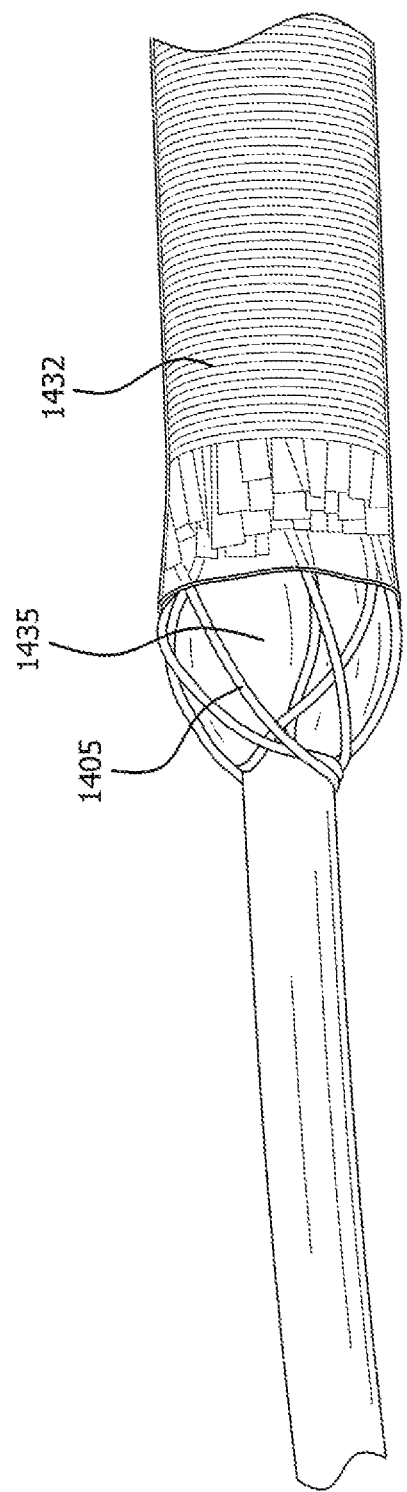
FIG. 14F is an illustration of the intragastric device of FIG. 14A fully loaded onto the delivery device.

FIG. 14E is an illustration of a sleeve 1402 of the intragastric device of FIG. 14A partially loaded onto the delivery device. A portion of the sleeve 1402, wrapped coaxially about the inner catheter 1431, is visible extending from the distal end of the outer catheter 1432. FIG. 14F is an illustration of the intragastric device of FIG. 14A fully loaded onto the delivery device. The proximal spherical component 1435 is positioned at the distal end of the outer catheter 1432. In one embodiment, a plurality of sutures 1405 extending from the distal end of the sleeve are tied about the proximal spherical component 1435 to maintain the intragastric device in place until ready for delivery. Prior to delivery, the sutures 1405 are undone so the intragastric device may be deployed.

Figure 15A:
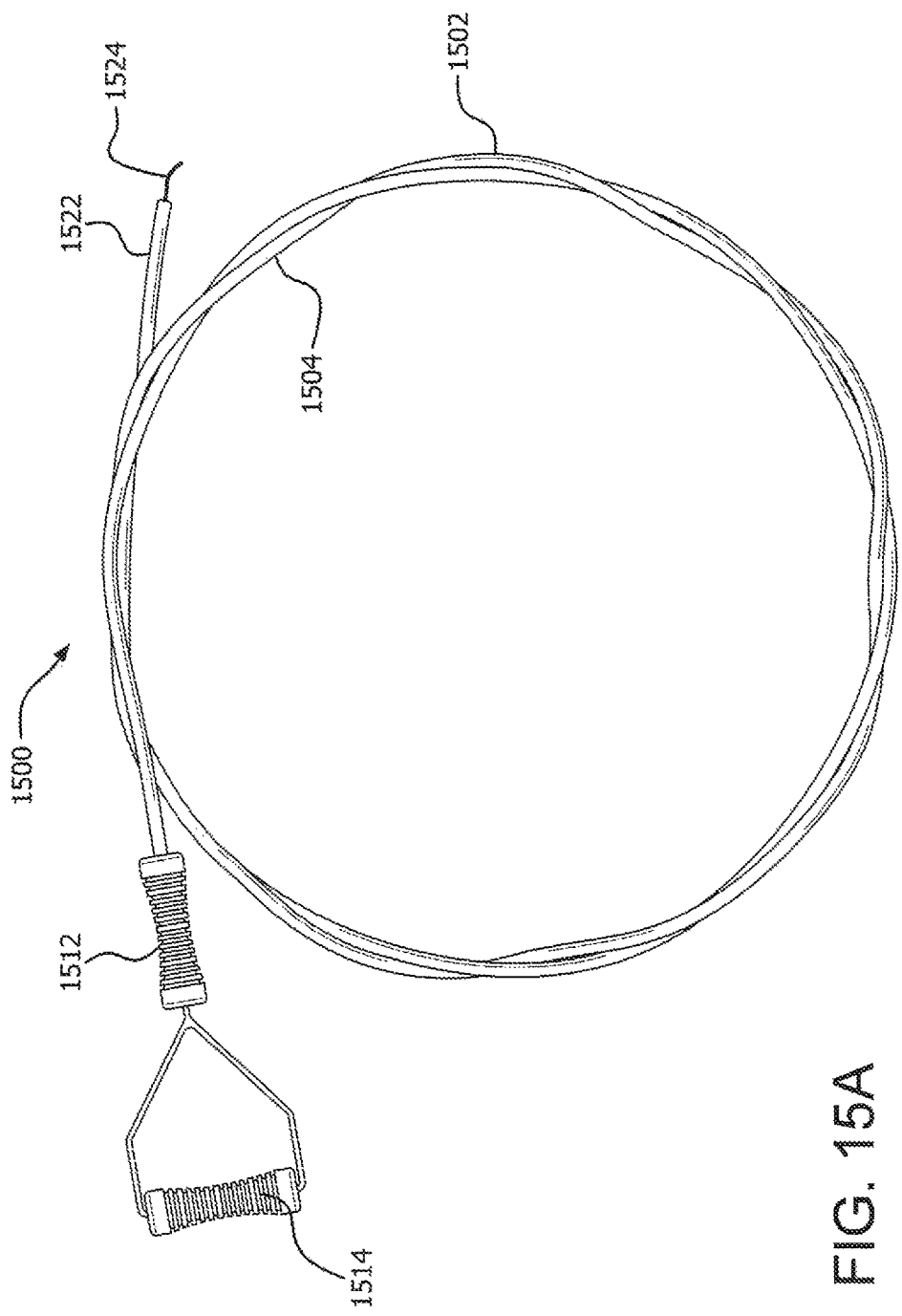
FIG. 15A is an illustration of a retrieval device for removing an intragastric device, in accordance with one embodiment of the present specification.

FIG. 15A is an illustration of a retrieval device 1500 for removing an intragastric device in accordance with another embodiment of the present specification. The retrieval device 1500 includes a flexible outer tube 1502 comprising an elongate body having a proximal end, a distal end, and a lumen within. A first handle 1512 is attached to the proximal end and an opening 1522 is positioned at the distal end of the outer tube 1502. A flexible inner member 1504 comprising an elongate body with a proximal end and a distal end is disposed within the lumen of the outer tube 1502. In one embodiment, the inner member 1504 comprises a flexible metal wire. A second handle 1514 is attached to the proximal end and a retrieval mechanism 1524 is formed from the distal end of the inner member 1504. In one embodiment, the retrieval mechanism 1524 comprises a hook. In one embodiment, the hook is lockable.

Figure 15B:
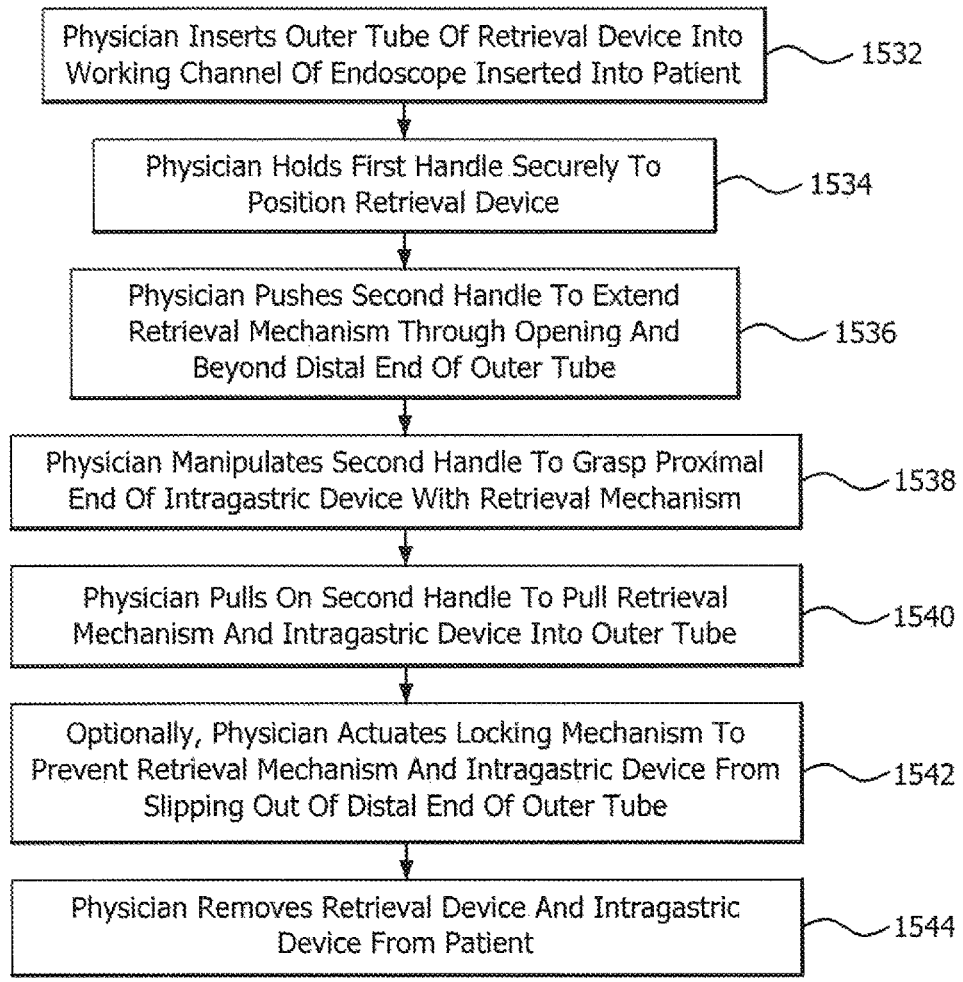
FIG. 15B is a flow chart illustrating the steps involved in removing an intragastric device from a patient using the retrieval device of FIG. 15A, in accordance with one embodiment of the present specification.

FIG. 15B is a flow chart illustrating the steps involved in removing an intragastric device from a patient using the retrieval device of FIG. 15A, in accordance with one embodiment of the present specification. At step 1532, a physician inserts the outer tube of the retrieval device into a working channel of an endoscope inserted into a patient. At this point, the retrieval mechanism at the distal end of the inner member is contained within the distal end of the outer tube. At step 1534, the physician holds the first handle securely to position the retrieval device within the gastrointestinal tract of the patient. Then, at step 1536, the physician pushes on the second handle to extend the retrieval mechanism through the opening and beyond the distal end of the outer tube. The physician manipulates the second handle to grasp a proximal end of the intragastric device with the retrieval mechanism at step 1538. In one embodiment, the proximal end of the intragastric device includes a set of staggered nodes, as depicted as nodes 1615 with reference to FIG. 16B, to ease grasping with the retrieval mechanism. Once the intragastric device has been secured by the retrieval mechanism, the physician pulls on the second handle to pull the retrieval mechanism and at least a portion of the attached intragastric device into the distal end of the outer tube at step 1540. The intragastric device is composed of a shape memory metal so that it is easily compressible to a size capable of fitting into said outer tube. Optionally, at step 1542, the physician actuates a locking mechanism on the retrieval device to prevent the retrieval mechanism and attached intragastric device from slipping out of the distal end of the outer tube. Finally, at step 1544, the physician removes the retrieval device and attached intragastric device from the patient.

In one embodiment, the wire mesh structure of the intragastric device is covered in an expandable balloon. The balloon forms an enveloping layer on the mesh structure and protects the structure from stomach acids. In one embodiment, the balloon is made up of silicone and can be compressed to the size of a capsule for delivery. As the wire mesh expands after the delivery, if conforms to the shape of the balloon.

Figure 16B:
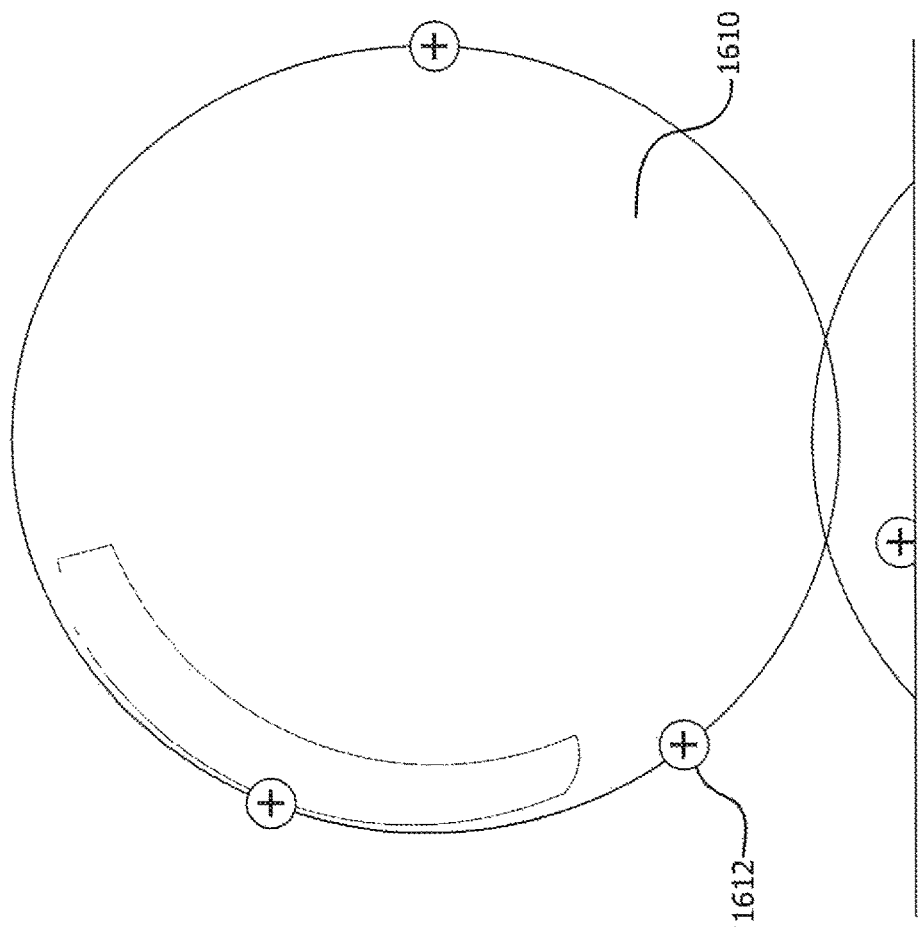
FIG. 16B shows a post deployment configuration of the device, according to one embodiment of the present specification.
Figure 16A:
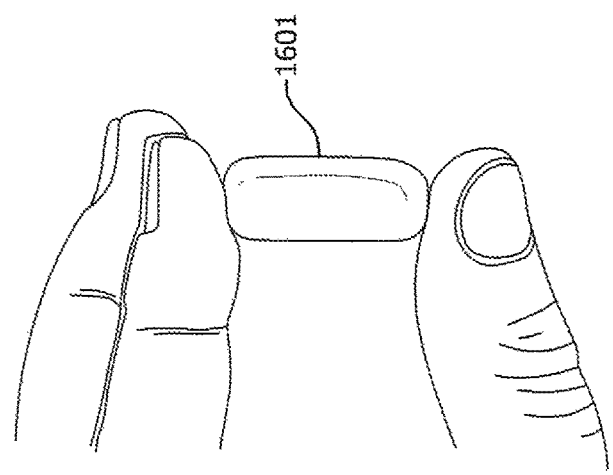
FIG. 16A shows a balloon covered wire mesh device before deployment, compressed to the size of a capsule, according to one embodiment.

FIG. 16A shows a balloon covered wire mesh device before deployment, compressed to the size of a capsule. In various embodiments, the size of capsule 1601 is in the range of 8 mm×13 mm. In some embodiments, the balloon covered wire mesh, in the compressed configuration, is swallowed by the user for delivering the device to the user's gastrointestinal tract. Once exposed to gastric contents, the balloon expands with the wire mesh expanding within the balloon. In other embodiments, the balloon covered wire mesh, in the compressed configuration, is delivered via a delivery device or catheter, to the patient's gastrointestinal tract. Once released from the delivery device, the balloon covered wire mesh expands, via the shape memory properties of the wire mesh, to its post-deployment configuration.

FIG. 16B shows a post deployment configuration of the device, where the balloon 1610 around the wire mesh device expands. In one embodiment, the device includes one or more sutures 1612 to hold the balloon to the wire mesh. As described earlier, the wire mesh itself expands upon deployment. Therefore, in one embodiment, the balloon envelops the mesh in a glove-like configuration and protects the mesh device from exposure to acid. Compared to a silicone coating over the wires of the mesh, the present configuration substantially slows down the exposure of the wire mesh to acid, thereby preventing rapid corrosion of the Nitinol material of the mesh and prolonging the life of the device. In some embodiments, the balloon covering provides the device with a functional lifespan of at least one to two years wherein corrosion of the wires of the mesh by gastric acid does not occur until after at least one year.

In some embodiments, the balloon envelope, and wire mesh, expand to have a volume in a range of 400-450 ml after deployment. In some embodiments, the balloon is inflated with air, saline, water or any other suitable medium to assist with expansion of the balloon and allow for expansion of the wire mesh.

In some embodiments, an intragastric device of the present specification is an anchorless device comprising a compressible free-floating structure instead of the wire mesh structure described in other embodiments. The free-floating structure is attached to a sleeve in a manner similar to the previous embodiments, and the sleeve passes through the pylorus and into the duodenum. In various embodiments, the free-floating component in the stomach keeps the sleeve in place, rendering the sleeve effectively anchorless. That is, the sleeve is not physically attached to any part of the GI tract. In one embodiment, the intragastric device comprising the free-floating component and sleeve is atraumatic and does not damage the GI tissue.

As known in the art, the sleeve is generally anchored or stented below the pylorus. In the present specification, however, a free floating component is attached to the sleeve at its proximal end and designed to keep the sleeve in place by remaining in the area above the pylorus. Therefore, the component stays in the stomach, proximal to the pylorus, and the sleeve extends through the pylorus and into the mid-duodenum. Gastric contents enter the sleeve proximal to the pylorus, travel through the sleeve, and exit the sleeve in the mid-duodenum, bypassing the pylorus, ampulla of Vater, and proximal duodenum. It may be noted that the present embodiment does not use the functionality of the wire mesh structure, which includes food sequestration and delayed gastric emptying.

As described earlier with reference to FIGS. 8A through 8F, embodiments of the wire mesh intragastric device comprise an anchorless ball or umbrella structure with or without a collar. It may be noted that the ball or umbrella mesh structure has a different structure than the sleeve of the device, thereby allowing a different level of compression. This prevents the ball or umbrella structure from being passed through the pylorus. The ball or umbrella thus prevents movement of the sleeve too far back into the stomach. The compressible free-floating structures described below also have a different structure than the sleeve allowing a different level of compression. In various embodiments, the wire mesh structure (having the food sequestering functionality) or the compressible free-floating structures (not having the food sequestering functionality) occupy a volume of the stomach such that the sleeve can only move approximately 5 cm up into the stomach.

FIGS. 17 through 34 illustrate various embodiments of an anchorless device comprising a compressible free-floating structure (e.g., anchoring structure) in the stomach with an attached sleeve which passes through the pylorus and into the duodenum. The free floating structures in various configurations float in the stomach and are anchoring structure to keep the sleeve in place in the intestines. In various embodiments, sleeves are attached by means of sutures or strings distal to the structure. In one embodiment, for all configurations of the free floating structure, the structure together with the sleeve can be delivered by a catheter, and after deployment the structure is in the stomach and sleeve is in the duodenum. In one embodiment, the free floating structures in various configurations are made of Nitinol. In various embodiments, the free floating structures are space occupying and non-porous, and do not perform the function of food sequestering. In various embodiments, no food passes through the free floating structure component, but passes through the attached sleeve via a first opening at the proximal end of the sleeve and a second opening at the distal end of the sleeve, which opens into the mid-duodenum. In some embodiments, food can enter at a proximal end of the free floating structure and pass through the structure and into the sleeve. This however, has no effect on food sequestering or gastric emptying. In various embodiments, the free floating structure is composed of a shape memory material such as Nitinol, so that it can be compressed partially by gastric contractions but is able return to its original shape.

Figure 17:
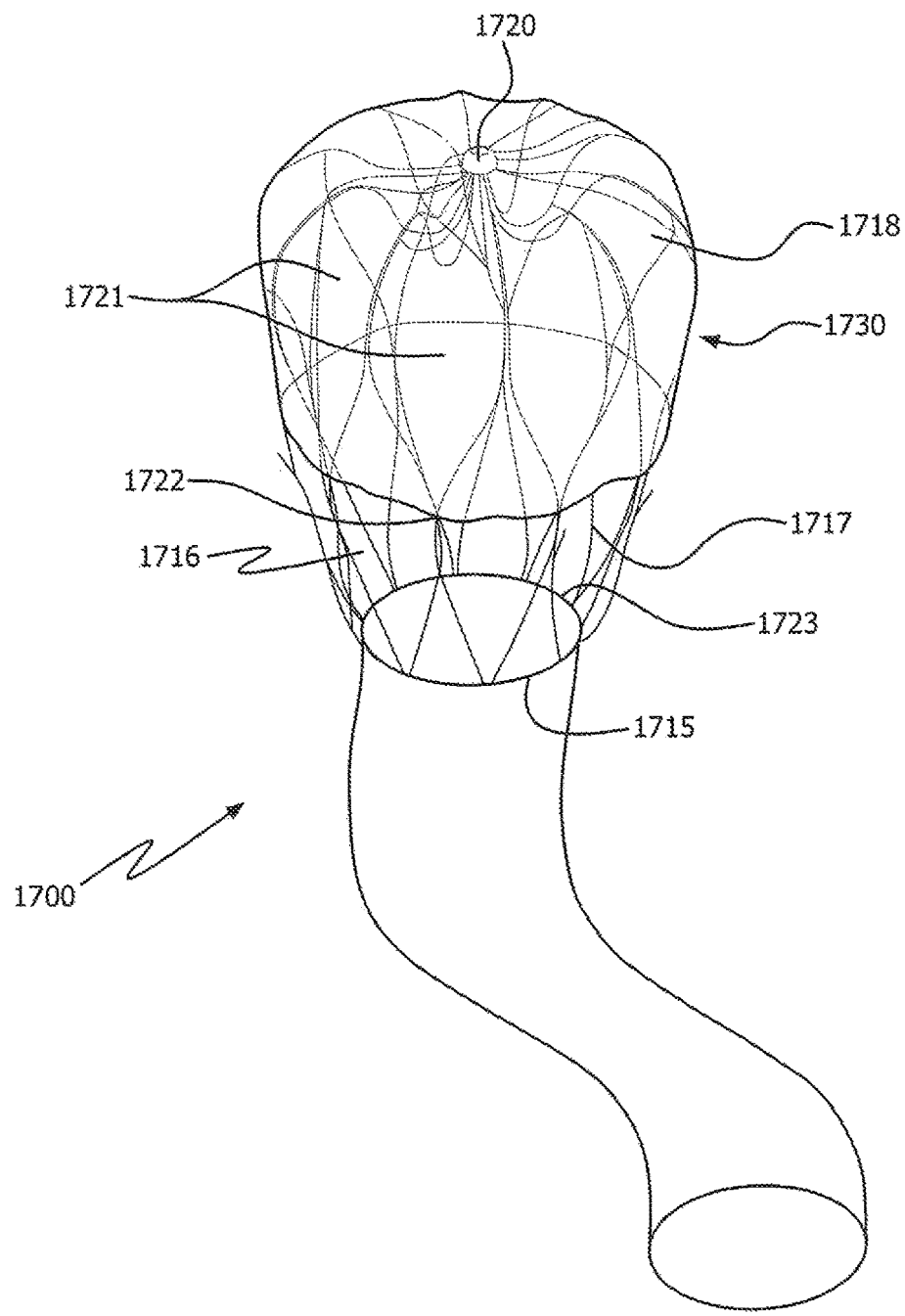
FIG. 17 illustrates one embodiment of an anchorless device comprising a compressible free-floating structure in the stomach with an attached sleeve, according to one embodiment of the present specification.

Referring to FIG. 17, a proximal end of a sleeve 1715 has a plurality of attachments 1717 extending therefrom and is joined to a parachute-like free floating structure 1718 to form an intragastric device 1700, in accordance with one embodiment of the present specification. In some embodiments, the free floating structure is covered, such as with a mesh structure and/or a membrane. In various embodiments, the attachments 1717 comprise sutures, strings, or metal wires. In various embodiments, the sleeve 1715 includes two or more pairs of attachments 1717. In one embodiment, the sleeve 1715 includes six pairs of attachments 1717. In various embodiments, the attachments 1717 have a length in a range of 5 mm to 500 mm. In one embodiment, the attachments 1717 are composed of nylon. A distal end 1723 of each attachment 1717 is attached to the proximal end of the sleeve 1715 and a proximal end 1722 of each attachment 1717 is attached to the free floating structure 1718. In various embodiments, the free floating structure 1718 is glued to each attachment 1717. In at least one embodiment, the free floating structure 1718 includes a plurality of petal-shaped elements 1721 that extend radially and distally from a central element 1720. In various embodiments, the free floating structure 1718 has a diameter in a range of 3 mm to 30 mm. The free floating structure 1718 is designed to add weight to the proximal end of the sleeve 1715 to pull the sleeve 1715 into the proper orientation for deployment. The device 1700 is anchorless as the sleeve 1715 is not physically attached to any part of the GI tract. Owing to its shape, free floating structure 1718 has no sharp edges and is atraumatic to body tissues. Food passes through the spaces 1716 between the attachments 1717 into the sleeve 1715 and exits through the distal end of the sleeve 1715.

In one embodiment, the parachute structure is inverted. It may be noted that the normal parachute design might block larger particulate from passing through the pylorus. Inverting the structure allows larger food particles to pass through. In another embodiment, a hole is added at the top of the normal parachute structure to allow larger particles to pass through.

Figure 18B:
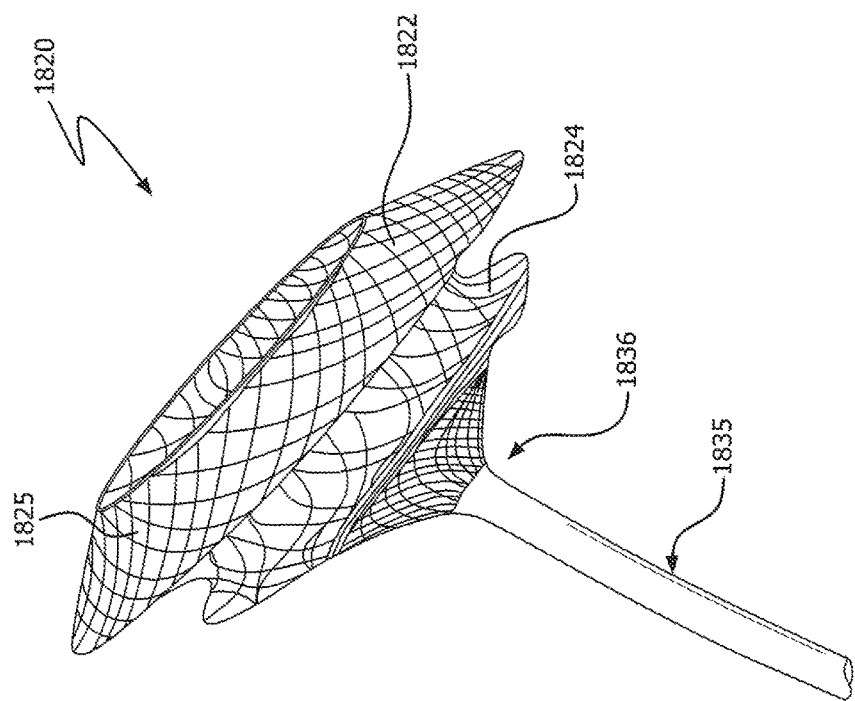
FIG. 18B illustrates a free floating structure with sleeve after deployment, in accordance with another embodiment of the present specification.
Figure 18A:
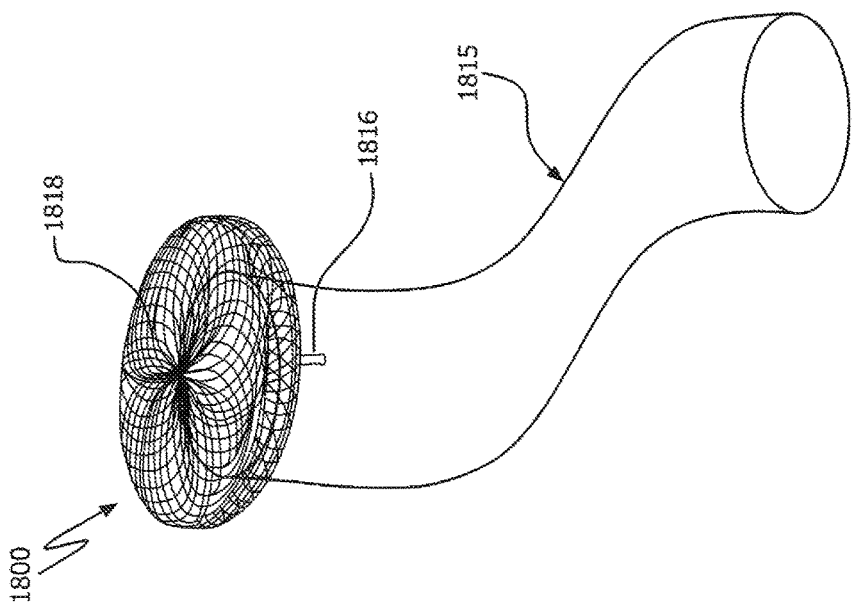
FIG. 18A illustrates another embodiment of a free floating structure with sleeve before deployment.

FIG. 18A illustrates another embodiment of a free floating structure 1818 with sleeve 1815 of an intragastric device 1800. Referring to FIG. 18A, proximal end 1816 of a sleeve 1815 is joined to a double disc-shaped free floating structure 1818, in accordance with one embodiment of the present specification. In one embodiment, the sleeve 1815 is attached to the double disc-shaped structure 1818 by means of strings (not shown). In other embodiments, the double disc-shaped structure 1818 is glued to the sleeve 1815.

FIG. 18B illustrates a double disc-shaped structure 1825 with sleeve 1835 of an intragastric device 1820 in accordance with another embodiment of the present specification. In one embodiment, the double disc-shaped structure 1825 comprises an upper disc 1822 and a lower disc 1824. In an embodiment, the upper disc 1822 has a larger diameter than the lower disc 1824 after deployment. In various embodiments, the upper disc 1822 has a diameter in a range of 3 mm to 30 mm, while the lower disc 1824 has a diameter in the range of 1 to 20 mm. In another embodiment (not shown), the lower disc has a larger diameter than the upper disc. The double disc-shaped structure 1825 is designed to add weight to the proximal end 1836 of the sleeve 1835 to keep the sleeve in place after deployment. Owing to its shape, free floating structure 1825 has no sharp edges and is atraumatic to body tissues.

Figure 19:
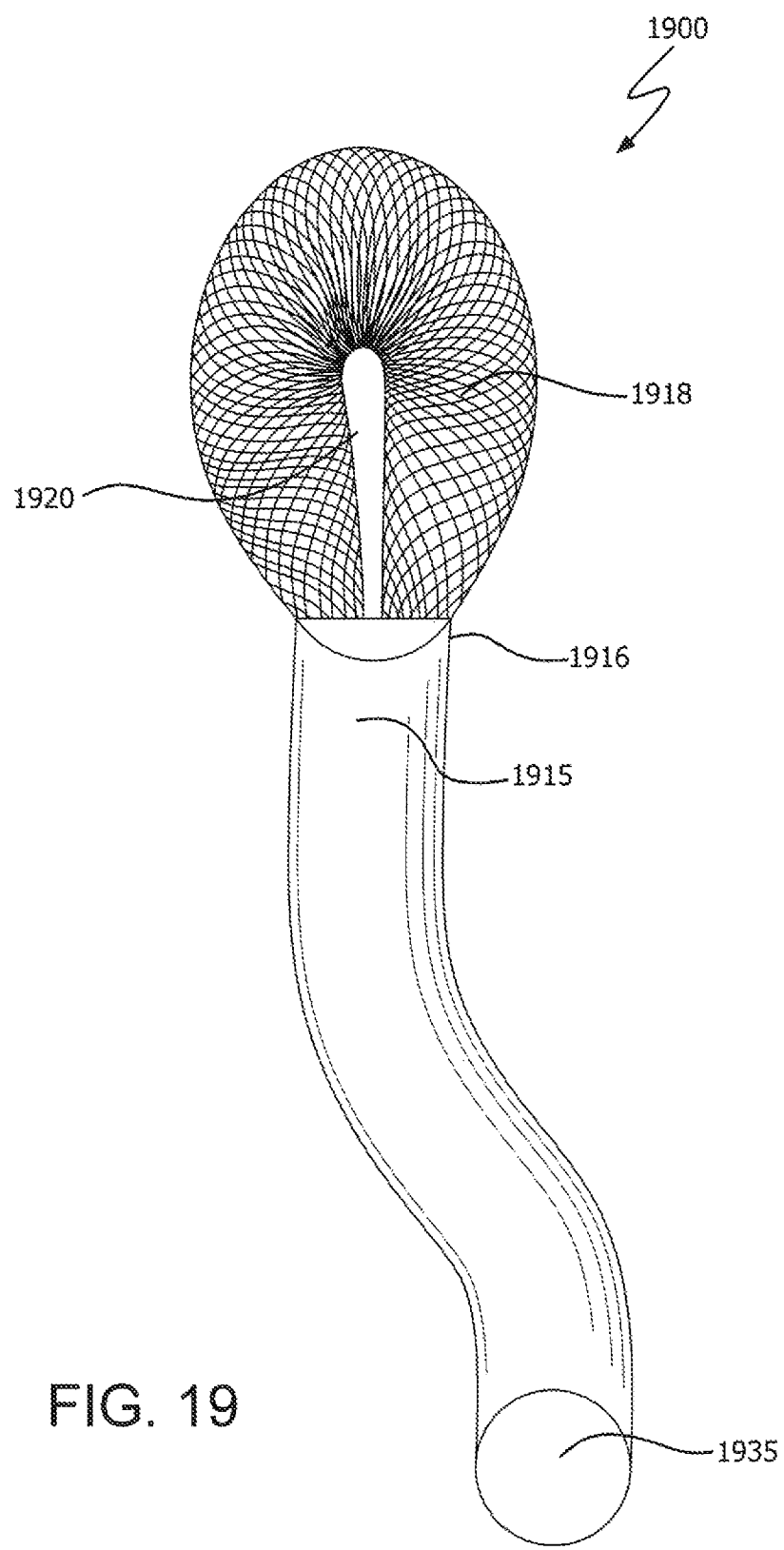
FIG. 19 illustrates another embodiment of an anchorless device comprising a compressible free-floating structure with an attached sleeve, according to one embodiment of the present specification.

FIG. 19 illustrates another embodiment of a free floating structure 1918 with sleeve 1915 of an intragastric device 1900. Referring to FIG. 19, proximal end 1916 of a sleeve 1915 is joined to a horseshoe-shaped free floating structure 1918, in accordance with one embodiment of the present specification. In one embodiment, the sleeve 1915 is attached to the horseshoe-shaped structure 1918 by means of strings (not shown). In other embodiments, the horseshoe-shaped structure 1918 is glued to the sleeve 1915. In various embodiments, the horseshoe has a width in a range of 3 mm to 30 mm at its widest part. The horseshoe 1918 is designed to add weight to the proximal end 1916 of the sleeve 1915 to keep the sleeve 1915 in place after deployment. The device is anchorless as the sleeve is not physically attached to any part of the GI tract. Owing to its shape, free floating structure 1918 has no sharp edges and is atraumatic to body tissues. Food enters through the gap 1920 in the horseshoe shaped structure into the proximal end of the sleeve 1916 and exits through the distal end 1935 of the sleeve.

FIGS. 20A and 20B illustrate top-down and side views respectively, of another embodiment of a free floating structure 2018 and sleeve 2035 of an intragastric device 2000. A circular mesh-shaped free floating structure 2018 is attached to the proximal end 2016 of a sleeve 2015. In one embodiment, the sleeve 2015 is attached to the free floating structure 2018 by means of sutures (not shown). In other embodiments, the free floating structure 2018 is glued to the sleeve 2015. In one embodiment, the circular mesh-shaped structure 2018 comprises first and second curved layers 2020 and 2030, which open up to form an inverted umbrella-like shape after deployment. In various embodiments, the top curved layer 2020 of the structure is smaller and has a diameter in a range of 3 mm to 30 mm, while the bottom curved layer 2030 is larger. The free floating structure 2018 is designed to add weight to the proximal end 2016 of the sleeve 2015 to keep the sleeve in place after deployment. The device 2000 is anchorless as the sleeve 2035 is not physically attached to any part of the GI tract. Owing to its shape, free floating structure 2018 has no sharp edges and is atraumatic to body tissues. Food enters through the mesh structure into the sleeve and exits through the distal end 2035 of the sleeve.

Figure 21B:
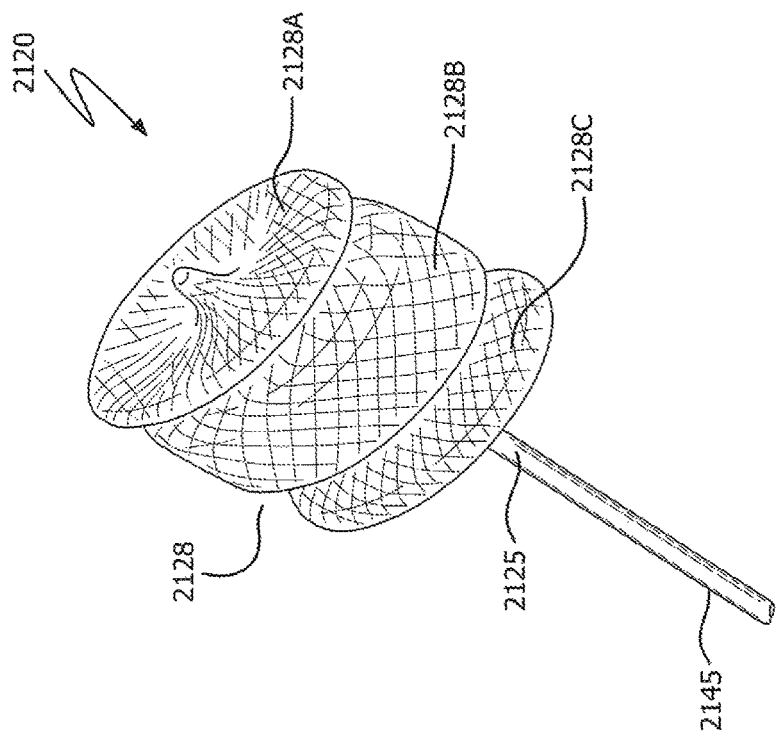
FIG. 21B is an illustration of an intragastric device having an oval shaped wire mesh structure, in accordance with another embodiment of the present specification.
Figure 21A:
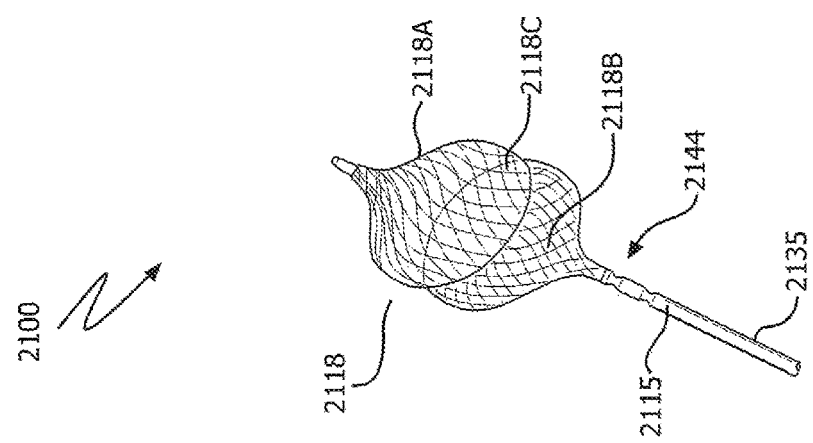
FIG. 21A is an illustration of an intragastric device having an oval shaped wire mesh structure, in accordance with one embodiment of the present specification.

FIG. 21A illustrates another embodiment of a free floating structure 2118 with sleeve 2115 of an intragastric device 2100. Referring to FIG. 21A, proximal end of a sleeve 2115 is joined to a double-teardrop or water drop-shaped free floating structure 2118. In accordance with one embodiment of the present specification, the structure 2118 comprises an upper teardrop portion 2118A in an upright configuration and a lower teardrop portion 2118B in an inverted or upside-down configuration. The two teardrop portions are joined at a junction point 2118C at the distal end of the top teardrop 2118A and the proximal end of the bottom teardrop 2118B. In one embodiment, the sleeve 2115 is attached to the double teardrop shaped structure 2118 by means of sutures (not shown). In other embodiments, the double teardrop-shaped structure 2118 is glued to the sleeve 2115. In various embodiments, the double-teardrop structure 2118 has a diameter in a range of 3 mm to 30 mm at its widest point. In one embodiment, the entirety of the double teardrop shaped free floating structure 2118 is positioned in the stomach and the sleeve extends through the pylorus and into the mid-duodenum. In another embodiment, the junction point 2218C of the double teardrop structure 2118 is configured to be positioned at a patient's pylorus such that the upper teardrop portion 2118A resides in the stomach and the lower teardrop portion 2118B resides in the proximal duodenum. The double-teardrop shaped structure 2118 is designed to add weight to the proximal end 2144 of the sleeve 2115 to keep the sleeve 2115 in place after deployment. The device 2100 is anchorless as the sleeve 2115 is not physically attached to any part of the GI tract. Owing to its shape, free floating structure 2118 has no sharp edges and is atraumatic to body tissues. Food enters through the double teardrop-shaped structure 2118 and exits through the distal end 2135 of the sleeve. In another embodiment, food enters through a hole (not shown) at the proximal end of the sleeve 2115 and exits through its distal end 2135.

FIG. 21B illustrates another embodiment of a free floating structure 2128 with sleeve 2125 of an intragastric device 2120. Referring to FIG. 21B, proximal end of a sleeve 2125 is joined to a free floating structure 2128 comprising an upper portion 2128A, a middle portion 2128B and a lower portion 2128C. In one embodiment, upper portion 2128A is umbrella shaped while lower portion 2118C is in the shape of an inverted umbrella. The middle portion 2128B is cylindrical in one embodiment, and has a diameter ranging from 3 mm to 30 mm. In one embodiment, the sleeve 2125 is attached to the free floating structure 2128 by means of sutures (not shown). In other embodiments, the free floating structure 2128 is glued to the sleeve 2125. The free floating structure 2128 is designed to add weight to the proximal end of the sleeve 2125 to keep the sleeve 2125 in place after deployment. The device 2100 is anchorless as the sleeve 2120 is not physically attached to any part of the GI tract. Owing to its shape, free floating structure 2128 has no sharp edges and is atraumatic to body tissues. Food enters through the free floating structure 2128 and exits through the distal end 2145 of the sleeve. In another embodiment, food enters through a hole (not shown) at the proximal end of the sleeve 2125 and exits through its distal end 2145.

Figure 22:
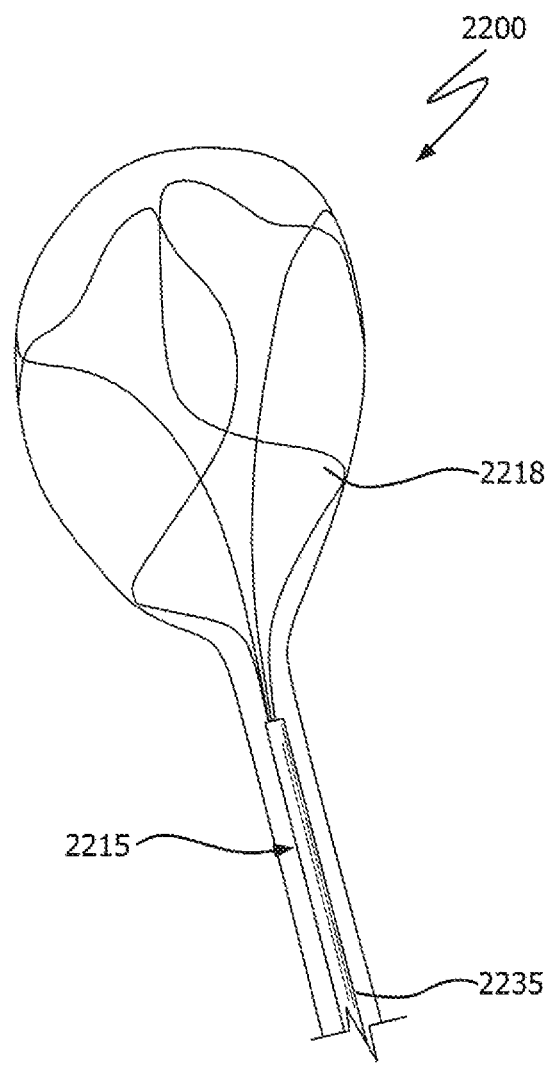
FIG. 22 illustrates another embodiment of an anchorless device comprising a free-floating structure with an attached sleeve, according to one embodiment of the present specification.

FIG. 22 illustrates another embodiment of a free floating structure 2218 with sleeve 2215 of an intragastric device 2200. Referring to FIG. 22, proximal end of a sleeve 2215 is joined to a bulb-shaped free floating structure 2218, in accordance with one embodiment of the present specification. In one embodiment, the sleeve 2215 is attached to the bulb-shaped structure 2218 by means of sutures (not shown). In other embodiments, the bulb-shaped structure 2218 is glued to the sleeve 2215. In various embodiments, the bulb has a diameter in a range of 3 mm to 30 mm at its widest part. The bulb 2218 is designed to add weight to the proximal end of the sleeve 2215 to keep the sleeve 2215 in place after deployment. The device 2200 is anchorless as the sleeve 2215 is not physically attached to any part of the GI tract. Owing to its shape, free floating structure 2218 has no sharp edges and is atraumatic to body tissues. Food enters through an opening at the top of the bulb-shaped structure 2218 and exits through the distal end 2235 of the sleeve.

Figure 23:
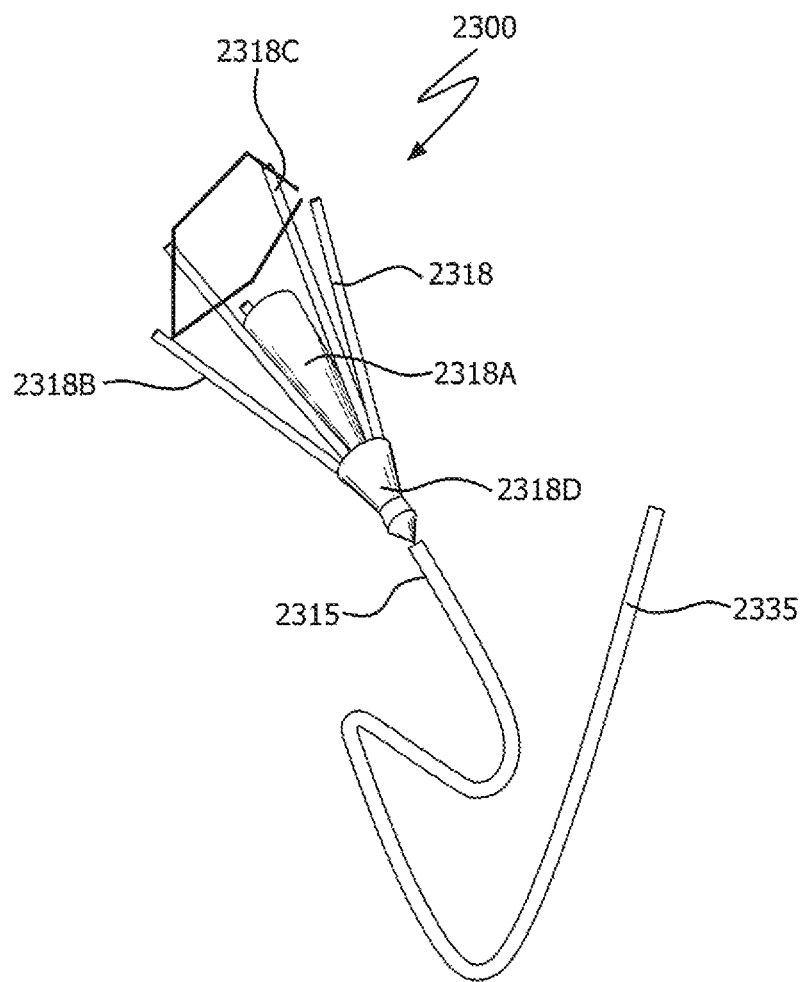
FIG. 23 illustrates another embodiment of an anchorless device comprising a free-floating structure with an attached sleeve, according to one embodiment of the present specification.

FIG. 23 illustrates another embodiment of a free floating structure 2318 with sleeve 2315 of an intragastric device 2300. Referring to FIG. 23, proximal end of a sleeve 2315 is joined to a free floating structure 2318 comprising an inner portion 2318A and an outer portion 2318B. In one embodiment, the inner portion 2318A is in the shape of an inverted cone, while the outer portion 23188 comprises structural elements 2318C arranged in the shape of an inverted square pyramid. In one embodiment, the structural elements 2318C of outer portion 23188 comprise wires, sutures, or strings. In one embodiment, the inner and outer portions of the free floating structure 2318 are attached to the sleeve 2315 by means of a junction component 2318D. The free floating structure 2318 is designed to add weight to the proximal end of the sleeve 2315 to keep the sleeve 2315 in place after deployment. The device 2300 is anchorless as the sleeve 2315 is not physically attached to any part of the GI tract. Owing to its shape, free floating structure 2318 has no sharp edges and is atraumatic to body tissues. Food enters through the free floating structure into the sleeve and exits through the distal end 2335 of the sleeve 2315.

Figure 24:
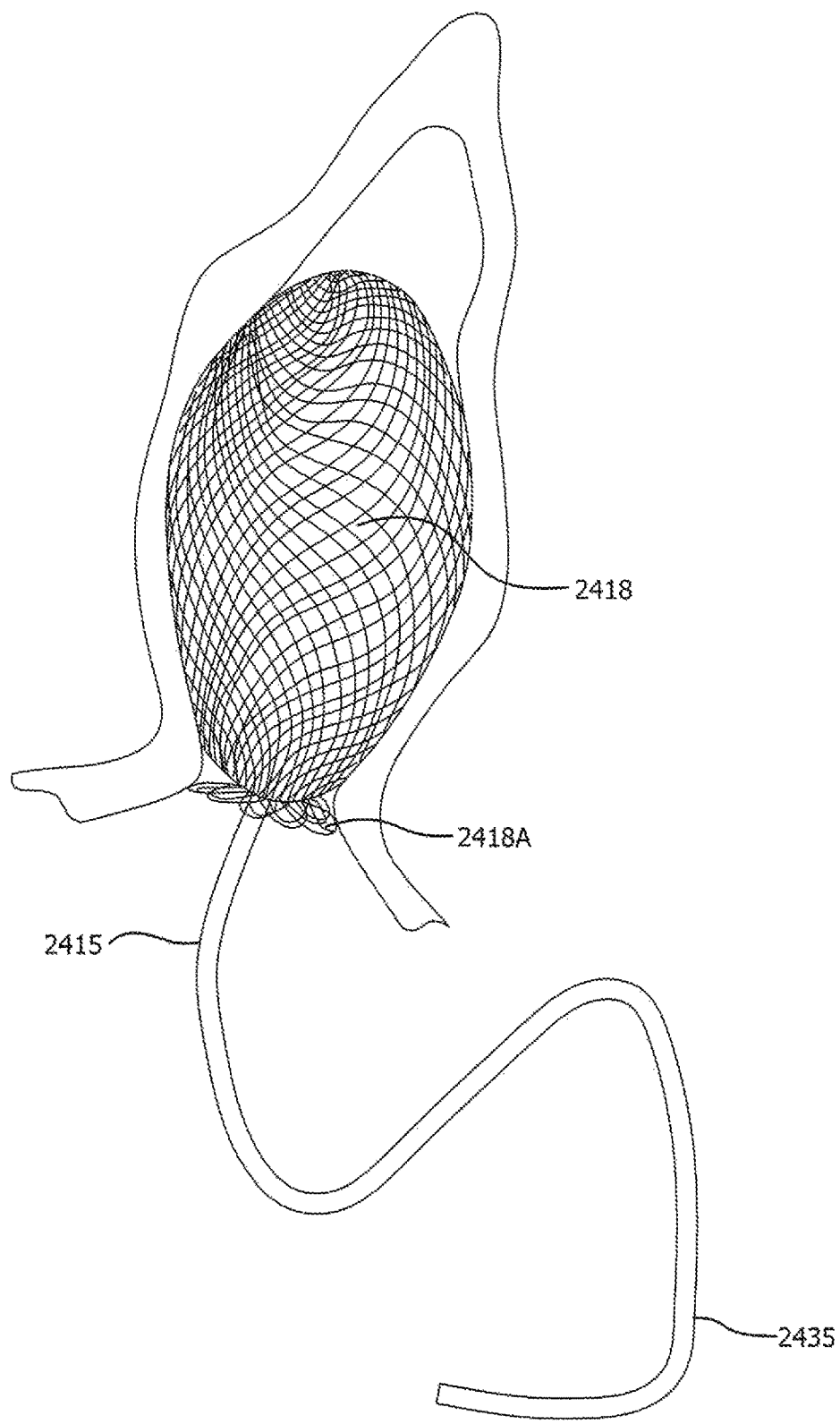
FIG. 24 illustrates another embodiment of an anchorless device comprising a free-floating structure with an attached collar and a sleeve, according to one embodiment of the present specification.
Figure 25:
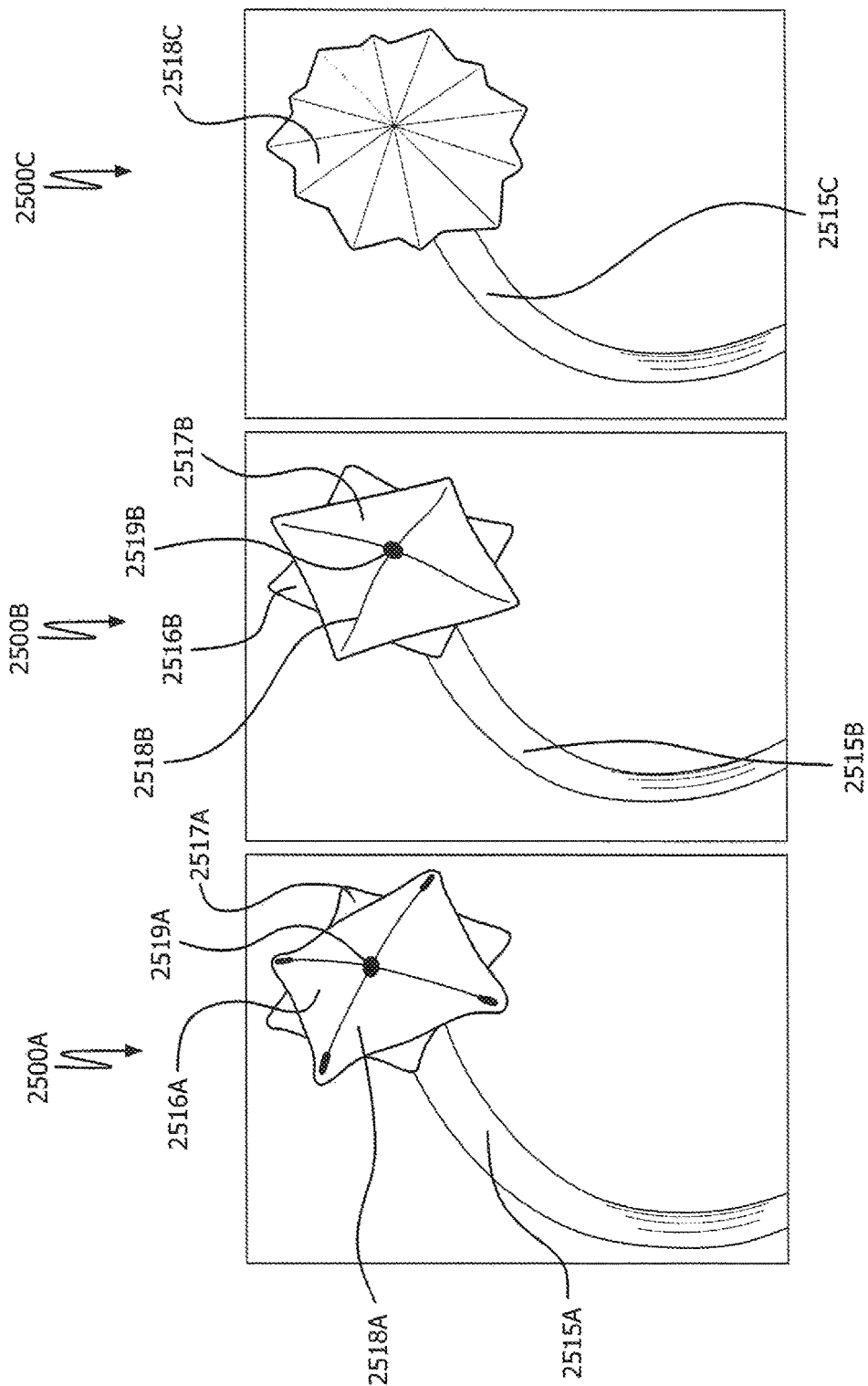
FIG. 25A illustrates another embodiment of a free floating structure, where the free floating structure is flower-shaped.
FIG. 25B illustrates another embodiment of a free floating structure, where the free floating structure is flower-shaped.
FIG. 25C illustrates another embodiment of a free floating structure, where the free floating structure is flower-shaped.

FIG. 24 illustrates yet another embodiment of a free floating structure 2418 with sleeve 2415 of an intragastric device 2400. Referring to FIG. 24, proximal end of a sleeve 2415 is joined to a ball or balloon-shaped free floating structure 2418. In accordance with one embodiment of the present specification, the balloon shaped structure 2418 includes a collar 2418A at its distal end which serves to position the device 2400 in the stomach. In one embodiment, after deployment, the collar 2418A is placed in the duodenal bulb, distal to the pylorus and the balloon shaped free-floating portion 2418 is placed in the stomach, proximal to the pylorus. In one embodiment, the sleeve 2415 is attached to the balloon-shaped structure 2418 by means of sutures (not shown). In other embodiments, the balloon-shaped structure 2418 is glued to the sleeve 2415. In various embodiments, the balloon has a width in a range of 3 mm to 30 mm at its widest part. The balloon-shaped structure 2418 is designed to add weight to the proximal end of the sleeve 2415 to keep the sleeve 2415 in place after deployment. The device 2400 is anchorless as the sleeve 2415 is not physically attached to any part of the GI tract. Owing to its shape, free floating structure 2418 has no sharp edges and is atraumatic to body tissues. Food enters through a hole (not shown) at the proximal end of the sleeve 2415 and exits through its distal end 2435.

FIGS. 25A through 25C illustrate some other embodiments of a free floating structure 2518A, 2518B, 2518C with sleeve 2515A, 2515B, 2515C of an intragastric device 2500A, 2500B, 2500C, where the free floating structure 2518A, 2518B, 2518C is flower-shaped. Referring to FIG. 25A, proximal end of a sleeve 2515A is joined to a free floating structure 2518A comprising two square shaped layers 2516A and 2517A. In one embodiment, a first square shaped layer 2516A is placed diagonally on the top of the second square shaped layer 2517A. The two layers are kept in place by means of a crosswire 2519A placed at the top of both the layers in one embodiment. In another embodiment shown in FIG. 25B, a crosswire 2519B is placed in between the two square shaped layers 2516B and 2517B of a free floating structure 2518B.

Referring to FIG. 25C, a third embodiment of the flower shaped free floating structure 2518C is shown, joined to the proximal end of the sleeve 2515C. Each of the flower-shaped free floating structures 2518A, 2518B, 2518C of the embodiments described in FIGS. 25A, 25B and 25C is designed to add weight to the proximal end of the sleeve 2515A, 2515B, 2515C to keep the sleeve 2515A, 2515B, 2515C in place after deployment. In one embodiment, the sleeve 2515A, 2515B, 2515C is attached to the flower-shaped structure 2518A, 25186, 2518C by means of sutures (not shown). In other embodiments, the flower-shaped structure 2518A, 2518B, 2518C is glued to the sleeve 2515A, 25156, 2515C. The device 2500A, 2500B, 2500C is anchorless as the sleeve 2515A, 25156, 2515C is not physically attached to any part of the GI tract. Owing to its shape, free floating structure 2518A, 2518B, 2518C has no sharp edges and is atraumatic to body tissues. Food enters through the free floating structure 2518A, 2518B, 2518C into the sleeve 2515A, 2515B, 2515C and exits through the distal end of the sleeve 2515A, 2515B, 2515C. In another embodiment, food enters through a hole (not shown) at the proximal end of the sleeve 2515A, 25156, 2515C and exits through its distal end.

Figure 26:
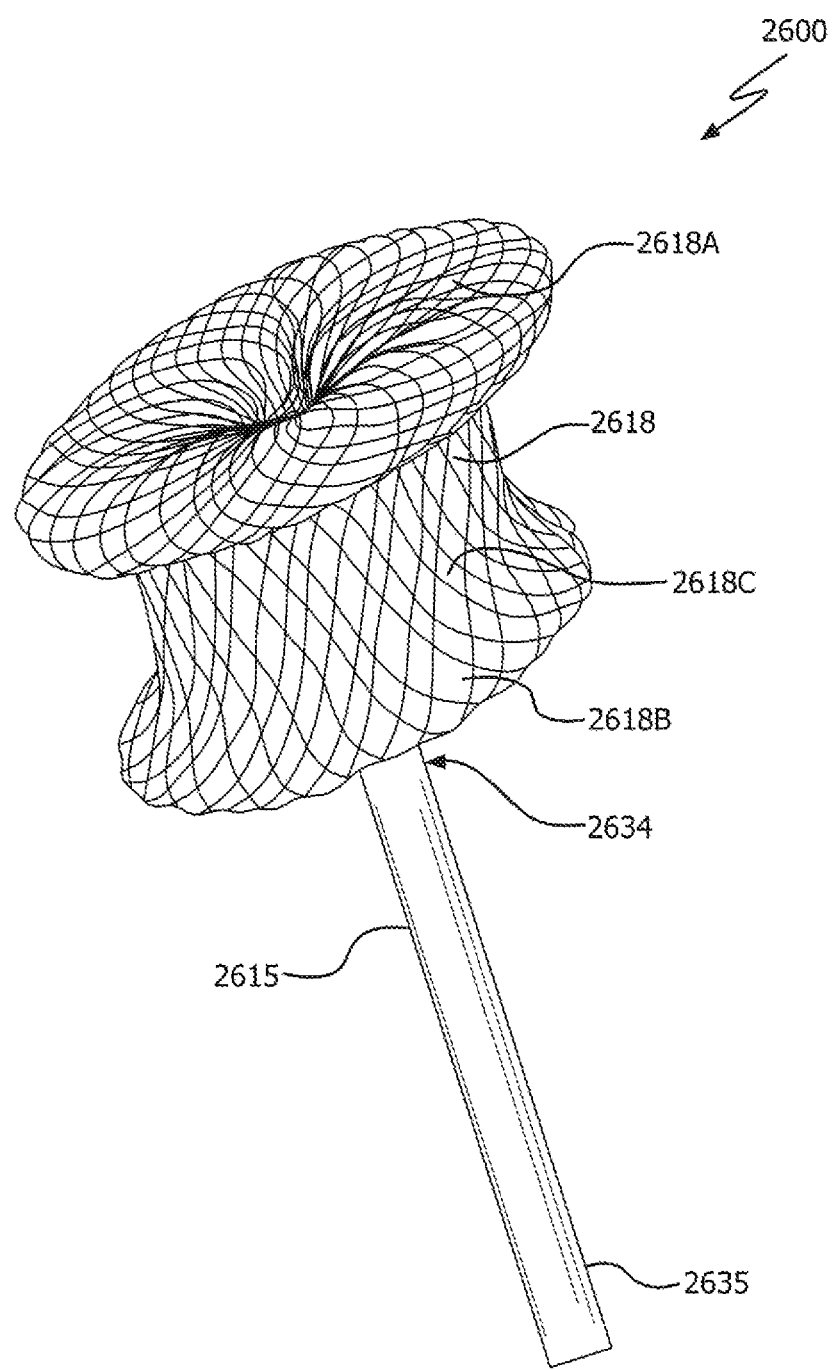
FIG. 26 illustrates yet another embodiment of an anchorless device comprising a free-floating structure with an attached sleeve, according to one embodiment of the present specification.

FIG. 26 illustrates another embodiment of a free floating structure 2618 with sleeve 2615 of an intragastric device 2600. Referring to FIG. 26, proximal end 2634 of a sleeve 2615 is joined to a bobbin-shaped free floating structure 2618. In accordance with one embodiment of the present specification, the structure 2618 comprises an upper disc portion 2618A, a lower disc portion 2618B, and a middle portion 2618C. In one embodiment, the upper disc portion 2618A and a lower disc portion 2618B have an equal diameter. In one embodiment, the diameter of the middle portion 2618C is smaller than that of the upper and lower portions. In one embodiment, the sleeve 2615 is attached to the bobbin-shaped structure 2618 by means of sutures (not shown). In other embodiments, the bobbin-shaped structure 2618 is glued to the sleeve 2615. The bobbin shaped structure 2618 is designed to add weight to the proximal end 2634 of the sleeve 2615 to keep the sleeve 2615 in place after deployment. The device 2600 is anchorless as the sleeve 2615 is not physically attached to any part of the GI tract. Owing to its shape, free floating structure 2618 has no sharp edges and is atraumatic to body tissues. Food enters through the bobbin-shaped structure 2618 and exits through the distal end 2635 of the sleeve 2615. In another embodiment, food enters through a hole (not shown) at the proximal end of the sleeve 2615 and exits through its distal end 2635.

Figure 27:
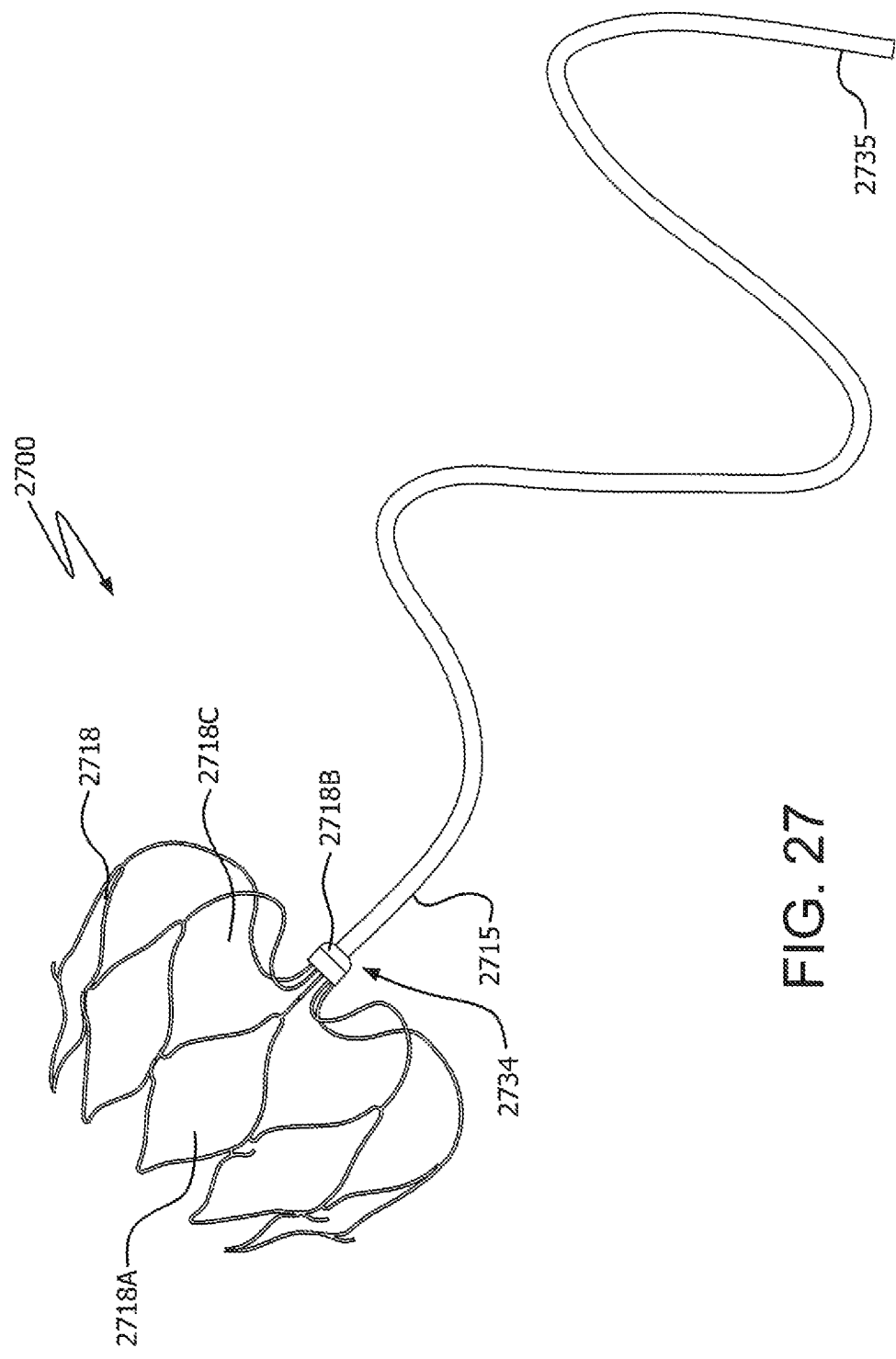
FIG. 27 illustrates another embodiment of a free floating structure, where the free floating structure is lotus-shaped.

FIG. 27 illustrates another embodiment of a free floating structure 2718 with sleeve 2715 of an intragastric device 2700. Referring to FIG. 27, proximal end 2734 of a sleeve 2715 is joined to a lotus-shaped free floating structure 2718. In accordance with one embodiment of the present specification, the structure 2718 comprises structural elements 2718A arranged in a lotus-like configuration. In various embodiments, the structural elements 2718A comprise wires, sutures, or strings. In one embodiment, the lotus-shaped structure 2718 is held together by a junction 2718B, which is attached to the proximal end 2734 of the sleeve 2715. In one embodiment, the proximal end 2734 of the sleeve 2715 is inserted into the junction 27188. The lotus shaped structure 2718 is designed to keep the sleeve 2715 from drifting away into the stomach after deployment. The device 2700 is anchorless as the sleeve 2715 is not physically attached to any part of the GI tract. Owing to its shape, free floating structure 2718 has no sharp edges and is atraumatic to body tissues. Food enters through the gaps 2718C in the lotus-shaped structure 2718 into the sleeve 2715 and exits through the distal end 2735 of the sleeve 2715.

Figure 28:
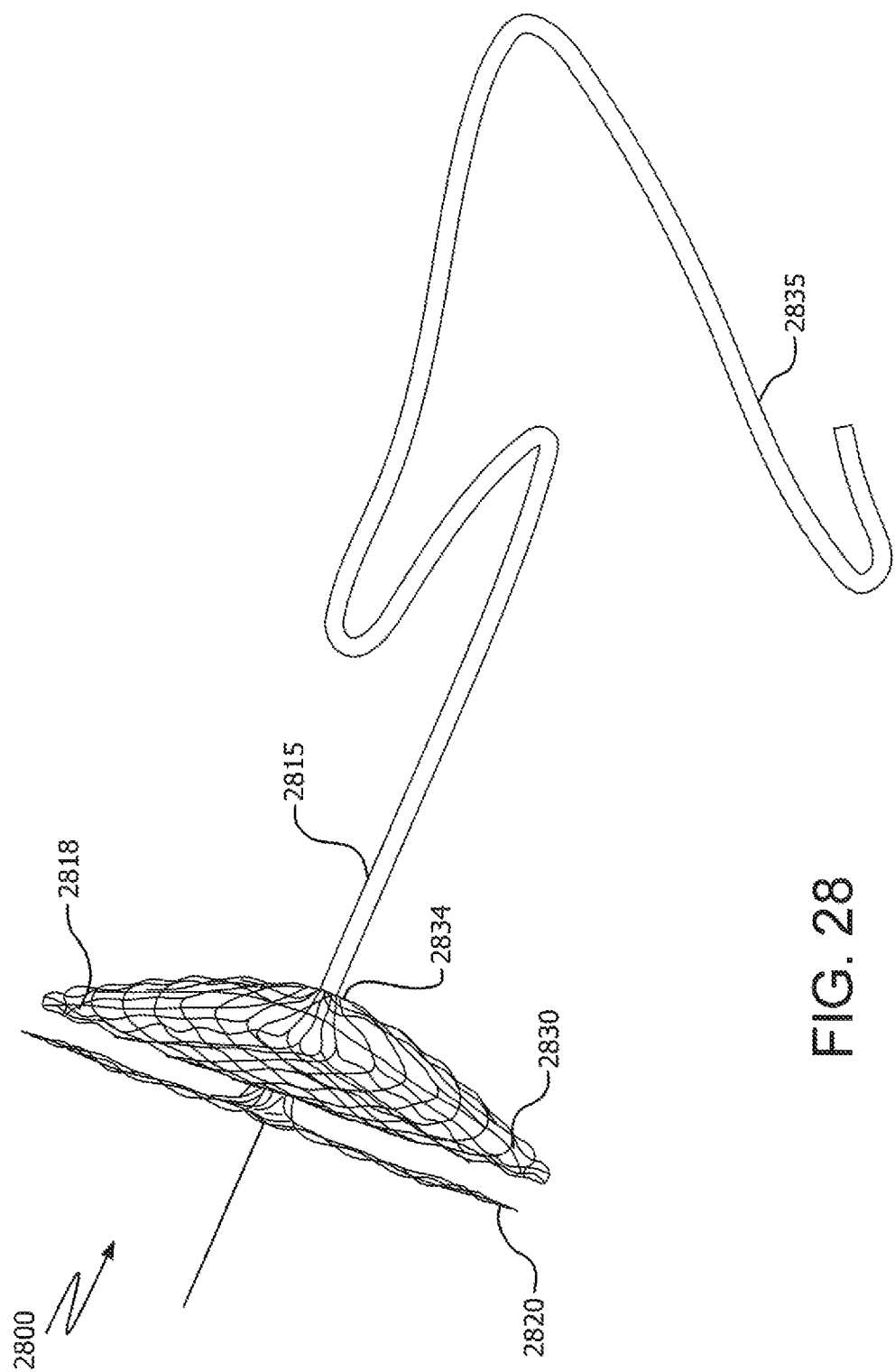
FIG. 28 illustrates yet another embodiment of an anchorless device comprising a free-floating structure with an attached sleeve, according to one embodiment of the present specification.

FIG. 28 illustrates another embodiment of a free floating structure 2818 with sleeve 2815 of an intragastric device 2800. Referring to FIG. 28, proximal end 2834 of a sleeve 2815 is joined to a free floating structure 2818 which comprises an upper disc-shaped layer 2820 and a lower inverted umbrella-shaped layer 2830, in accordance with one embodiment of the present specification. In one embodiment, the sleeve 2815 is attached to the free floating structure 2818 by means of sutures (not shown). In other embodiments, the free floating structure 2818 is glued to the sleeve 2815.

In various embodiments, the upper layer 2820 of the free floating structure 2818 is smaller and has a diameter in a range of 3 mm to 30 mm, while the lower layer 2830 is larger. In one embodiment, both the layers are equal in diameter. The free floating structure 2818 is designed to add weight to the proximal end of the sleeve 2815 to keep the sleeve in place after deployment. The device 2800 is anchorless as the sleeve 2815 is not physically attached to any part of the GI tract. Owing to its shape, free floating structure 2818 has no sharp edges and is atraumatic to body tissues. Food enters through the free floating structure 2818 into the sleeve 2815 and exits through the distal end 2835 of the sleeve 2815. In another embodiment, food enters through a hole (not shown) at the proximal end 2834 of the sleeve 2815 and exits through its distal end 2835.

Figure 29:
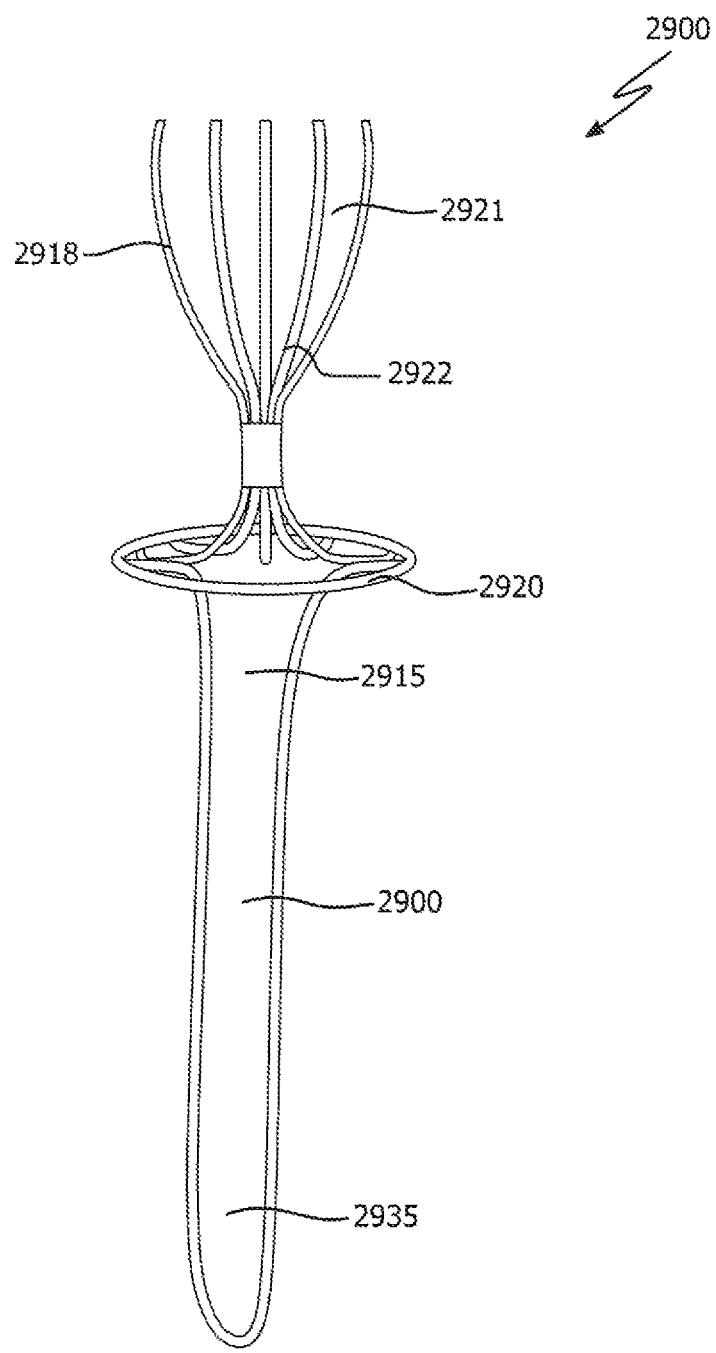
FIG. 29 illustrates another embodiment of a free floating structure, where the free floating structure is wine glass-shaped.

FIG. 29 illustrates another embodiment of a free floating structure 2918 with sleeve 2915 of an intragastric device 2900. Referring to FIG. 29, the proximal end of a sleeve 2915 is joined to a wine glass-shaped free floating structure 2918, in accordance with one embodiment of the present specification. In one embodiment, the proximal end of the sleeve 2915 is broader than the body of the sleeve 2900, and the diameter of the proximal end matches that of the base 2920 of the wine glass shaped structure. In one embodiment, the base has a diameter in a range of 3 mm to 30 mm. In one embodiment, the sleeve 2915 is attached to the wine glass-shaped structure 2918 by means of sutures (not shown). In other embodiments, the wine glass-shaped structure 2918 is glued to the sleeve 2915. In one embodiment, the wine glass structure 2918 comprises connecting portions 2921 and support structure 2922. In one embodiment, the connecting portions 2921 comprises a non-porous membrane and the support structure 2922 comprises wires, sutures, or strings. The wine glass structure 2918 is designed to add weight to the proximal end of the sleeve 2915 to keep the sleeve in place after deployment. The device 2900 is anchorless as the sleeve 2915 is not physically attached to any part of the GI tract. Owing to its shape, free floating structure 2918 has no sharp edges and is atraumatic to body tissues. Food enters through an opening at the top (not shown) of the wine glass-shaped structure 2918 and exits through the distal end 2935 of the sleeve 2915.

Figure 30:
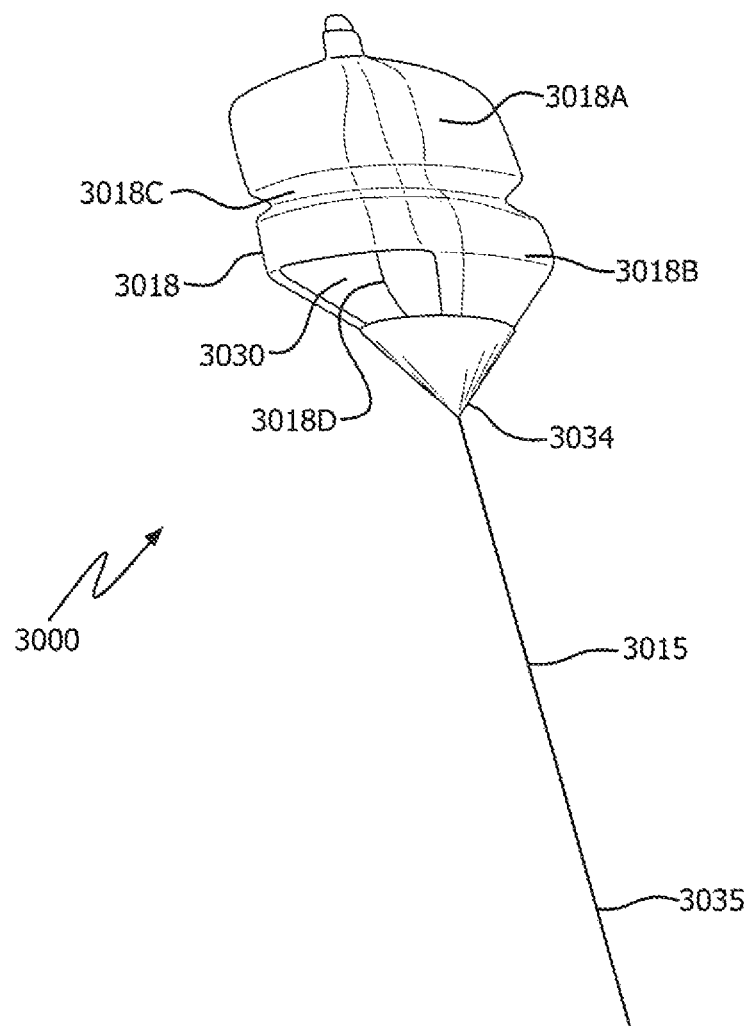
FIG. 30 illustrates another embodiment of an anchorless device comprising a free-floating structure with an attached sleeve, according to one embodiment of the present specification.

FIG. 30 illustrates another embodiment of a free floating structure 3018 with sleeve 3015 of an intragastric device 3000. Referring to FIG. 30, proximal end 3034 of a sleeve 3015 is joined to a double balloon-shaped free floating structure 3018. In accordance with one embodiment of the present specification, the structure 3018 comprises an upper balloon portion 3018A in an upright configuration and a lower balloon portion 30188 in an inverted or upside-down configuration. The two balloon portions 3018A, 3018B are joined at a junction point 3018C at the distal end of the top balloon 3018A and the proximal end of the bottom balloon 30188. In one embodiment, the double balloon-shaped structure 3018 has wires 3018D extending from it, which attach the structure to the proximal end of the sleeve 3015, which in one embodiment is conical in shape. In other embodiments, the double balloon-shaped structure 3018 is glued to the sleeve 3015. In various embodiments, the double balloon has a diameter in a range of 3 mm to 30 mm at its widest point. The double balloon shaped structure 3018 is designed to add weight to the proximal end of the sleeve 3015 to keep the sleeve 3015 in place after deployment. The device 3000 is anchorless as the sleeve 3015 is not physically attached to any part of the GI tract. Owing to its shape, free floating structure 3018 has no sharp edges and is atraumatic to body tissues. Food enters through an opening 3030 in the double balloon structure 3018 and exits through the distal end 3035 of the sleeve 3015. In another embodiment, food enters through a hole (not shown) at the proximal end of the sleeve 3015 and exits through its distal end 3035.

Figure 31:
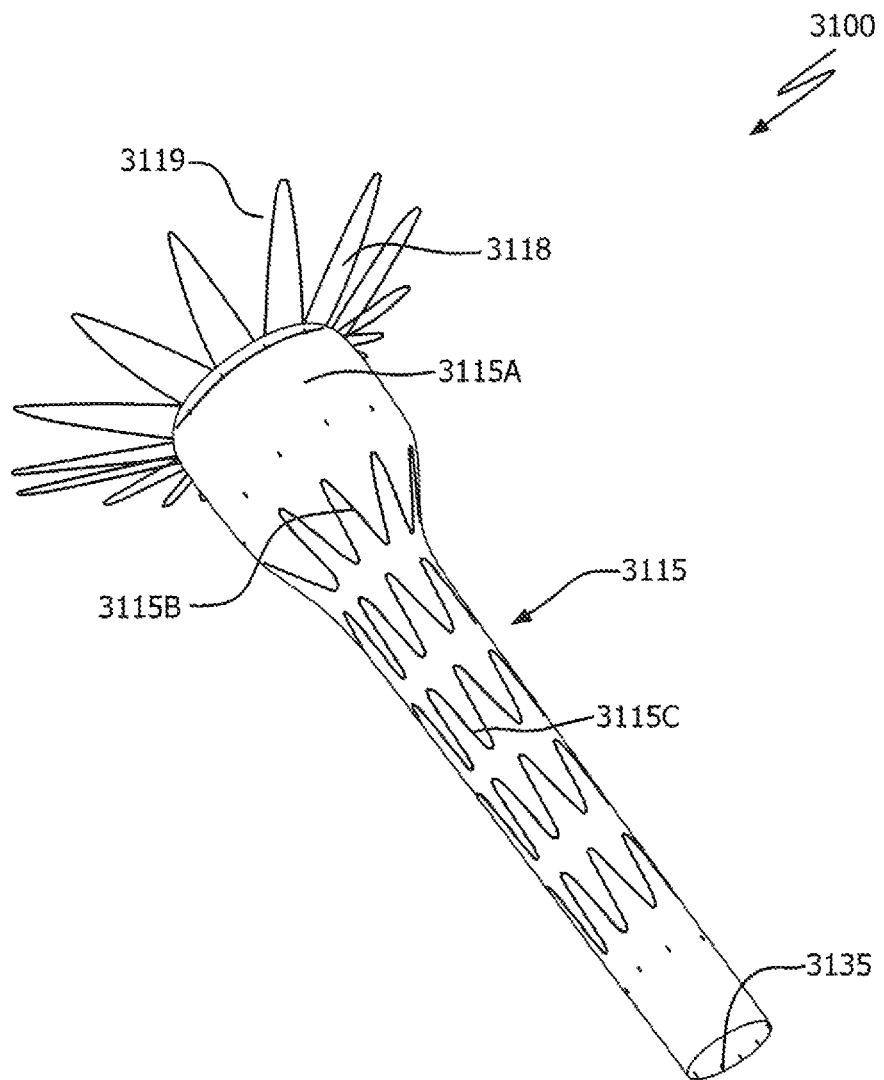
FIG. 31 illustrates yet another embodiment of the free floating structure, where the free floating structure is microphone-shaped, according to one embodiment of the present specification.

FIG. 31 illustrates another embodiment of a free floating structure 3118 with sleeve 3115 of an intragastric device 3100. Referring to FIG. 31, a free floating structure 3118 is shaped like a flower and comprises flower petal shaped portions 3119 extending outward while the sleeve 3515 is funnel shaped and comprises an upper proximal portion 3115A, a middle transitional portion 31158 and a lower distal portion 3115C. In one embodiment, lower distal portion 3115C is a long portion with a consistent diameter along its length, while the upper proximal portion 3115A is shorter with a consistent, larger diameter along its length. The middle transitional portion 3115B in one embodiment has a decreasing diameter as it extends distally, wherein the diameter at the proximal end of the transitional portion 31158 is equal to the diameter of the proximal portion 3115A and the diameter at the distal end of the transitional portion 31158 is equal to the diameter of the distal portion 3115C. Food enters through an opening at the proximal end of the proximal portion 3115A of the sleeve 3115 and exits through the distal end 3135 of the sleeve 3115.

Figure 32:
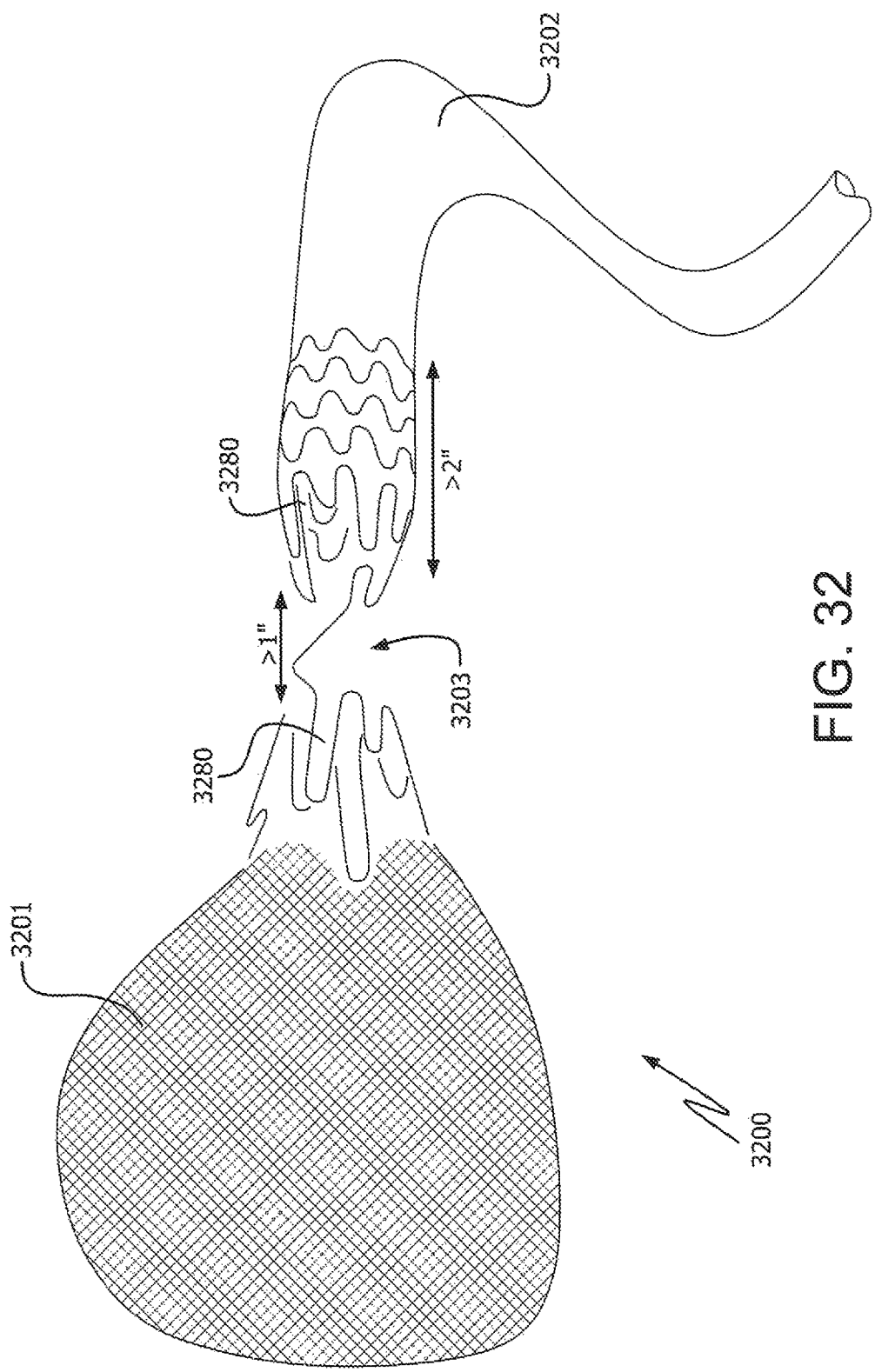
FIG. 32 provides an illustration of a stent support for a sleeve component of an intragastric device, in accordance with one embodiment of the present specification.
Figure 33:
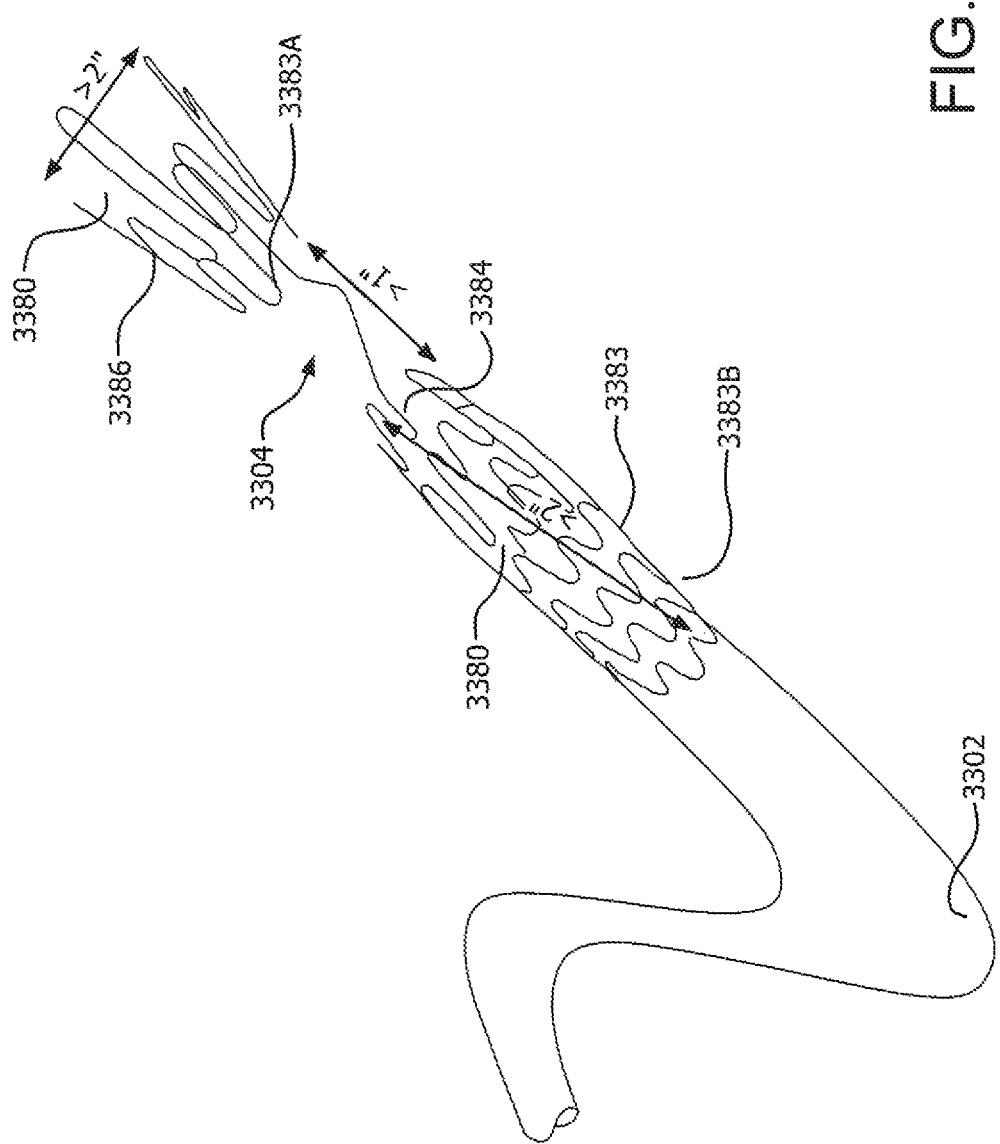
FIG. 33 provides another illustration of a stent support for a sleeve component of an intragastric device, in accordance with one embodiment of the present specification.

In some embodiments, a stent is inserted at the proximal end of the sleeve to keep the sleeve in place. FIGS. 32 and 33 provide an illustration of a stent support for a sleeve component of an intragastric device, in accordance with one embodiment of the present specification. Referring to FIG. 32, the intragastric device 3200 comprises a free floating component 3201 and a sleeve component 3202. In one embodiment, the free floating component stays in the stomach, proximal to the pylorus 3203, and the sleeve extends through the pylorus 3203 and into the mid-duodenum. A stent support 3280 is inserted in the sleeve to prevent migration and acts as an atraumatic anchor. In various embodiments, the stent support 3280 may be inserted in the sleeve on either one side or both the sides of the pylorus 3203. The stent component 3280 provides structural integrity to the sleeve 3202, such that it will not collapse as a result of intestinal contractions while still allowing the sleeve component 3202 to be flexible enough to conform to the curves of the gastrointestinal tract. In one embodiment, the length of the stent component below the pylorus is of the order of 2-3 inches.

Referring to FIG. 33, in the pictured embodiment, the stent support 3380 in the sleeve 3302 includes a plurality of rings 3383 formed from CZ' shape segments of wire. In another embodiment (not shown), the stent support comprises a continuous spiral wire support wherein wires of the spiral are configured into 'Z' shapes. Referring again to FIG. 33, some of the rings 3383A are placed in the area above the pylorus, while the rest of the rings 3383B are placed in the area below the pylorus 3304. In one embodiment, ring segments 3383A and 3383B are connected by a wire segment 3384. In some embodiments, each ring 3383 has length in a range of 1-2 cm. In some embodiments, each connecting wire 3384 has a length in a range of 1-2 inches. In one embodiment, the proximal end of the stent support 3380 includes a funnel shaped ring segment 3386. In various embodiments, the funnel shaped ring segment 3386 has a diameter sized to match the diameter of an anti-migration free floating component at the distal end of a wire mesh structure to which it will be attached. In one embodiment, the diameter of the funnel shaped segment 3386 ranges from 2-3 inches.

Figure 34:
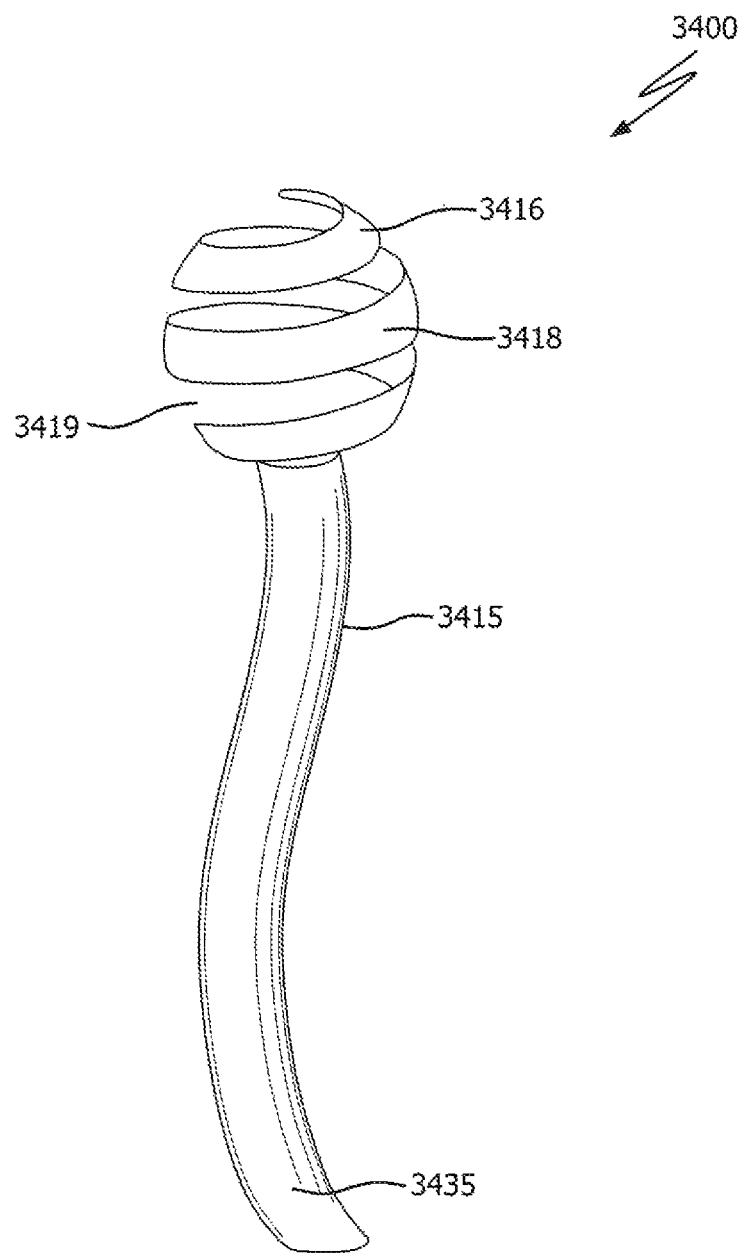
FIG. 34 illustrates another embodiment of an anchorless device comprising a free-floating structure with an attached sleeve, according to one embodiment of the present specification.

FIG. 34 illustrates another embodiment of a free floating structure 3418 with sleeve 3415 of an intragastric device 3400. Referring to FIG. 34, a proximal end of a sleeve 3415 is joined to an orange peel-shaped free floating structure 3418, in accordance with one embodiment of the present specification. In one embodiment, the orange peel-shaped structure 3418 comprises a spiral shaped ribbon 3416 approximating the shape of a peel removed from an orange. In one embodiment, the structure 3418 is composed of a shape memory material such as Nitinol, so that it can be compressed partially by gastric contractions but is able return to its original shape. In one embodiment, the orange peel structure 3418 has a diameter in a range of 3 mm to 30 mm at its widest part. In one embodiment, the sleeve 3415 is attached to the orange peel-shaped structure 3418 by means of sutures (not shown). In other embodiments, the orange peel-shaped structure 3418 is glued to the sleeve 3415.

The orange peel structure 3418 is designed to add weight to the proximal end of the sleeve 3415 to keep the sleeve 3415 in place after deployment. The device 3400 is anchorless as the sleeve 3415 is not physically attached to any part of the GI tract. Owing to its shape, free floating structure 3418 has no sharp edges and is atraumatic to body tissues. Food enters through spaces 3419 in the ribbon of the orange peel shaped structure 3418, through an opening at the proximal end of the sleeve 3415, and exits through the distal end 3435 of the sleeve 3415.

In some embodiments of the present specification, a sleeve of an intragastric device begins just distal to the esophagus, rather than at and proximate the pylorus and extends through the duodenum.

A shown in previous embodiments of FIGS. 2A, 2B, 3A and 3B, the intragastric device includes a mesh structure and a collar. In one embodiment, the mesh structure is eliminated and simply the collar component is attached to the sleeve and acts to keep the sleeve from migrating. This reduces the size and weight of the device, besides providing an atraumatic anchoring mechanism.

Also, the mesh devices of previous embodiments are used to provide a feeling of fullness. This feature is provided in the present embodiment by applying pressure at the upper end of the stomach, near the esophagus, which would add feeling of fullness. In one embodiment (not shown), an additional free floating structure, such as a parachute, balloon, collar, etc. is added at the proximal end of a similar free floating structure. Thus, there is an upper structure and a lower structure and the two structures are connected to one another. Further, a sleeve is attached to the distal end of the lower structure and the entire device is flexible. In one embodiment, the entire device conforms to shape of stomach. The bottom end applies pressure to the pyloric section to stretch the stomach and the top end applies pressure to the esophageal/cardiac section of stomach to stretch the stomach, both giving a feeling of fullness.

It may be noted that while prior art includes an atraumatic gastrointestinal anchor distal to the pylorus, the embodiments of the present specification differ in that they do not pierce the tissue and keep the anchoring structure above the pylorus. Further, the anchoring structures are free-floating and not attached to any portion of the GI tract, while still keeping the device in place. Hence the present device is essentially anchorless.

In another embodiment, the device comprises a biodegradable atraumatic anchoring component which disintegrates a few months after deployment, leaving the device in place. In some embodiments, the anchoring component degrades after 6 months. In one embodiment, the intragastric device comprises a stent with a sleeve attached to it. The device stays in the GI tract after deployment, and a few months later the sleeve is removed, leaving the stent in place. In one embodiment, a suture connects the stent to the sleeve. For removal, a physician pulls on the suture, allowing the sleeve to detach and be passed. In some embodiments, the sleeve is detached and passed 3 to 6 months following implantation.

In one embodiment, the present specification comprises an anchorless gastrointestinal device having a pre-deployment shape and a post deployment shape and constituting a rigid member and a flexible member wherein the flexible member is longer and thinner than the rigid member in its post-deployment shape and has a surface optimized for adherence and growth of microorganisms. In one embodiment, the rigid member is a freely floating mesh structure and the flexible structure is a freely floating sleeve structure with a surface designed to promote micro-organism adherence and growth. Thus, in one embodiment, gastrointestinal devices of the present specification are used for delivery of prebiotic or probiotic therapy into a patient's small intestine, thereby leading to desired therapeutic effect. In one embodiment, the desired therapeutic effect includes weight loss, glycemic control, or treatment of irritable bowel syndrome, *clostridium difficile* or any other condition responsive to a prebiotic or a probiotic therapy.

Benefits of probiotics are well known in the art and include the decrease of potentially pathogenic gastro-intestinal microorganisms; the reduction of gastro-intestinal discomfort; the strengthening of the immune system; the improvement of the skin's function; the improvement of bowel regularity; the strengthening of the resistance to cedar pollen allergens; the decrease in body pathogens; the reduction of flatulence and bloating; the protection of DNA; the protection of proteins and lipids from oxidative damage; and the maintaining of individual intestinal microbiota in subjects receiving antibiotic treatment. Probiotics have to be alive when administered. However, most of the probiotics administered orally do not tend to colonize a patient's small bowel and within a few weeks of cessation of probiotic therapy, the therapeutic effect also ceases. Thus, continuous administration of probiotics is required for a sustained therapeutic effect.

Prior art includes instances of probiotics being administered by devices planted endoscopically in a patient's gastrointestinal system. However, administering live bacteria with an anchored device in the gastrointestinal system increases the risk of these bacteria entering the patient's blood stream, leading to serious infections. For example, liver abscesses have been recently reported owing to the use of probiotics administered by an anchored sleeve device. The risk of infection increases multifold in diabetic patients. Therefore, it is not advisable to use probiotics with an anchored sleeve.

The above problems of prior art are overcome and the use of probiotics is leveraged for the benefits of patients in one embodiment of the present specification, by using anchorless devices as described above to deliver probiotics to the patient's gut. In various embodiments, any of the above described anchorless intragastric devices is used, which has a pre-deployment shape and a post deployment shape. The anchorless device comprises a rigid member such as a free floating structure mesh structure, attached to a flexible member, such as a freely floating sleeve structure. In one embodiment, the flexible member has a surface optimized for adherence and growth of microorganisms. In one embodiment, the flexible member comprises a strip, instead of a sleeve, optimized for adherence and growth of microorganisms.

In one embodiment the sleeve structure is impregnated with a probiotic, such as *Lactobacillus* or *Bifidobacterium*. In another embodiment, the sleeve structure has a surface area optimized to allow for adherence of microorganisms. In another embodiment, the sleeve structure has a surface optimized to allow for growth of microorganisms. In one embodiment the sleeve structure comprises a corrugated surface. In another embodiment, the sleeve structure has a honey-comb surface. In another embodiment, the sleeve has woven fiber structure.

In another embodiment, the sleeve structure has a surface optimized to allow for formation of a biofilm with a probiotic species, such as *Bifidobacterium longum* or *Lactobacillus reuteri*. A biofilm is any group of microorganisms in which cells stick to each other on a surface. These adherent cells are frequently embedded within a self-produced matrix of extracellular polymeric substance (EPS). Biofilm extracellular polymeric substance, which is also referred to as slime, is a polymeric conglomeration generally composed of extracellular DNA, proteins, and polysaccharides. As known in the art, biofilms may form on living or non-living surfaces.

In one embodiment, the sleeve structure has an increased surface area or length to improve biofilm formation.

In one embodiment, the anchorless intragastric devices of the present specification are used to deliver prebiotics to a patient's gut. A prebiotic is a selectively fermented ingredient that allows specific changes, both in the composition and/or activity in the gastrointestinal microflora that confers benefits upon host well-being and health. In diet, prebiotics are typically non-digestible fiber compounds that pass undigested through the upper part of the gastrointestinal tract and stimulate the growth and/or activity of advantageous bacteria that colonize the large bowel by acting as substrate for them. The prebiotic definition does not emphasize a specific bacterial group. Generally, however, it is assumed that a prebiotic should increase the number and/or activity of bifidobacteria and lactic acid bacteria. The importance of the bifidobacteria and the lactic acid bacteria (LABs) is that these groups of bacteria may have several beneficial effects on the host, especially in terms of improving digestion (including enhancing mineral absorption) and the effectiveness and intrinsic strength of the immune system.

Thus, in one embodiment the sleeve component of the anchorless intragastric device is impregnated with a prebiotic. In one embodiment, the sleeve has a microporous structure allowing for certain nutrients (prebiotics) from inside the sleeve to be transferred to the bacteria (probiotics) outside the sleeve.

In another embodiment, the anchorless intragastric devices of the present specification are used to deliver synergistic combinations of probiotics and prebiotics, called synbiotics, to a patient's gut.

In one embodiment, the sleeve structure carrying a prebiotic, probiotic or a combination thereof is used for certain duration to temporarily change the constitution of a patient's microbiome. In another embodiment, the sleeve structure carrying a prebiotic, probiotic or a combination thereof is used for certain duration to permanently change the constitution of a patient's microbiome.

It should be appreciated that the present disclosure is intended to provide a teaching of several exemplary embodiments of the present invention and is should not be limited to the specific structures disclosed herein. Other variations of the disclosed embodiments, which would be understood by those of ordinary skill, are covered by the present application and are within the scope of the invention, as further defined by the claims.

What is claimed is:

1. An intragastric device comprising:
   an elongate sleeve having a proximal end and a distal end; and
   a plurality of attachment elements extending proximally from said proximal end of said sleeve; and
   an anchoring structure discrete from and coupled to said plurality of attachment elements, said anchoring structure having a plurality of petal-shaped elements extending radially and distally from a central element located at a proximal end of the anchoring structure, each of the plurality of petal shaped elements tapering to a distal tip,
   wherein a distal end of each attachment element is affixed to said proximal end of said sleeve, and
   wherein a proximal end of each attachment element is attached to the distal tip of a respective one of the plurality of petal-shaped elements of said anchoring structure.

2. The intragastric device of claim 1, further comprising a covering over said anchoring element.

3. The intragastric device of claim 1, wherein said anchoring element has a diameter from 3 mm to 30 mm.

4. The intragastric device of claim 1, wherein said anchoring structure is configurable between a compressed configuration and an expanded configuration.

5. The intragastric device of claim 1, wherein said anchoring structure comprises a shape memory material.

6. An implantable medical device comprising:
   an elongate sleeve having a proximal end and a distal end; and
   a plurality of attachment elements extending proximally from said proximal end of said sleeve; and
   an anchoring structure discrete from and coupled to said plurality of attachment elements, said anchoring structure having a plurality of petal-shaped elements extending radially and tapering distally from a central element to terminate at a distal tip, the distal tip being coupled to a respective one of the plurality of attachment elements, the central element and the petal-shaped elements defining a proximal end of the anchoring structure,
   wherein a distal end of each attachment element is affixed to said proximal end of said sleeve, and
   wherein a proximal end of each attachment element is attached to said anchoring structure.

7. The implantable medical device of claim 6, further comprising a covering over said anchoring element.

8. The implantable medical device of claim 6, wherein said anchoring element has a diameter from 3 mm to 30 mm.

9. The implantable medical device of claim 6, wherein said anchoring structure is configurable between a compressed configuration and an expanded configuration.

10. The implantable medical device of claim 6, wherein said anchoring structure comprises a shape memory material.

* * * * *